US008000801B2

(12) United States Patent
Stevenson et al.

(10) Patent No.: US 8,000,801 B2
(45) Date of Patent: *Aug. 16, 2011

(54) SYSTEM FOR TERMINATING ABANDONED IMPLANTED LEADS TO MINIMIZE HEATING IN HIGH POWER ELECTROMAGNETIC FIELD ENVIRONMENTS

(75) Inventors: Robert A. Stevenson, Canyon Country, CA (US); Buehl E. Truex, Glendora, CA (US); Barry C. Muffoletto, Alden, NY (US); Warren S. Dabney, Orchard Park, NY (US); Christine A. Frysz, Orchard Park, NY (US); Christopher Michael Williams, Lancaster, NY (US); Holly Noelle Moschiano, Lancaster, NY (US); Jeff Fleigle, Brooklyn Park, MN (US); Kishore Kumar Kondabatni, Williamsville, NY (US); Richard L. Brendel, Carson City, NV (US); Robert Shawn Johnson, North Tonawanda, NY (US); Scott Brainard, Columbia Heights, MN (US); Henry R. Halperin, Pikesville, MD (US); Albert C. Lardo, Baltimore, MD (US)

(73) Assignee: Greatbatch Ltd., Clarence, NY (US)

( * ) Notice: Subject to any disclaimer, the term of this patent is extended or adjusted under 35 U.S.C. 154(b) by 26 days.

This patent is subject to a terminal disclaimer.

(21) Appl. No.: 12/693,836

(22) Filed: Jan. 26, 2010

(65) Prior Publication Data

US 2010/0174349 A1 Jul. 8, 2010

Related U.S. Application Data

(63) Continuation-in-part of application No. 12/686,137, filed on Jan. 12, 2010, which is a continuation-in-part of application No. 12/489,921, filed on Jun. 23, 2009, now Pat. No. 7,751,903, which is a continuation-in-part of application No. 10/123,534, filed on Apr. 15, 2002, now Pat. No. 7,844,319.

(60) Provisional application No. 61/149,833, filed on Feb. 4, 2009, provisional application No. 61/147,432, filed on Jan. 26, 2009, provisional application No. 61/144,102, filed on Jan. 12, 2009, provisional application No. 60/283,725, filed on Apr. 13, 2001.

(51) Int. Cl.
*A61N 1/08* (2006.01)
(52) U.S. Cl. .......................................... 607/63; 607/60
(58) Field of Classification Search .................... 607/63, 607/115, 116
See application file for complete search history.

(56) References Cited

U.S. PATENT DOCUMENTS

| | | | |
|---|---|---|---|
| 5,896,627 A | 4/1999 | Cappel et al. | |
| 5,905,627 A | 5/1999 | Brendel et al. | |
| 7,689,288 B2 * | 3/2010 | Stevenson et al. | 607/63 |
| 7,751,903 B2 * | 7/2010 | Stevenson et al. | 607/63 |
| 2007/0288058 A1 * | 12/2007 | Halperin et al. | 607/2 |
| 2008/0024912 A1 | 1/2008 | Mallary et al. | |

* cited by examiner

*Primary Examiner* — Carl H. Layno
*Assistant Examiner* — Jon-Eric C. Morales
(74) *Attorney, Agent, or Firm* — Kelly Lowry & Kelley, LLP

(57) ABSTRACT

An energy management system facilitates the transfer of high frequency energy coupled into an implanted abandoned lead at a selected RF frequency or frequency band, to an energy dissipating surface. This is accomplished by conductively coupling the implanted abandoned lead to the energy dissipating surface of an abandoned lead cap through an energy diversion circuit including one or more passive electronic network components whose impedance characteristics are at least partially tuned to the implanted abandoned lead's impedance characteristics.

56 Claims, 34 Drawing Sheets

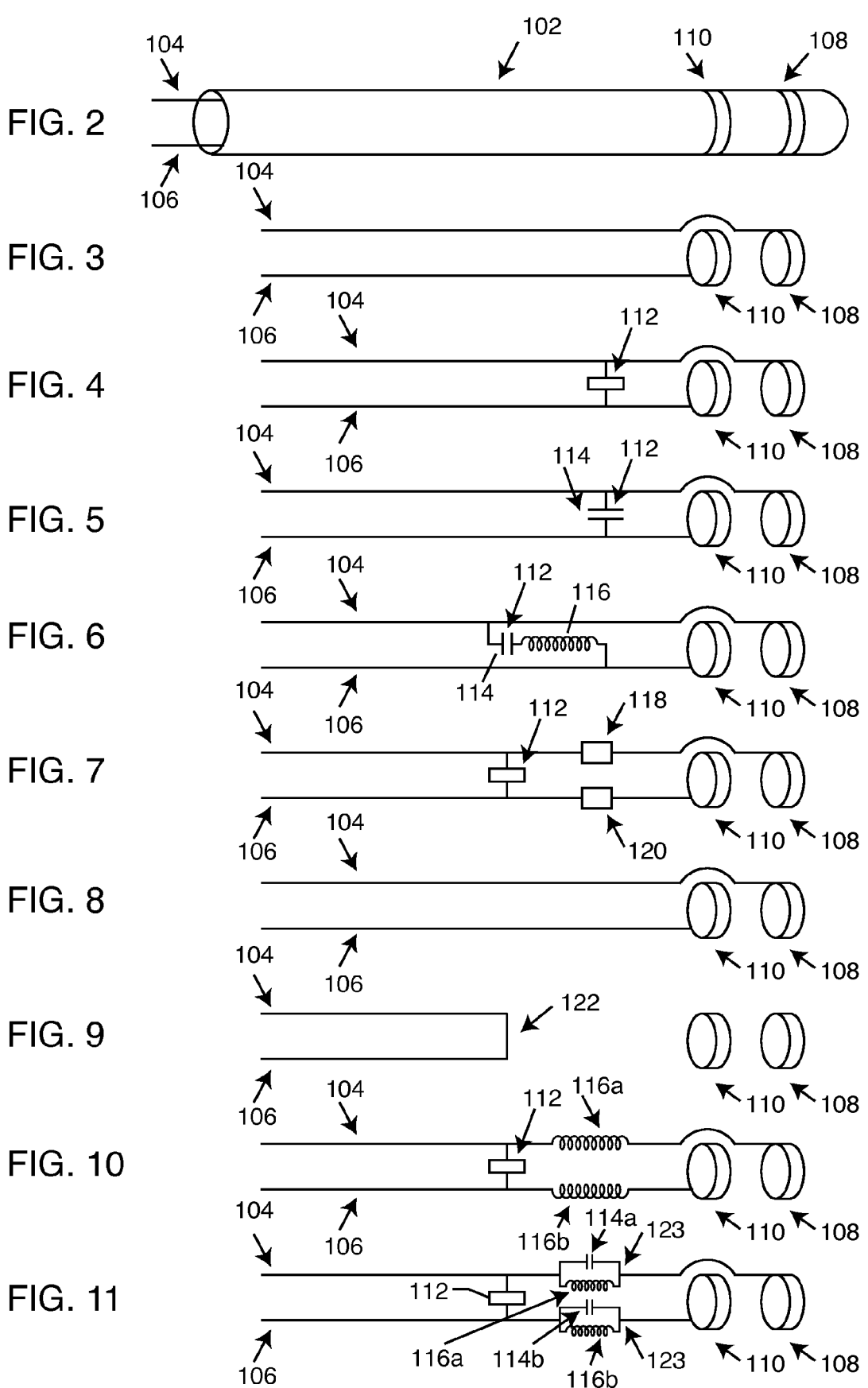

MRI PULSED RF (HIGH) FREQUENCY MODEL

MRI GRADIENT (LOW) FREQUENCY MODEL

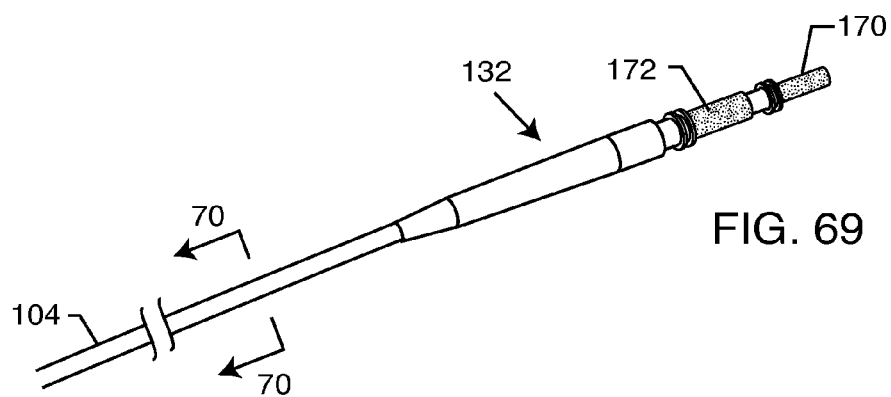
FIG. 69
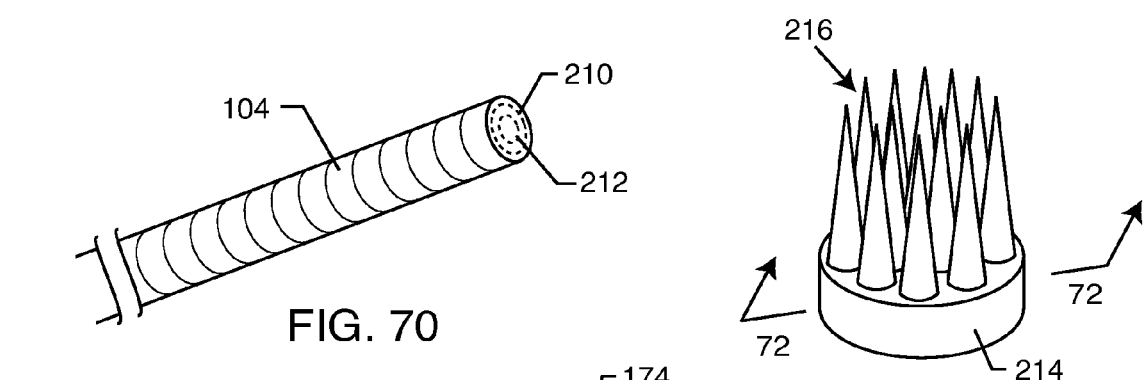
FIG. 70
FIG. 71
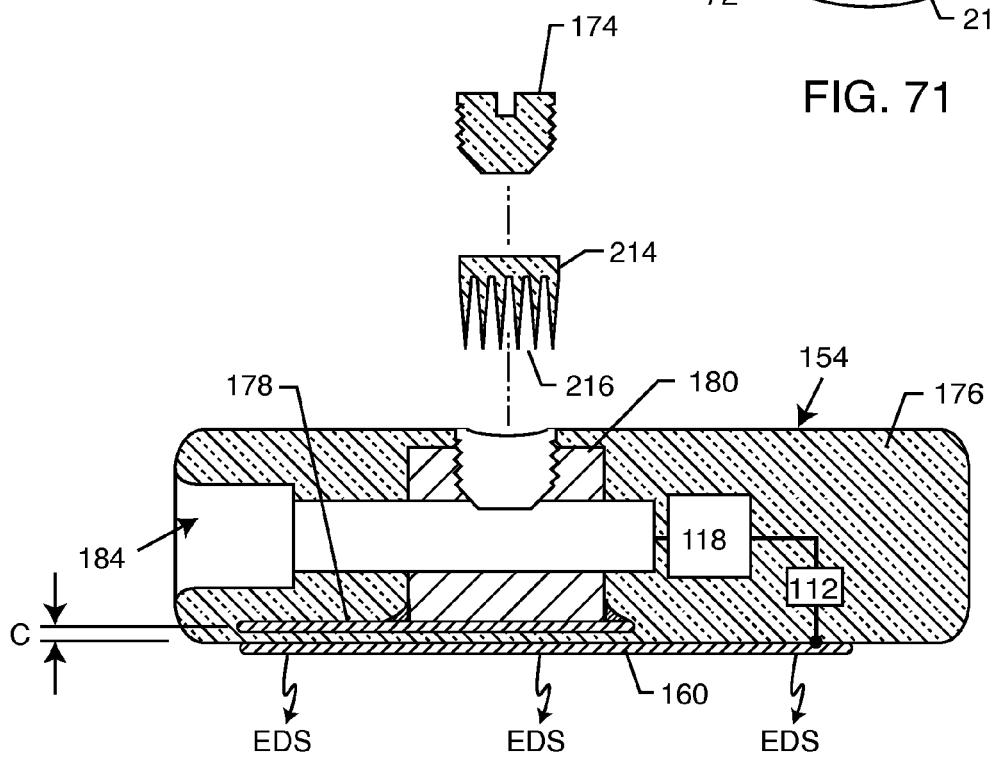
FIG. 72

SYSTEM FOR TERMINATING ABANDONED IMPLANTED LEADS TO MINIMIZE HEATING IN HIGH POWER ELECTROMAGNETIC FIELD ENVIRONMENTS

CROSS-REFERENCE TO RELATED APPLICATION(S)

This Application claims benefit of 61/147,432 filed Jan. 26, 2009 and is a Continuation-In-Part (CIP) of Ser. No. 12/686, 137 filed Jan. 12, 2010 which is a CIP of Ser. No. 12/489,921, filed Jun. 23, 2009, now U.S. Pat. No. 7,751,903 and claims benefit of 61/149,833 filed Feb. 4, 2009 and claims benefit of 61/144,102 filed Jan. 12, 2009 also Ser. No. 12/489,921 filed Jun. 23, 2009 is a CIP of Ser. No. 10/123,534 filed Apr. 15, 2002 now U.S. Pat. No. 7,844,319, which claims benefit of 60/283,725 filed Apr. 13, 2001.

BACKGROUND OF THE INVENTION

This invention generally relates to the problem of energy induced onto abandoned implanted leads during medical diagnostic procedures such as magnetic resonant imaging (MRI). Specifically, the radio frequency (RF) pulsed field of MRI can couple to an implanted lead in such a way that electromagnetic forces (EMFs) are induced in the lead. The amount of energy that is induced is related to a number of complex factors, but in general, is dependent upon the local electric field that is tangent to lead and the integral of the electric field strength along the lead. In certain situations, these EMFs can cause currents to flow into distal electrodes or in the electrode interface with body tissue. It has been documented that when this current becomes excessive, that overheating of said lead or its associated electrode or overheating of the associated interface with body tissue can occur. There have been cases of damage to such body tissue which has resulted in loss of capture of cardiac pacemaking pulses, tissue damage, severe enough to result in brain damage or multiple amputations, and the like. The present invention relates generally to methods of redirecting said energy to a novel energy dissipating abandoned lead proximal end cap rather than the lead body or a distal tip electrode-to-tissue interface.

There are many reasons why cardiac rhythm device lead wires are abandoned. These include loss of pacing capture or a high impedance at the distal electrode to tissue interface. Another reason includes lead breakage or damage to lead insulation. Yet another reason would be simply due to replacement and relocation of the active implantable medical device (AIMD). Removal of implanted lead wires is not an easy process, particularly after they've been implanted for a long period of time. Reference is made to a paper given at the 28th Annual Scientific Sessions of the Heart Rhythm Society, in Session 113 on Friday, May 11, 2007 by Dr. Bruce L. Wilkoff, M. D. of the Cleveland Clinic Foundation and was entitled, ICD LEAD EXTRACTION OF INFECTED AND/OR REDUNDANT LEADS. The slides from that paper are incorporated herein by reference and will be referred to again simply as the Wilkoff reference. Referring to various Figures in the paper, one can see the amount of tissue that is adhering to the leads as they are extracted. During extraction procedures, there are various cutting tools and laser tools that are slipped down over the lead that are used to dislodge the lead from surrounding tissue growth. This is a very delicate process because it's a tortuous path. For example, if the laser or mechanical cutting tool were to penetrate while going around a corner of an artery wall, this would result in a life-threatening situation for the patient. Accordingly, lead wires are often simply abandoned and then clipped off or capped and left inside the patient. As mentioned, the above examples were for implanted cardiac rhythm device leads. There are also many reasons why leads are abandoned for neurostimulators and other types of AIMDs. Spinal cord, deep brain or cochlear leads are often abandoned simply because the electrodes are so difficult to extract. The present invention is applicable to all types of abandoned implanted leads.

It's also been demonstrated in the literature that abandoned lead wires can be quite dangerous during magnetic resonance imaging (MRI) procedures. That is, the energy that is coupled from the pulsed RF field of the magnetic resonance imaging field creates significant energy in the lead wire system. In most pacemakers and cardioverter defibrillators, there is an EMI filter that's present at the point of lead wire ingress through the hermetic titanium housing of the device. These prior art feedthrough capacitors (or monolithic chip capacitors) form a fairly low impedance at MRI RF pulse frequencies. The RF pulsed frequency for a 1.5 Tesla MR scanner is approximately 64 MHz. For a 3 Telsa scanner, the RF pulsed frequency is approximately 128 MHz. The capacitive reactance of the prior art EMI feedthrough capacitors is generally below 2 ohms at these frequencies. Therefore, when the pacemaker or ICD is plugged into the proximal end of the lead wire, much of the RF energy from MRI is shunted to the titanium can or housing of the AIMD. This is why there have been some reports of warming of the pectoral pocket during MR scans. One is referred to a paper given at Heart Rhythm 2007 by Dr. Rod Gimbal. He reported on a number of ICD patients, including one patient who reported warming of the pectoral pocket area during the MR scan. When the physician placed his hand over the patient's AIMD in the pocket area, the doctor himself could feel the heat radiating into his own hand. This could have been caused by MR gradient field eddy current heating, however, it is more likely that the heating was caused by transfer of energy through the feedthrough capacitor to the housing of the cardiac pacemaker.

Accordingly, when a pacemaker or ICD is unplugged and the abandoned lead(s) is capped or cut off, there is no path for the energy to escape at the proximal end into the surrounding tissues. Instead, what happens is the energy instead dissipates at the still-connected distal tip electrode or distal ring electrode. Severe overheating has been documented in the literature, including burns to cardiac tissue. Therefore, what is needed is an abandoned lead cap that is capable of transferring energy at the proximal end. For example, for a cardiac pacemaker, this would typically be in the pectoral pocket where the pacemaker was previously removed. In some cases, a new pacemaker with new leads is implanted in the same pectoral pocket as the abandoned leads. The pectoral pocket, which embodies fat and muscle tissues, is not nearly as sensitive to thermal injury as compared to myocardial tissue, the spinal cord, or deep brain tissue. For all of these types of AMIDs, pectoral implants are common. Similar analogies can be made for spinal cord stimulators and other types of neuromodulation systems. In other words, when one makes the choice, it will be better to slightly overheat the pectoral muscle than it would to overheat the distal electrode tissue interface. It will be obvious that overheating of myocardial, nerves or brain tissue can be debilitating or even life threatening. It is also a feature of the present invention to dissipate said energy over a large enough surface area of a novel abandoned lead cap such as to prevent overheating to the point where temperature rise would result in thermal injury.

MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contraindication for pacemaker or neurostimulator patients means that these patients are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF Pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted leads or devices. For example, for magnetic resonance imaging devices operating at the same magnetic field strength and also at the same SAR level, considerable variations have been found relative to heating of implanted leads. It is speculated that SAR level alone is not a good predictor of whether or not an implanted device or its associated lead system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. At the recent International Society for Magnetic Resonance in Medicine (ISMRM), which was held on 5-6 NOV 2005, it was reported that certain research systems are going up as high as 11.7 Tesla and will be ready sometime in 2010. This is over 100,000 times the magnetic field strength of the earth. A static magnetic field can induce powerful mechanical forces and torque on any magnetic materials implanted within the patient. This would include certain components within the cardiac pacemaker itself and/or lead systems. It is not likely (other than sudden system shut down) that the static MRI magnetic field can induce currents into the pacemaker lead system and hence into the pacemaker itself. It is a basic principle of physics that a magnetic field must either be time-varying as it cuts across the conductor, or the conductor itself must move within a specifically varying magnetic field for currents to be induced.

The second type of field produced by magnetic resonance imaging is the pulsed RF field which is generated by the body coil or head coil. This is used to change the energy state of the protons and elicit MRI signals from tissue. The RF field is homogeneous in the central region and has two main components: (1) the electric field is circularly polarized in the actual plane; and (2) the H field, sometimes generally referred to as the net magnetic field in matter, is related to the electric field by Maxwell's equations and is relatively uniform. In general, the RF field is switched on and off during measurements and usually has a frequency of 21 MHz to 64 MHz to 128 MHz depending upon the static magnetic field strength. The frequency of the RF pulse for hydrogen scans varies by the Lamor equation with the field strength of the main static field where: RF PULSED FREQUENCY in MHz=(42.56) (STATIC FIELD STRENGTH IN TESLA). There are also phosphorous and other types of scanners wherein the Lamor equation would be different. The present invention applies to all such scanners.

The third type of electromagnetic field is the time-varying magnetic gradient fields designated $B_X$, $B_Y$, $B_Z$, which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and electro-magnetic interference (EMI) are induced into an implanted lead system. At very low frequency (VLF), voltages are induced at the input to the cardiac pacemaker as currents circulate throughout the patient's body and create voltage drops. Because of the vector displacement between the pacemaker housing and, for example, the tip electrode, voltage drop across the resistance of body tissues may be sensed due to Ohms Law and the circulating current of the RF signal. At higher frequencies, the implanted lead systems actually act as antennas where voltages (EMFs) are induced along their length. These antennas are not very efficient due to the damping effects of body tissue; however, this can often be offset by extremely high power fields (such as MRI pulsed fields) and/or body resonances.

Magnetic field coupling into an implanted lead system is based on loop areas. For example, in an AIMD abandoned lead, there is a loop formed by the lead as it comes from the abandoned lead proximal tip to its distal tip electrode, for example, located in the right ventricle. The return path is through body fluid and tissue generally straight from the tip electrode in the right ventricle back up to the abandoned lead cap or end. This forms an enclosed area which can be measured from patient X-rays in square centimeters. Per ANSI/AAMI National Standard PC69, the average loop area is 200 to 225 square centimeters. This is an average and is subject to great statistical variation. For example, in a large adult patient with an abdominal pacemaker implant, the implanted loop area is much larger (around 400 square centimeters).

Relating now to the specific case of MRI, the magnetic gradient fields would be induced through enclosed loop areas. However, the pulsed RF fields, which are generated by the body coil, would be primarily induced into the lead system by antenna action. Subjected to RF frequencies, the lead itself can exhibit complex transmission line behavior.

At the frequencies of interest in MRI, RF energy can be absorbed and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AIMD and the length and trajectory of its associated lead(s). For example, it will make a difference how much EMF is induced into a pacemaker lead system as to whether it is a left or right pectoral implant. In addition, the routing of the lead and the lead length are also very critical as to the amount of induced current and heating that would occur. Also, distal tip design is very important as it can heat up due to MRI RF induced energy. The cause of heating in an MRI environment is twofold: (a) RF field coupling to the lead can occur which induces significant local heating; and (b) currents induced between the distal tip and tissue during MRI RF pulse transmission sequences can cause local Ohms Law heating in tissue next to the distal tip electrode of the implanted lead. The RF field of an MRI scanner can produce enough energy to induce RF voltages in an implanted lead and resulting currents sufficient to damage some of the adjacent myocardial tissue. Tissue ablation (destruction resulting in scars) has also been observed. The effects of this heating are not readily detectable by monitoring during the MRI. Indications that heating has occurred would include an increase in pacing threshold, venous ablation, Larynx or esophageal ablation, myocardial perforation and lead penetration, or even arrhythmias caused by scar tissue. Such long term heating effects of MRI have not been well studied yet for all types of AIMD lead geometries. There can also be localized heating problems associated with various types of electrodes in addition to tip electrodes. This includes ring electrodes or pad electrodes. Ring electrodes are commonly used with a wide variety of abandoned implanted device leads including cardiac pacemakers, and neurostimulators, and the like. Pad electrodes are very common in neurostimulator applications. For example, spinal cord stimulators or deep brain stimulators can include a plurality of pad electrodes to make contact with nerve tissue. A good example of this also occurs in a cochlear implant. In a typical cochlear implant there would be sixteen pad electrodes placed up into the cochlea. Several of these pad electrodes make contact with auditory nerves.

Just variations in the pacemaker lead length and implant trajectory can significantly affect how much heat is generated. A paper entitled, HEATING AROUND INTRAVASCULAR GUIDEWIRES BY RESONATING RF WAVES by Konings, et al., journal of Magnetic Resonance Imaging, Issue 12:79-85 (2000), does an excellent job of explaining how the RF fields from MRI scanners can couple into implanted leads. The paper includes both a theoretical approach and actual temperature measurements. In a worst-case, they measured temperature rises of up to 74 degrees C. after 30 seconds of scanning exposure. The contents of this paper are incorporated herein by reference.

The effect of an MRI system on the abandoned leads of pacemakers, ICDs, neurostimulators and the like, depends on various factors, including the strength of the static magnetic field, the pulse sequence, the strength of RF field, the anatomic region being imaged, and many other factors. Further complicating this is the fact that each patient's condition and physiology is different and each lead implant has a different length and/or implant trajectory in body tissues. Most experts still conclude that MRI for the pacemaker patient should not be considered safe.

It is well known that many of the undesirable effects in an abandoned implanted lead system from MRI and other medical diagnostic procedures are related to undesirable induced EMFs in the lead system and/or RF currents in its distal tip (or ring) electrodes. This can lead to overheating of body tissue at or adjacent to the distal tip.

Distal tip electrodes can be unipolar, bipolar and the like. It is very important that excessive current not flow at the interface between the lead distal tip electrode and body tissue. In a typical cardiac pacemaker, for example, the distal tip electrode can be passive or of a screw-in helix type as will be more fully described. In any event, it is very important that excessive RF current not flow at this junction between the distal tip electrode and for example, myocardial or nerve tissue. Excessive current at the distal electrode to tissue interface can cause excessive heating to the point where tissue ablation or even perforation can occur. This can be life threatening for cardiac patients. For neurostimulator patients, such as deep brain stimulator patients, thermal injury can cause permanent disability or even be life threatening. Similar issues exist for spinal cord stimulator patients, cochlear implant patients and the like.

A very important and life-threatening problem is to be able to control overheating of abandoned implanted leads during an MRI procedure. A novel and very effective approach to this is to first install parallel resonant inductor and capacitor bandstop filters at or near the distal electrode of implanted leads. For cardiac pacemaker, these are typically known as the tip and ring electrodes. One is referred to U.S. Pat. No. 7,363,090; US 2007/0112398 A1; US 2008/0071313 A1; US 2008/0049376 A1; US 2008/0024912 A1; US 2008/0132987 A1; and US 2008/0116997 A1, the contents of all of which are incorporated herein. Referring now to US 2007/0112398 A1, the invention therein relates generally to L-C bandstop filter assemblies, particularly of the type used in active implantable medical devices (AIMDs) such as cardiac pacemakers, cardioverter defibrillators, neurostimulators and the like, which raise the impedance of internal electronic or related wiring components of the medical device at selected frequencies in order to reduce or eliminate currents induced from undesirable electromagnetic interference (EMI) signals.

U.S. Pat. No. 7,363,090 and US 2007/0112398 A1 show resonant L-C bandstop filters placed at the distal tip and/or at various locations along the medical device leads or circuits. These L-C bandstop filters inhibit or prevent current from circulating at selected frequencies of the medical therapeutic device. For example, for an MRI system operating at 1.5 Tesla, the pulse RF frequency is 64 MHz, as described by the Lamour Equation for hydrogen. The L-C bandstop filter can be designed to resonate at or near 64 MHz and thus create a high impedance (ideally an open circuit) in the lead system at that selected frequency. For example, the L-C bandstop filter, when placed at the distal tip electrode of a pacemaker lead, will significantly reduce RF currents from flowing through the distal tip electrode and into body tissue. The L-C bandstop filter also reduces EMI from flowing in the leads of a pacemaker, for example, thereby providing added EMI protection to sensitive electronic circuits. In general, the problem associated with abandoned leads is minimized when there is a bandstop filter placed at or adjacent to its distal tip electrodes. However, experiments have shown that even when such a bandstop filter is present, if the AIMD is disconnected, distal tip heating can still occur. This is generally due to the fact that prior art EMI filters located in the AIMD shunt some of the MRI induced RF energy out of the leads to the generally conductive housing of the AIMD. In this case, the AIMD housing, such as the housing of a cardiac pacemaker, acts as an important energy dissipating surface (EDS surface). In general, when the housing of the AIMD acts as an EDS surface, it does not rise in temperature very much due to its very large surface area and energy dissipating surface. However, when the lead is abandoned, in other words, the AIMD is removed; the proximal end of the lead is now terminated either in body tissue or in an insulated abandoned lead cap. It no longer is associated with an EDS surface or even a means to couple or divert energy to an EDS surface. Accordingly, MRI induced RF energy reflects off this open circuit and goes right on back to the distal electrodes where it can bounce back and forth and cause overheating, even when a distal bandstop filter is present. It will be appreciated that all of the embodiments described therein are equally applicable to a wide range of other implantable and external medical devices, including deep brain stimulators, spinal cord stimulators, drug pumps, probes, catheters and the like.

Electrically engineering a capacitor in parallel with an inductor is known as a bandstop filter or tank circuit. It is also well known that when a near-ideal L-C bandstop filter is at its resonant frequency, it will present a very high impedance. Since MRI equipment produces very large RF pulsed fields operating at discrete frequencies, this is an ideal situation for a specific resonant bandstop filter. Bandstop filters are more efficient for eliminating one single frequency than broadband filters. Because the L-C bandstop filter is targeted at this one frequency, it can be much smaller and volumetrically efficient.

A major challenge for designing an L-C bandstop filter for human implant is that it must be very small in size, biocompatible, and highly reliable. Coaxial geometry is preferred. The reason that coaxial is preferred is that implanted leads are placed at locations in the human body primarily by one of two main methods. These include guide wire lead insertion. For example, in a cardiac pacemaker application, a pectoral pocket is created. Then, the physician makes a small incision between the ribs and accesses the subclavian vein. The pacemaker leads are stylus guided/routed down through this venous system through the superior vena cava, through the right atrium, through the tricuspid valve and into, for example, the right ventricle. Another primary method of implanting leads (particularly for neurostimulators) in the human body is by tunneling. In tunneling, a surgeon uses special tools to tunnel under the skin and through the muscle, for example, up through the neck to access the Vagus nerve or the deep brain. In both techniques, it is very important that the leads and their associated electrodes at the distal tips be very small. US 2007/0112398 A1 solves these issues by using very novel miniature coaxial or rectilinear capacitors that have been adapted with an inductance element to provide a parallel L-C bandstop filter circuit.

The value of the capacitance and the associated parallel inductor can be adjusted to achieve a specific resonant frequency (SRF). The bandstop filters described in US 2007/0112398 A1 can be adapted to a number of locations within the overall implantable medical device system. That is, the L-C bandstop filter can be incorporated at or near any part of the medical device implanted lead system or at or adjacent to the distal tip electrodes. In addition, the L-C bandstop filter can be placed anywhere along the implanted lead system.

The L-C bandstop filters are also designed to work in concert with an EMI filter which is typically used at the point of lead ingress and egress of the active implantable medical device. For example, see U.S. Pat. No. 5,333,095; U.S. Pat. No. 5,905,627; U.S. Pat. No. 5,896,627; and U.S. Pat. No. 6,765,779, the contents of all being incorporated herein by reference. All four of these documents describe low pass EMI filter circuits. Accordingly, the L-C bandstop filters, as described in U.S. Pat. No. 7,393,090, entitled BANDSTOP FILTER EMPLOYING A CAPACITOR AND INDUCTOR TANK CIRCUIT TO ENHANCE MRI COMPATIBILITY OF ACTIVE IMPLANTABLE MEDICAL DEVICES, are designed to be used in concert with these prior art low pass filters. However, when an AIMD lead is abandoned, the filter capacitors, as previously described, are no longer connected to the lead. Bandstop filters, in accordance with U.S. Patent Application Publication No. US2007/0112398 A1, work particularly well when the proximal lead is connected to a pacemaker or ICD that has a feedthrough capacitor EMI filter. When the AIMD is disconnected, there is no place for the energy to go at the proximal end. Accordingly, the energy is reflected back to the distal tip. Recent testing by the inventors demonstrates that in certain lead configurations, even with a bandstop filter present, excessive heating at the distal tip electrode can still occur.

When one performs MRI testing on an abandoned lead system, one first establishes a controlled measurement. That is, with worst-case MRI equipment settings and a worst-case location within the MRI bore, and a worst-case lead configuration, one can measure heating using fiber optic probes at the distal electrodes. Temperature rises of 30 to over 60 degrees C. have been documented. When one takes the same control lead and places miniature bandstop filters in accordance with U.S. Pat. No. 7,363,090 or US 2007/0112398 A1, one finds that substantially less MRI induced energy is directed to distal electrodes greatly reducing their tendency to overheat. In fact, in many measurements made by the inventors, temperature rises of over 30 degrees C. have been reduced to less than 3 degrees C. However, a secondary problem has been discovered. That is, the implanted lead acts very much as like a transmission line. When one creates a very high impedance at the distal electrode to tissue interface by installation of a resonant bandstop filter as described in U.S. Pat. No. 7,038,900 and as further described in US 2007/0112398 A1, there is created an almost open circuit which is the equivalent of an unterminated transmission line. This causes a reflection of MRI induced RF energy back towards the proximal end where the AIMD (for example, a pacemaker) would have been connected. However, for an abandoned lead, this creates an open circuit at the proximal end with no place for the energy to escape. Therefore, this energy can be reflected back and forth resulting in temperature rises along the lead and more particularly at the distal electrode to tissue interface. In order to completely control the induced energy in an abandoned implanted lead system, one must take a system approach. In particular, a methodology is needed whereby energy can be dissipated from the lead system at the proximal end in a way that does not cause overheating either at the distal electrode interface or at the proximal end cap. Maximizing energy transfer from an implanted lead is more thoroughly described in U.S. patent Ser. No. 12/686,137, the contents of which are incorporated herein by reference.

Accordingly, there is a need for controlling the induced energy in an implanted abandoned lead system. Moreover, there is a need for novel tuned RF diverting circuits coupled to one or more energy or heat dissipation surfaces associated with an abandoned lead cap, which are preferably frequency selective and are constructed of passive components. Such circuits are needed to prevent MRI induced energy from reaching the distal tip electrode or its interface with body tissue. By redirecting said energy to an energy dissipation surface distant from the distal electrodes, this minimizes or eliminates hazards associated with overheating of said lead and/or its distal electrodes during diagnostic procedures, such as MRI. For maximum RF energy transfer out of the lead, frequency selective diverter circuits are needed which decouple and transfer energy which is induced onto implanted leads from the MRI pulsed RF field to an energy dissipating surface associated with an abandoned lead cap. The present invention fulfills these needs and provides other related advantages.

SUMMARY OF THE INVENTION

The present invention resides in terminating abandoned AIMD leads which embodies a novel abandoned lead cap associated with an energy dissipating surface. In general, the abandoned lead cap includes an electrically conductive housing/electrode which works in combination with frequency selective circuits so that the housing of the abandoned lead cap works as an energy dissipating surface. The energy dissipating surface may be disposed within the blood flow of a patient or comprise a plurality of spaced-apart energy dissipating surfaces. The energy dissipating surface may also include one or more slots for reducing eddy current heating therein.

In an alternative embodiment, the impedance of the abandoned lead cap can be balanced to the implanted lead impedance such that maximum energy is dissipated within the abandoned lead cap itself. In this case, thermal energy can be dissipated inside the abandoned lead cap, which has a controlled thermal mass and a controlled rate of temperature rise.

The system for terminating an abandoned implanted lead to minimize heating in a high power electromagnetic field environment in accordance with the present invention, comprises: (1) an implanted abandoned lead having a proximal end and a distal end, and impedance characteristics at a selected RF frequency or RF frequency band; (2) an abandoned lead cap having an energy dissipating surface (EDS surface) which is associated with the proximal end of the implanted abandoned lead; and (3) an energy diversion circuit conductively coupling the implanted abandoned lead to the energy dissipating surface to facilitate transfer to the energy dissipating surface of high frequency energy induced on the implanted abandoned lead at the selected RF frequency or frequency band. The present invention includes methods of attachment to an abandoned lead that has been cut off as well as one which has a proximal connector that has been abandoned. Methods of conductively coupling the abandoned lead to its associated abandoned lead cap EDS surface include direct connections (short to EDS) or connections through frequency selective electronic component networks (frequency selective diverters).

The novel abandoned lead cap of the present invention works best when bandstop filters are installed at or near the distal electrode of an implanted lead, wherein the RF energy induced by the MRI pulse field is attenuated from flowing into body tissues and thereby being dissipated. However, when bandstop filters are used, that energy still resides in the lead system. In other words, by preventing this induced energy from flowing to sensitive tissues at distal electrode interfaces, a great deal has been accomplished; however, it is still important to carefully dissipate the remaining energy that's trapped in the lead system. For abandoned leads, the most efficient way to do this is to use the metallic housing of the novel abandoned lead cap of the present invention.

One type of frequency selective network is a feedthrough capacitor. However, to provide optimal decoupling, one has to refer to the maximum power transfer theorem. When one has an ideal source, consisting of a voltage source and a series impedance, this is known as a Thevenin Equivalent Circuit. It is well known in electrical engineering that to transfer maximum power to a load that the load impedance must be equal to the source impedance. If the source impedance is completely resistive, for example, 50 ohms, then to transfer maximum power, the load impedance would have to be 50 ohms. When the source impedance is reactive, then to transfer maximum power to another location, the load impedance should have the opposite sign of reactance and the same impedance and resistance. Referring to a typical implanted lead system, the implanted leads typically appear inductive. Accordingly, having a capacitive EDS diverter circuit associated with the abandoned lead cap, one has at least some cancellation of these imaginary impedance factors. In electrical engineering, the inductance of the lead would be denoted by $+j\omega L$. The impedance of the capacitor, on the other hand, is a $-j/\omega C$ term. In the present invention, it's important to know the approximate inductance property of the implanted abandoned lead system, so that an optimal value of capacitance of the novel abandoned lead cap can be selected such that the +J component is nearly or completely canceled by the appropriate -J component of the capacitor. Again, refer to the contents of U.S. patent Ser. No. 12/686,137, the contents of which are incorporated herein by reference, for a more complete description of impedance cancellation and Thevenin's maximum power transfer theorem in this application.

Another way to provide an RF short circuit to the metallic housing of the novel abandoned lead cap is to use what is known in the industry an L-C series trap filter. When an inductor and a capacitor appear in series, it will always be a single frequency at which the inductive reactance is equal and opposite to the capacitive reactance. At this point, the L-C trap filter is said to be in resonance. For an ideal trap filter (one containing zero resistance), at resonance, it would present a short circuit. U.S. Pat. No. 6,424,234 describes L-C trap filters (also known as notch filters). The '234 patent describes notch filters for a completely different purpose and application. FIG. 10 of U.S. Pat. No. 6,424,234 shows notch filter attenuation in the kilohertz frequency range. The reason for this was to provide some degree of attenuation against low frequency emitters, such as 58 kHz electronic article surveillance (store security) gates. These gates detect tags on commercial items (such as clothing) as an anti-theft detection system. However, in the present invention, L-C trap filters can be optimally tuned to dissipate the RF pulsed energy in an abandoned lead induced from the RF field of an MRI system. For example, for a 1.5 Tesla system, the L-C trap filter would be tuned at the Lamour frequency of 64 MHz.

The present invention additionally resides in an overall energy management system capable of controlling the energy induced in abandoned implanted leads from the RF pulsed field of MRI scanners. More particularly, the present invention resides in a tuned energy balanced system for minimizing heating of an abandoned implanted lead in a high power electromagnetic field environment. The tuned energy balanced system of the present invention comprises an abandoned implanted lead having impedance characteristics at a selected RF frequency or frequency band, an energy dissipating surface associated with the abandoned lead cap, and an energy diversion circuit conductively coupling the implanted lead to the energy dissipating surface of the abandoned lead cap. The energy diversion circuit comprises one or more passive electronic network components whose impedance characteristics can be partially tuned to the implanted lead's impedance characteristics, to facilitate transfer to the energy dissipating surface of high frequency energy induced on the implanted lead at the selected RF frequency or frequency band.

The high frequency energy may comprise an MRI frequency or a range of MRI frequencies selected from the group of frequencies associated with an MRI scanner. In a preferred embodiment, the energy diversion circuit has a reactance that is vectorially opposite to the characteristic reactance of the implanted lead. Moreover, the energy diversion circuit has a capacitive reactance generally equal and opposite to the characteristic inductive reactance of the implanted lead. Preferably, the capacitive reactance and the inductive reactance each have a resistor component.

The energy diversion circuit may comprise a low pass filter such as a capacitor, an L-C trap, an "n" element filter or an L-C bandstop filter. Moreover, the energy diversion circuit may comprise one or more series resonant LC trap filters.

An impeding circuit may be associated with the energy diversion circuit for raising the high-frequency impedance of the abandoned lead cap at selected frequency. The impeding circuit may comprise an inductor and/or a bandstop filter.

The energy dissipating surface may comprise convolutions, fins or a roughened surface for increasing the surface area thereof. The roughened surface may be formed through plasma or chemical etching, porous or fractal coatings or surfaces, whiskers, morphologically designed columbar structures, vapor, electron beam or sputter deposition of a high surface area energy conductive material, or carbon nanotubes.

The energy dissipating surface of the abandoned lead cap may comprise a material capable of being visualized during magnetic resonance scan. Further, the energy dissipating surface may include a biomimetic coating.

The energy diversion circuit of the abandoned lead cap may include at least one non-linear circuit element such as a transient voltage suppressor, a diode or a pin diode.

The energy diversion circuit of the abandoned lead cap may comprise a high pass filter which prevents low frequency gradient field-induced energy in the implanted lead or the leadwire from passing through the diversion circuit to the energy dissipating surface. A high pass filter may comprise a capacitor, a resistor in series with the capacitor, or an L-C trap filter.

The abandoned lead cap housing may include a set screw for locking the proximal end of the implanted abandoned lead within the conductive block. The set screw may include a spike, tip or piercing rug to facilitate conductive coupling of the proximal end of the implanted abandoned lead with the conductive block. Alternatively, the abandoned lead cap housing may include a threaded locking system for locking the proximal end of the implanted abandoned lead within the conductive block.

The abandoned lead cap of the present invention may also include an RFID tag associated therewith.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 2 is a diagrammatic view of a typical probe or catheter;

FIG. 3 is an electrical diagrammatic view of the interior of the prober or catheter of FIG. 2;

FIG. 4 is an electrical diagrammatic view of the structure shown in FIG. 3, with a general impedance element connected between leads;

FIG. 5 is an electrical diagrammatic view similar to FIG. 4, illustrating a capacitor representing a frequency dependent reactive element between the leads;

FIG. 6 is a view similar to FIG. 5, wherein the general reactance element has been replaced by a capacitor in series with an inductor;

FIG. 7 is a view similar to FIGS. 4-6, showing the addition of series frequency selective reactances;

FIG. 8 is similar to FIG. 3, showing a low frequency model of the catheter and associated leads described in FIG. 2;

FIG. 9 is a view similar to FIGS. 3-8, illustrating how the distal rings are electrically isolated at a high frequency;

FIG. 10 is a view similar to FIGS. 3-9, showing the addition of series inductor components added to the frequency selective elements 112;

FIG. 11 is similar to FIGS. 3-10, illustrating frequency selective elements which incorporate parallel resonant inductor and capacitor bandstop filters;

FIG. 69 is a perspective view of the proximal end of an IS-1 connector;

FIG. 70 an enlarged, partially fragmented perspective and cross-sectional end view taken along line 70-70 of FIG. 69;

FIG. 71 is a perspective view of an exemplary locking insert with spikes;

FIG. 72 is a cross-sectional view of an exemplary abandoned lead cap showing how the locking insert is utilized to hold a cut-off proximal lead in place and simultaneously make proper electrical connection with the energy dissipating surface;

DETAILED DESCRIPTION OF THE PREFERRED EMBODIMENTS

Figure 1:
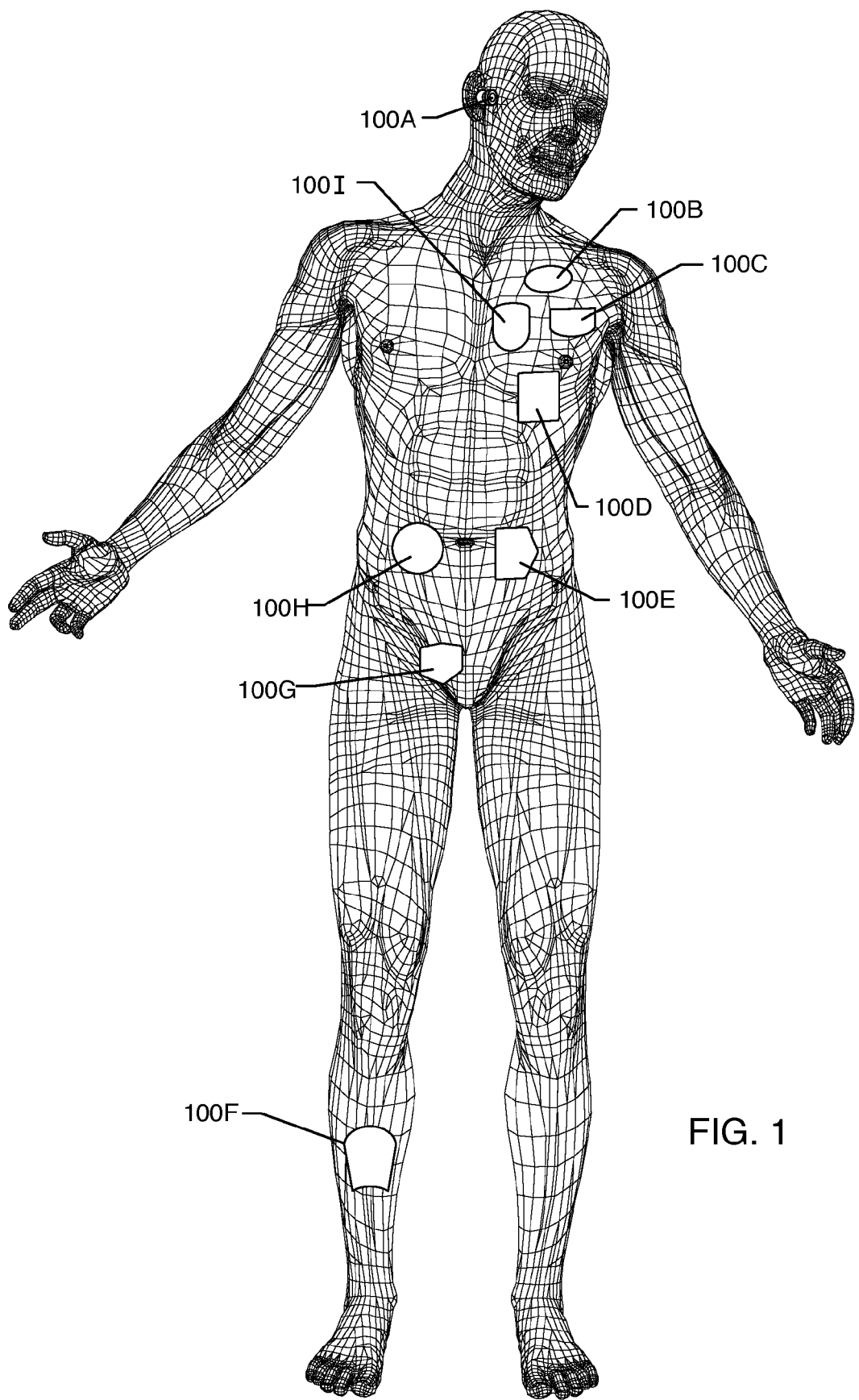
FIG. 1 is a wire-formed diagram of a generic human body showing a number of exemplary implanted medical devices.

As shown in the drawings for purposes of illustration, the present invention relates to a system for terminating abandoned implanted leads to minimize heating in high power electromagnetic field environments. In a broad sense, the present invention comprises an implanted abandoned lead having impedance characteristics at a selected RF frequency or frequency band, an energy dissipating surface associated with the abandoned lead, and an energy diversion circuit conductively coupling the abandoned lead to the energy dissipating surface. The energy diversion circuit may comprise one or more passive electronic network components whose impedance characteristics are at least partially tuned to the abandoned lead's impedance characteristics, to facilitate transfer to the energy dissipating surface of high frequency energy induced on the abandoned lead at the selected RF frequency or frequency band. Certain implanted leads may have a characteristic impedance that includes capacitive reactance. In this case the novel energy diversion circuit of the present invention would include inductive elements in order to cancel or partially cancel the capacitive reactance of the implanted lead.

The invention further resides in a combination of one or more bandstop filters placed at or near the distal electrode-to-tissue interface of an implanted abandoned lead, and a frequency selective diverter or diversion circuit which decouples energy induced on the implanted abandoned lead at a frequency or frequency band of an interest to an energy dissipating surface associated with the abandoned lead cap.

There are several reasons why implanted leads are abandoned, which include difficulty in removal, newer technologies and the like. However, a major reason that leads are often abandoned is due to insulation breakage, insulation resistance problems, or lead fractures. For example, when a cardiac pacemaker lead has an insulation defect or a lead fracture, it is often difficult or impossible to deliver therapy to the correct area in myocardial tissue. Stimulation of the pectoral muscle or phrenic nerve stimulation may also result. Such defective leads are often abandoned and replaced with a new lead in parallel. Exposure of the abandoned lead to high RF electromagnetic field environments, such as during MRI scans, cannot only cause overheating of distal electrodes, but also may result in excessive RF current flows in the area of defective insulation or a lead fracture. The abandoned lead cap is very useful in this regard in that by pulling energy out of the implanted lead and redirecting it to the EDS surface of the abandoned lead cap, one provides a high degree of protection. Accordingly, the present lead cap of the present invention not only protects a distal electrode to tissue interface, but also protects against other areas along the lead where RF leakage could occur.

In the case where bandstop filters are installed at or near the distal electrode of an implanted abandoned lead, the RF energy induced by the MRI pulse field is inhibited from flowing into body tissues and thereby being dissipated. However, even when distal electrode bandstop filters are used, that energy still resides in the lead system. In other words, by preventing this induced energy from flowing to sensitive tissues at distal electrode interfaces, a great deal has been accomplished; however, it is still important to carefully dissipate the remaining energy that's trapped in the lead system.

In order to provide optimal decoupling of RF energy from an implanted lead to the energy dissipating surface of an abandoned lead cap, one should consider Thevenin's maximum power transfer theorem. When one has an ideal source, consisting of a voltage source and a series impedance, this is known as a Thevenin Equivalent Source Circuit. It is well known in electrical engineering that to transfer maximum power to a load that the load impedance must be equal to the source impedance. If the source impedance is completely resistive, for example, 50 ohms, then to transfer maximum power, the load impedance would have to be 50 ohms. When the source impedance is reactive, then to transfer maximum power to another location, the load impedance should have the opposite sign of reactance and the same impedance and resistance. Referring to a typical implanted lead system, the implanted leads typically appear inductive. Accordingly, having a capacitive energy diversion circuit within the abandoned lead cap to couple energy from the lead to the EDS surface, one has at least some cancellation of these imaginary impedance factors. In electrical engineering, the inductance of the lead would be denoted by $+j\omega L$. The impedance of the capacitor, on the other hand, is a $-j/\omega C$ term. In the present invention, it's important to know the inductance property of the implanted lead system, so that an optimal value of capacitance between the EDS surface and ground can be selected such that the +J component is nearly or completely canceled by the appropriate −J component of the capacitor.

For maximal MRI energy dissipation from the lead system, one would want the capacitive reactance value to be equal and opposite in value to the inductive reactance of the lead system.

One does not have to exactly match the impedances of an implanted abandoned lead system to the diverter circuits of the present invention. Implanted leads usually tend to be inductive, although in certain cases they can even be capacitive. What is important is that the diverter circuit has a reactance which is vectorially opposite to the characteristic reactance of the implanted lead. In other words, if the implanted lead is inductive, it will have a $+j\omega L$ inductive reactance in ohms. One would balance this with a $-j/\omega C$ capacitive reactance in the diverter circuit. In an ideal case, the reactance of the diverter circuit would be generally equal and opposite to the characteristic reactance of the implanted lead. In an absolutely ideal situation, the implanted lead would have a characteristic inductive reactance and the diverter circuit would have an equal but opposite vector quantity capacitive reactance which would cancel. In order to obtain optimal energy transfer to an EDS surface in this case, it would further enhance energy transfer if the diverter circuit also had a resistive value that is equal to the characteristic resistance of the implanted lead. Fortunately, particularly when used in combination with a bandstop filter, it is not essential that the impedance or reactance of the diversion circuit be completely equal and opposite to the impedance or reactance of the implanted lead system.

The present invention is ideal for claiming MRI compatibility for a range of abandoned implanted leads. Using a cardiac pacemaker as an example, one may either through measurement or modeling characterize the impedance of leads of various lengths, such as 35 to 55 centimeters, and also analyze their characteristic impedance over various implant anatomical geometries. One could then determine an average impedance or reactance of this range of leads in order to design an averaged or optimized diverter circuit. Unlike for bandstop filters, the diverter circuit will generally work over a broad range of circuits, not just a single frequency. Accordingly, by using a properly tuned diverter circuit coupled to an energy dissipation surface of the abandoned lead cap of present invention, one would be able to assure that a range of lead lengths, lead types and implant geometries will all be safe in a high electric magnetic field environment such as MRI.

In a first order approximation, the energy diversion circuit of the present invention can simply be a short circuit or a resistor which is attached to the characteristic resistance of the average of the implanted leads for which one claims compliance. For example, if the implanted leads generally have a resistance value of around 80 ohms, then one could achieve a very high degree of tuned energy balance by having an 80 ohm resistor coupled between the lead and the energy dissipating surface. This would not cancel the reactance of the abandoned lead system but would still go a long way to remove energy from the leads and transfer it to the EDS surface of the abandoned lead cap.

The present invention also includes frequency selective diversion (decoupling) circuits which transfer RF energy which is induced onto implanted abandoned leads from a high power electromagnetic field environment such as an MRI RF field to an energy dissipating surface (EDS surface).

The present invention is primarily directed to the MRI pulsed RF field although it also has applicability to the gradient field as well. Because of the presence of the powerful static field, non-ferromagnetic components are used throughout the present invention. The use of ferromagnetic components is contraindicative because they have a tendency to saturate or change properties in the presence of the main static field.

FIG. 1 illustrates various types of active implantable medical devices referred to generally by the reference numeral 100 that are currently in use. FIG. 1 is a wire formed diagram of a generic human body showing a number of exemplary implanted medical devices. 100A is a family of implantable hearing devices which can include the group of cochlear implants, piezoelectric sound bridge transducers and the like.

100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted leadwires. 100F includes a variety of implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillator (ICD) devices and also includes the family of congestive heart failure devices (CHF). This is also known in the art as cardio resynchronization therapy devices, otherwise known as CRT devices.

Referring to U.S. 2003/0050557, Paragraphs 79 through 82, the contents of which are incorporated herein, metallic structures, particularly leads, are described that when placed in MRI scanners, can pick up high electrical fields which results in local tissue heating. This heating tends to be most concentrated at the ends of the electrical structure (either at the proximal or distal lead ends). This safety issue can be addressed using the disclosed systems and methods of the present invention. A significant concern is that the distal electrodes, which are in contact with body tissue, can cause local tissue burns.

As used herein, the lead means an implanted lead, including its electrodes that are in contact with body tissue. In general, for an AIMD, the term lead means the lead that is outside of the abandoned lead cap housing and is implanted or directed into body tissues. The term leadwire as used herein, refers to the wiring that is generally inside of the abandoned lead cap generally to its EDS surface, circuit board, substrates or internal circuitry. FIGS. 1A through 1G in U.S. 2003/0050557 have been redrawn herein as FIGS. 2 through 11 and are described as follows in light of the present invention.

FIG. 2 is a diagrammatic view of a typical prior art device 102 such as a probe, catheter or AIMD lead distal electrode. There are two leads 104 and 106 which thread through the center of the illustrative probe, catheter or AIMD lead 102 and terminate respectively in a corresponding pair of distal conductive electrode rings 108 and 110. Leads 104 and 106 are electrically insulated from each other and also electrically insulated from any metallic structures located within the catheter or lead body. The overall catheter or implanted lead body is generally flexible and is made of biocompatible materials, which also have specific thermal properties.

FIG. 3 shows the interior taken from FIG. 2 showing leads 104 and 106 which are routed to the two distal electrodes 108 and 110 as previously described in FIG. 2.

FIG. 4 shows the electrical circuit of FIG. 3 with a general frequency selective reactive diverting element 112 connected between leads 104 and 106. In the present invention, the diverting element 112 can consist of a number of frequency selective elements as will be further described. In general, the first conductive lead 104 is electrically coupled to the first electrode 108, the second conductive lead 106 is electrically coupled to the second electrode 110, and the frequency dependent reactive diverting element 112 electrically couples the first and second leads 104 and 106 such that high frequency energy is conducted between the first lead 104 and the second lead 106.

Referring once again to FIG. 4, the frequency selective reactive diverting element 112 tends to be electrically invisible (i.e., a very high impedance) at selected frequencies. The reactive element is desirably selective such that it would not attenuate, for example, low frequency biological signals or RF ablation pulses. However, for high frequency MRI RF pulsed frequencies (such as 64 MHz), this frequency reactive diverting element 112 would look more like a short circuit. This would have the effect of sending the energy induced into the leads 104 and 106 by the MRI RF field back into the catheter body energy dissipating surface into which the leads are embedded. In other words, there are desirably both RF energy and thermal conductivity to the probe or catheter body or sheath or shield which becomes an energy dissipating surface all along the lengths of leads 104 and 106 such that MRI induced energy that is present in these leads is diverted and converted to heat into the interior and along the catheter body itself. This prevents the heat build up at the extremely sensitive locations right at the ring electrodes 108 and 110 which are in intimate and direct contact with body tissue. In addition, the amount of temperature rise is very small (just a few degrees) because of the energy being dissipated over such a relatively high surface area. As previously mentioned, the high frequency RF pulsed energy from an MRI system can couple to implanted leads. This creates electromagnetic forces (EMFs) which can result in current flowing through the interface between electrodes that are in contact with body tissue. If this current reaches sufficient amplitude, body tissue could be damaged by excessive RF current flow or heat build-up. In certain situations, this can be life threatening for the patient.

FIG. 5 shows a capacitor 114 which represents one form of the frequency selective diverting reactive element 112. In this case, the reactive element 112 comprises a simple capacitor 114 connected between the first conductor or lead 104 and the second conductor or lead 106 and will have a variable impedance vs. frequency. The following formula is well known in the art: $X_C=1/(2\pi f c)$. Referring to the foregoing equation, one can see that since frequency (f) is in the denominator, as the frequency increases, the capacitive reactance in ohms decreases. With a large number in the denominator, such as the RF pulsed frequency of a 1.5 Tesla MRI system, which is 64 MHz, the capacitive reactance drops to a very low number (essentially a short circuit). By shorting the leads together at this one frequency, this diverts and prevents the RF energy from reaching the distal ring electrodes 108 and 110 and being undesirably dissipated as heat into body tissue. Referring once again to FIG. 4, one can see that the frequency selective diverting element 112 thereby diverts the high frequency RF energy back into the leads 104 and 106. By spreading this energy along the length of leads 104 and 106, it is converted to heat, which is dissipated into the main body of the probe, catheter or energy dissipating sheath. In this way, the relatively large thermal mass of the probe or catheter becomes an energy dissipating surface and any temperature rise is just a few degrees C. In general, a few degrees of temperature rise is not harmful to body tissue. In order to cause permanent damage to body tissue, such as an ablation scar, it generally requires temperatures above 20° C. The abandoned lead cap of the present invention works in identical manner by diverting energy away from the implanted lead and its associated distal electrodes to an energy dissipating surface that is associated with the abandoned lead cap. In a preferred embodiment, diverting circuitry contained within the abandoned lead cap, as described in FIGS. 3 to 11, is utilized to optimize energy transfer from the lead to the EDS surface. In summary, the frequency selective reactive element 112, which may comprise a capacitor 114 as shown in FIG. 5, forms a diversion circuit such that high frequency energy is diverted away from the distal electrodes 108 and 110 along the leads 104 and 106 to a surface that is distant from the electrodes 108 and 110, at which point the energy is converted to heat.

FIG. 6 describes a different way of diverting high frequency energy away from the electrodes 108, 110 and accomplishing the same objective. The general diverting reactance element 112 described in FIG. 4 is shown in FIG. 6 to comprise a capacitor 114 in series with an inductor 116 to form an L-C trap circuit. For the L-C trap, there is a particular frequency ($f_r$) at which the capacitive reactance $X_C$ and the inductive reactance $X_L$ are vectorally equal and opposite and tend to cancel each other out. If there are no losses in such a system, this results in a perfect short circuit between leads 104 and 106 at the resonant frequency. The frequency of resonance of the trap filter is given by the equation $$f_r = \frac{1}{2\pi\sqrt{LC}},$$

wherein $f_r$ is the frequency of resonance in Hertz, L is the inductance in henries, and C is the capacitance in farads.

FIG. 7 illustrates any of the aforementioned frequency dependent diverting impedance elements 112 with the addition of series frequency selective impeding reactances 118 and 120. The addition of series impedance further impedes or blocks the flow of high frequency MRI induced currents to the ring electrodes 108 and 110 as will be more fully described in the following drawings.

FIG. 8 is the low frequency model of FIG. 4, 5 or 6. In this regard, FIG. 8 is identical to FIG. 3, in that once again it shows the electrical leads 104 and 106 connected to the distal ring electrodes 108 and 110 of the probe or catheter 102. In the low frequency model, the frequency reactive diverting impedance elements 112 disappear because at low frequency their impedances approach infinity. Of course, elongated leads in a probe or catheter are electrically and functionally equivalent to leads used for cardiac pacemakers, implantable cardioverter defibrillators, neurostimulators and the like. For example, reference is made to U.S. Pat. No. 7,363,090, the contents of which are incorporated herein. Accordingly, any discussion herein related to probes or catheters apply equally to leads for all active implantable medical devices as described in FIG. 1, and vice versa. Referring once again to FIG. 8, this is also the low frequency model of the circuits shown in FIG. 7. At low frequency, the frequency selective or reactive diverting component 112 tends to look like a very high or infinite impedance. At low frequency, the series reactive or frequency variable impeding elements 118 and 120 tend to look like a very low impedance or short circuit. Accordingly, they all tend to disappear as shown in FIG. 8.

FIG. 9 is a high frequency model that illustrates how the distal electrodes or rings 108 and 110 are electrically isolated at high frequency by shorting leads 104 and 106 at location 122. As previously mentioned, such shorting or current diverting could be accomplished by a direct short, a capacitor, a capacitive low pass filter or a series resonant L-C trap circuit. FIG. 9 also shows the electrodes 108 and 110 as cut or disconnected and electrically isolated from the rest of the circuit. This is because at very high frequency series impeding elements 118 and 120 tend to look like a very high impedance or an open circuit. In summary, by reactive elements 112, 118 and 120 acting cooperatively, reactive element 112 diverts the high frequency energy back into energy dissipating surfaces in the probe or catheter while at the same time reactive elements 118 and 120 impede the high frequency RF energy. Accordingly, in the ideal case, at high frequencies, the equivalent circuit of FIG. 9 is achieved. Accordingly, excessive high frequency MRI RF energy cannot reach the distal ring electrodes 108, 110 and cause undesirable heating at that critical tissue interface location.

FIG. 10 shows any of the previously described diverting frequency selective impedance elements 112 in combination with series reactance components shown in the form of a pair of inductors 116a, 116b. It is well known to electrical engineers that the inductive reactance in ohms is given by the equation $X_L = 2\pi fL$. In this case the frequency term (f) is in the numerator. Accordingly, as the frequency increases, the reactance (ohms) of the inductors also increases. When the frequency is very high (such as 64 MHz) then the reactance in ohms becomes extremely high (ideally approaches infinity and cuts off the electrodes). By having a short circuit or very low impedance between the leads 104 and 106, and the probe/catheter body and then, at the same time, having a very high impedance in series with the electrodes from inductors 116, this provides a very high degree of attenuation to MRI RF pulsed frequencies thereby preventing such energy from reaching the distal ring electrodes 108 and 110. In FIG. 10, the line-to-line selective impedance element 112 diverts high frequency energy back into leads 104 and 106 while at the same time the series inductors 116 impede (or cut-off) high frequency energy. When the line-to-line element 112 is a capacitor 114 as shown in FIG. 5, then this forms what is known in the prior art as an L section low pass filter, wherein the capacitor 114 electrically cooperates with the inductors 116 (FIG. 10) to form a 2-element low pass filter. It will be obvious to those skilled in the art that FIG. 5 describes a single element (capacitor) low pass filter, and that FIG. 10 describes a 2-element or L-section low pass filter. Moreover, any number of inductor and capacitor combinations can be used for low pass filters, including 3-element Pi or T circuits, LL, 5-element or even "n" element filters.

FIG. 11 offers an even greater performance improvement over that previously described in FIG. 10. In FIG. 11, modified frequency selective impeding elements each incorporate a parallel resonant inductor 116 and capacitor 114 which is also known in the industry as a bandstop filter 123. The L-C components for each of the reactive elements are carefully chosen such that each of the bandstop filters 123 is resonant, for example, at the pulsed resonant frequency of an MRI scanner. For common hydrogen scanners, the pulsed resonant frequency of an MR scanner is given by the Lamor equation wherein the RF pulsed frequency in megahertz is equal to 42.56 times the static field strength. For example, for a popular 1.5 Tesla scanner, the RF pulsed frequency is 64 MHz. Common MR scanners that are either in use or in development today along with their RF pulsed frequencies include: 0.5 Tesla-21 MHz; 1.5 Tesla-64 MHz; 3 Tesla-128 MHz; 4 Tesla-170 MHz; 5 Tesla-213 MHz; 7 Tesla-300 MHz; 8 Tesla-340 MHz; and 9.4 Tesla-400 MHz. When the bandstop filters 123 are resonant at any one of these RF pulsed frequencies, then these elements tend to look like an open circuit which impedes the flow of RF current to distal electrodes. When compatibility with different types of MR scanners is required, for example, 1.5, 3 and 5 Tesla, then three separate bandstop filter elements in series may comprise the reactive element 118 (FIG. 7), and three separate bandstop filter elements in series may comprise the reactive element 120 (FIG. 7). Each of these would have their L and C components carefully selected so that they would be resonant at different frequencies. For example, in the case of MR scanners operating at 1.5, 3 and 5 Tesla, the three bandstop filters comprising the reactive element 118 as well as the three bandstop filters comprising the reactive element 120 would be resonant respectively at 64 MHz, at 128 MHz, and at 170 MHz. The resonant frequencies of the bandstop filter elements could also be selected such that they are resonant at the operating frequency of other emitters that the patient may encounter such as diathermy and the like. The use of bandstop filters 123 is more thoroughly described in U.S. Pat. No. 7,363,090; US 2007/0112398 A1; US 2007/0288058; US 2008/0071313 A1; US 2008/0049376 A1; US 2008/0161886 A1; US 2008/0132987 A1 and US 2008/0116997 A1, the contents of which are incorporated herein.

Figure 12:
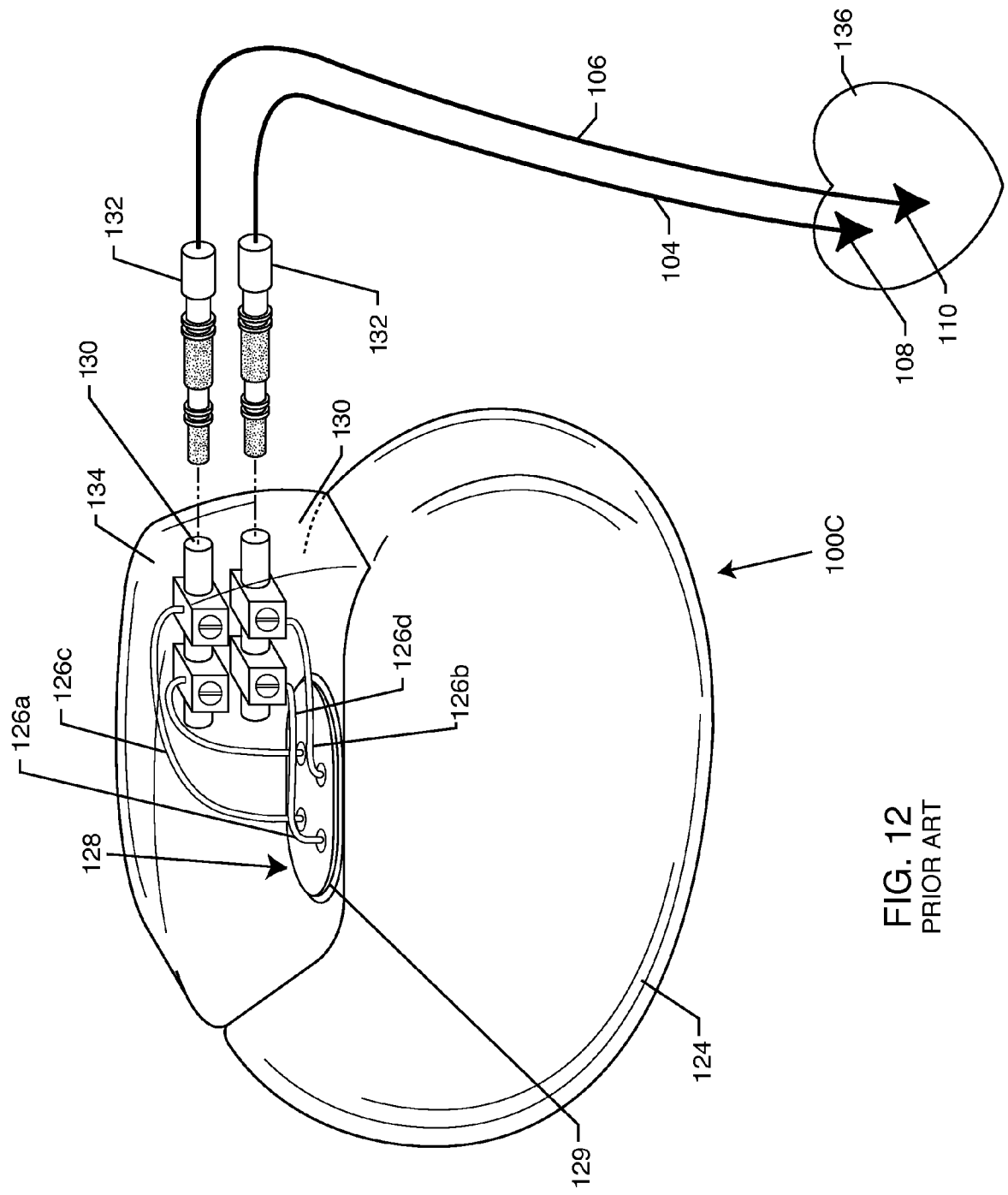
FIG. 12 is a perspective and somewhat schematic view of a prior art active implantable medical device (AIMD) including a pair of leads directed to the heart of a patient.

Referring now to FIG. 12, a prior art active implantable medical device (AIMD) 100 is illustrated. In general, the AIMD 100 could, for example, be a cardiac pacemaker 100C which is enclosed by a titanium or stainless steel conductive housing 124. The conductive housing 124 is hermetically sealed and contains a battery and electronic circuits, however, there is a point where conductors 126a, 126b, 126c and 126d must ingress and egress in non-conductive relationship relative to the housing 124. This is accomplished by providing a hermetic terminal assembly 128. Hermetic terminal assemblies 128 are well known and generally consist of a ferrule 129 which is laser welded to the titanium housing 124 of the AIMD 100C. In FIG. 12, four conductive leadwires 126a-126d are shown for connection to a corresponding number of leads, such as the illustrative bipolar leads 104 and 106 shown for coupling to the connector receptacles 130. In this configuration, the four leads coupled respectively to the conductors 126a-126d comprise a typical dual chamber bipolar cardiac pacemaker. It should be noted that each of the bipolar leads 104 and 106 have a pair of leads associated with them. These are known as bipolar electrodes wherein one wire is routed to the tip electrode and the other is routed to the ring electrode in locations 108 and 110.

Connectors 132 are commonly known as IS-1 connectors and are designed to plug into mating receptacles 130 on a header block 134 mounted on the pacemaker housing 124. These are low voltage (pacemaker) lead connectors covered by an International Standards Organization (ISO) standard IS-1. Higher voltage devices, such as implantable cardioverter defibrillators, are covered by a standard known as the ISO DF-1. A newer standard had been published that integrates both high voltage and low voltage connectors into a new miniature quadpolar connector series known as the ISO IS-4 standard. Leads plugged into these connectors are typically routed in a pacemaker or ICD application into the right ventricle and right atrium of the heart 136.

In the following description, functionally equivalent elements shown in various embodiments will often be referred to utilizing the same reference number.

Referring once again to the prior art AIMD 100, such as the cardiac pacemaker 100C in FIG. 12, generally such AIMDs have primary batteries that have a limited lifetime. It is very common in the art, since the AIMD is laser welded and hermetically sealed, that when battery replacement is due, the entire AIMD is replaced. If there is nothing wrong with the implanted leads 104 and 106, they are generally reused. However, in many cases, there are lead defects, poor impedance characteristics, or even abrasions in a lead that cause the physician to abandon them and instead, insert new leads. It is a relatively easy matter to insert new leads endocardially in parallel with the existing leads. These new leads are then connected to a new AIMD, such as a new cardiac pacemaker. Accordingly, the previous leads are left in the body, which will be shown, are problematic for MRI.

Figure 13:
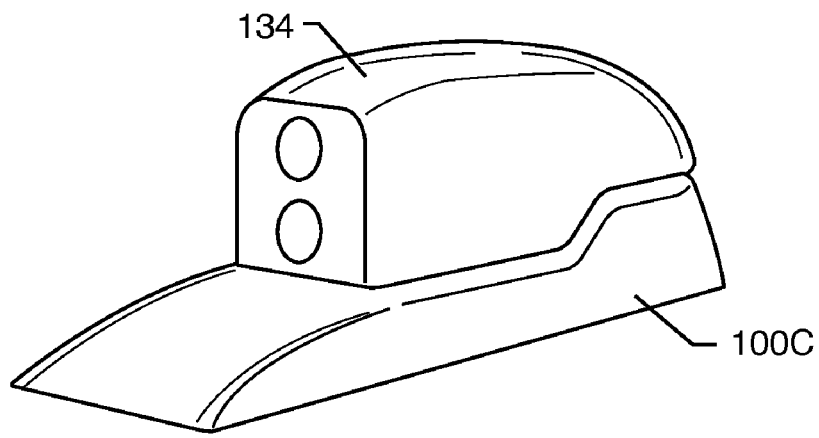
FIG. 13 is a perspective view of a dual chamber IS-1 header block.

FIG. 13 illustrates a typical dual chamber IS-1 header block 134 which is attached to a partial cutaway view of a prior art cardiac pacemaker 100C.

Figure 14:
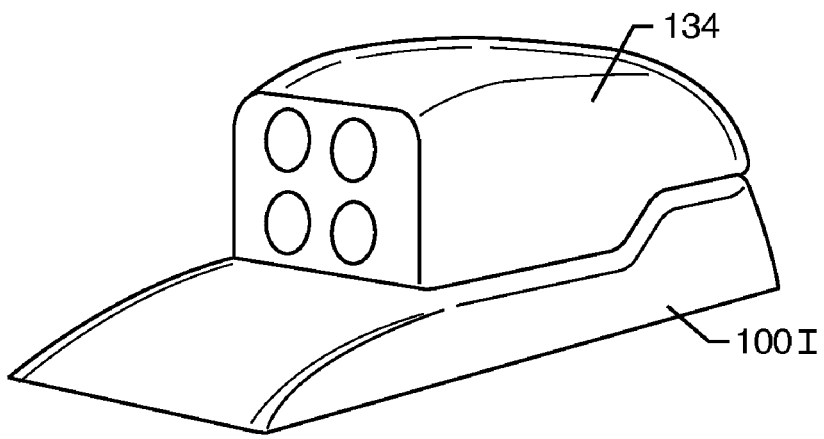
FIG. 14 is a perspective view of a four chamber header block.

FIG. 14 is an alternative AIMD header block 134 which illustrates four connector ports. This header block is attached to a partial cutaway view of a prior art implantable cardioverter defibrillator (ICD) 100I.

Figure 15:
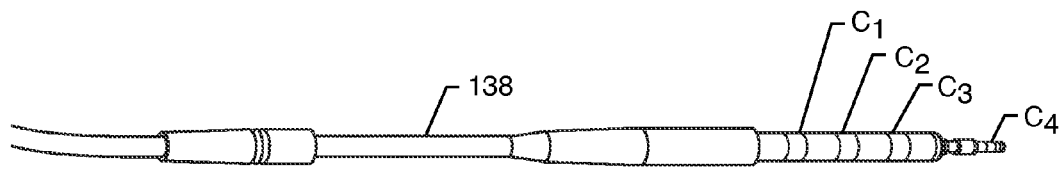
FIG. 15 is a perspective view of an inline quadpolar IS-4 lead.

FIG. 15 illustrates a drawing of the new inline quadripolar IS-4 (138) lead with four electrodes $C_1$ through $C_4$ which incorporates both low voltage and high voltage circuits all in one.

Figure 16:
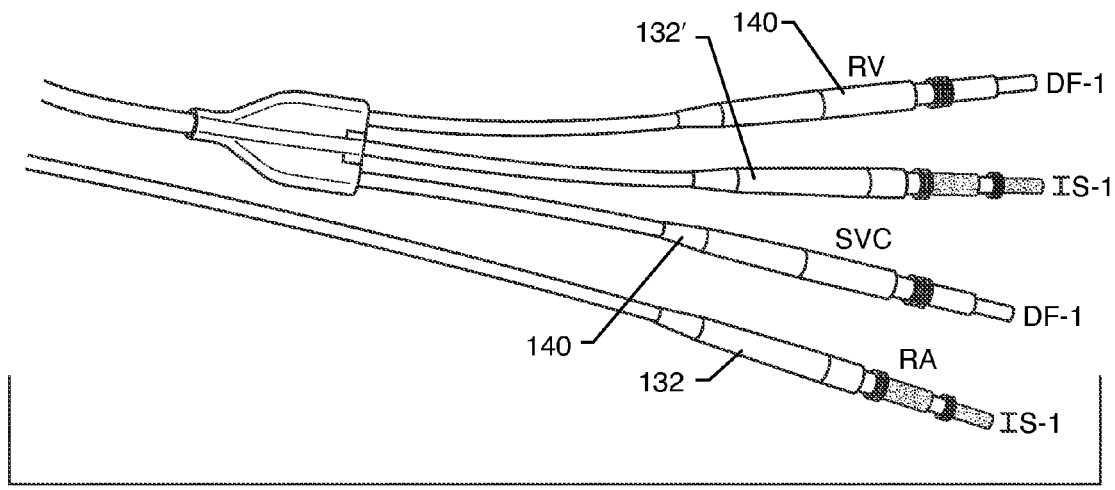
FIG. 16 is a perspective view of a typical lead system for an implantable cardioverter defibrillator.

FIG. 16 illustrates a typical lead system for an ICD. The leads of FIG. 16 are designed to match up with the header port 134 as shown in FIG. 14. Referring once again to FIG. 16, one can see that there are two low voltage IS-1 leads 132 and 132'. Typically, one of these would be routed to the right atrium and the other would be routed to the right ventricle. There are also two high voltage shocking leads DF-1 (140). Typically, one DF-1 electrode would be routed to the right ventricle and the other would be routed to the inside of the superior vena cava.

Figure 17:
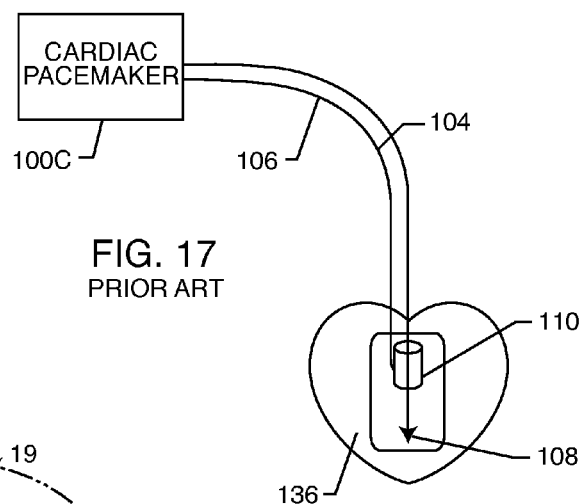
FIG. 17 is a schematic illustration of a bipolar lead system with a distal tip and ring typically as used with a cardiac pacemaker.

FIG. 17 illustrates a prior art single chamber bipolar AIMD 100C and leads 104 and 106 with a distal tip electrode 108 and a ring electrode 110 typically as used with a cardiac pacemaker 100C. Should the patient be exposed to the fields of an MRI scanner or other powerful emitter used during a medical diagnostic procedure, currents that are directly induced in the leads 104, 106 can cause heating by $I^2R$ losses in the leads or by heating caused by RF current flowing from the tip and ring electrodes 108, 110 into body tissue. If these induced RF currents become excessive, the associated heating can cause damage or even destructive ablation to body tissue 136.

Figure 18:
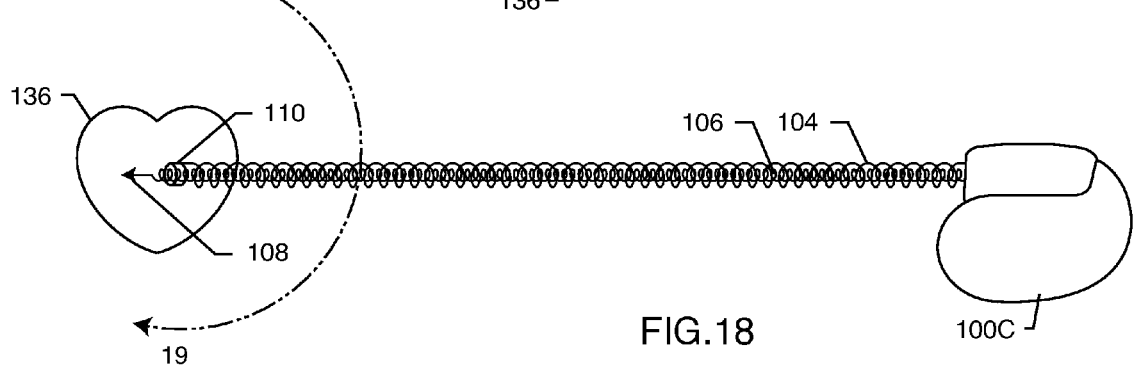
FIG. 18 is a schematic illustration of a prior art single chamber bipolar cardiac pacemaker lead showing the distal tip and the distal ring electrodes.

FIG. 18 illustrates a single chamber bipolar cardiac pacemaker 100C, and leads 104 and 106 having distal tip 138 and distal ring electrode 108. This is a spiral wound (coaxial) lead system where the tip electrode lead 104 is wrapped around the ring electrode lead 106. The characteristic impedance of this lead type usually has an inductive component. There are other types of pacemaker lead systems in which these two leads that lay parallel to one another (known as a bifilar lead system), which are not shown.

Figure 19:
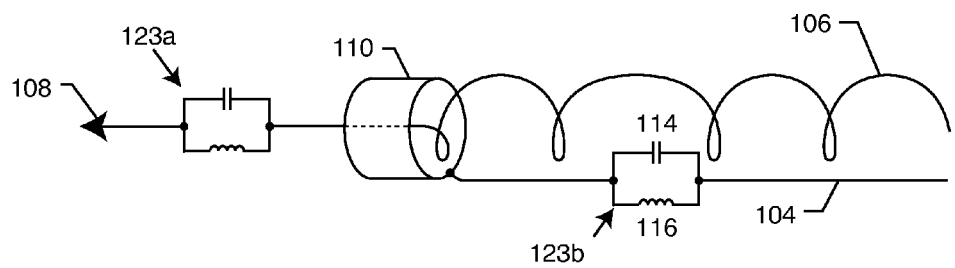
FIG. 19 is an enlarged, fragmented schematic view taken generally along the line 19-19 of FIG. 18, illustrating placement of bandstop filters adjacent to the distal tip and ring electrodes.

FIG. 19 is an enlarged schematic illustration of the area "19-19" in FIG. 18. In the area of the distal tip electrode 108 and the ring electrode 110, bandstop filters 123a, 123b have been placed in series with each of the respective ring and tip circuits. The ring circuit lead 104 has been drawn straight instead of coiled for simplicity. The bandstop filters 123 are tuned such that, at an MRI pulsed RF frequency, a high impedance will be presented thereby reducing or stopping the flow of undesirable MRI induced RF current from the electrodes 108 and 110 into body tissues.

Figure 20:
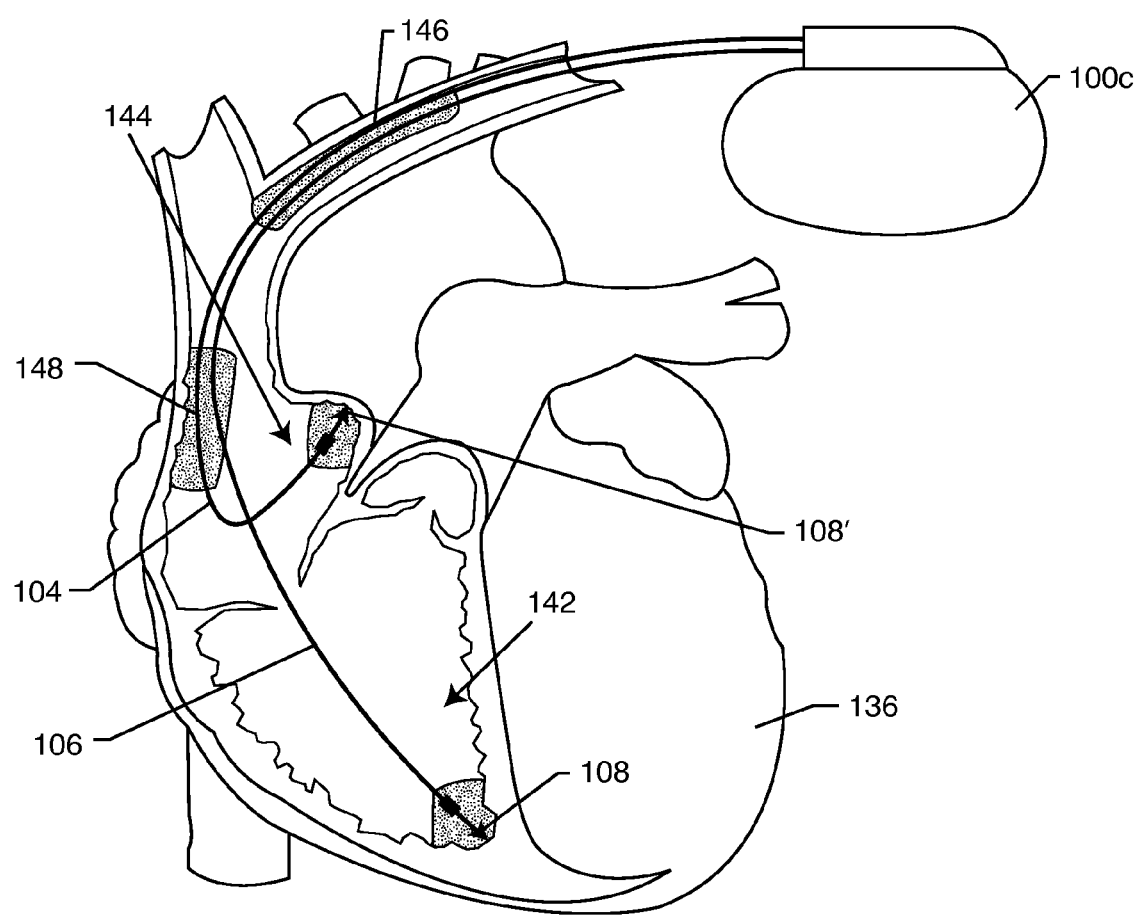
FIG. 20 is a line drawing of a human heart with cardiac pacemaker dual chamber bipolar leads shown in the right ventricle and the right atrium.

FIG. 20 is a line drawing of a human heart 136 with cardiac pacemaker dual chamber bipolar leads 104, 106 shown in the right ventricle 142 and the right atrium 144. FIG. 20 is taken from slide number 3 from a PowerPoint presentation given at The 28th Annual Scientific Sessions of the Heart Rhythm Society by Dr. Bruce L. Wilkoff, M. D. of the Cleveland Clinic Foundation. This article was given in Session 113 on Friday, May 11, 2007 and was entitled, ICD LEAD EXTRACTION OF INFECTED AND/OR REDUNDANT LEADS. These slides are incorporated herein by reference and will be referred to again simply as the Wilkoff reference. In FIG. 20, one can see multiple leads 104, 106 extending from an active implantable medical device 100C (such as a cardiac pacemaker or the like) coupled to associated electrodes, one of which comprises the distal tip ventricular electrode 108 located in the right ventricular 142 apex. The dark shaded areas in FIG. 20 show the experience of the Cleveland Clinic and Dr. Wilkoff (who is a specialist in lead extraction), where extreme tissue overgrowth and vegetation tends to occur. There are numerous cases of extracted leads where both the tip and ring electrodes have been overgrown and encapsulated by tissue. Referring once again to FIG. 20, one can see tip electrode 108, which is located in the right ventricular apex 142. The shaded area encasing this electrode 108 shows that this area tends to become encapsulated by body tissue. A distal tip electrode 108' in the right atrium 144 may similarly be overgrown and encapsulated by tissue, as shown by the encasing shaded area. There are other areas in the superior vena cava and venous system where leads tend to be encapsulated by body tissue a great percentage of the time. These are shown as areas 146 and 148.

Referring once again to FIG. 20, as previously mentioned, it is very important that if this lead system is abandoned that it not overheat during MRI procedures particularly at or near the distal tip and ring electrodes 108, 110. If either or both the distal tip and ring electrode become overgrown by body tissue, excessive overheating can cause scarring, burning or necrosis of said tissues. Often times when the device such as a pacemaker 100C shown in FIG. 20 is changed out, for example, due to low battery life and a new pacemaker is installed, the physician may decide to install new leads at the same time. Leads are also abandoned for other reasons, such as a dislodged or a high impedance threshold. Sometimes over the course of a patient life-time, the distal tip electrode-to-tissue interface increases in impedance. This means that the new pacemaker would have to pulse at a very high voltage output level which would quickly deplete its battery life. This is yet another example of why a physician would choose to insert new leads. Sometimes the old leads are simply extracted. However, this is a very complicated surgical procedure which does involve risks to the patient. Fortunately, there is plenty of room in the venous system and in the tricuspid valve to place additional leads through the same pathway. The physician may also choose to implant the pacemaker on the other side. For example, if the original pacemaker was in the right pectoral region, the physician may remove that pacemaker and choose to install the new pacemaker in the left pectoral region using a different part of the venous system to gain lead access. In either case, the abandoned leads can be very problematic during an MRI procedure.

In general, prior art abandoned leads are capped with a silicone cap at their proximal connector points so that body fluids will not enter into the lead system, cause infections and the like. However, it has been shown in the literature that the distal electrodes of abandoned leads are at high risk to heat up during MRI procedures. Accordingly, the abandoned lead cap of the present invention when associated with an energy dissipation surface is very useful when placed at or near the proximal electrical contact after a pacemaker is removed and its leads are disconnected (abandoned). Referring back to the article by Dr. Bruce Wilkoff, attention is drawn to slide number 2, which is an example of a lead extraction showing both a distal tip electrode and a distal ring which have been heavily overgrown and encapsulated by body tissue.

Figure 21:
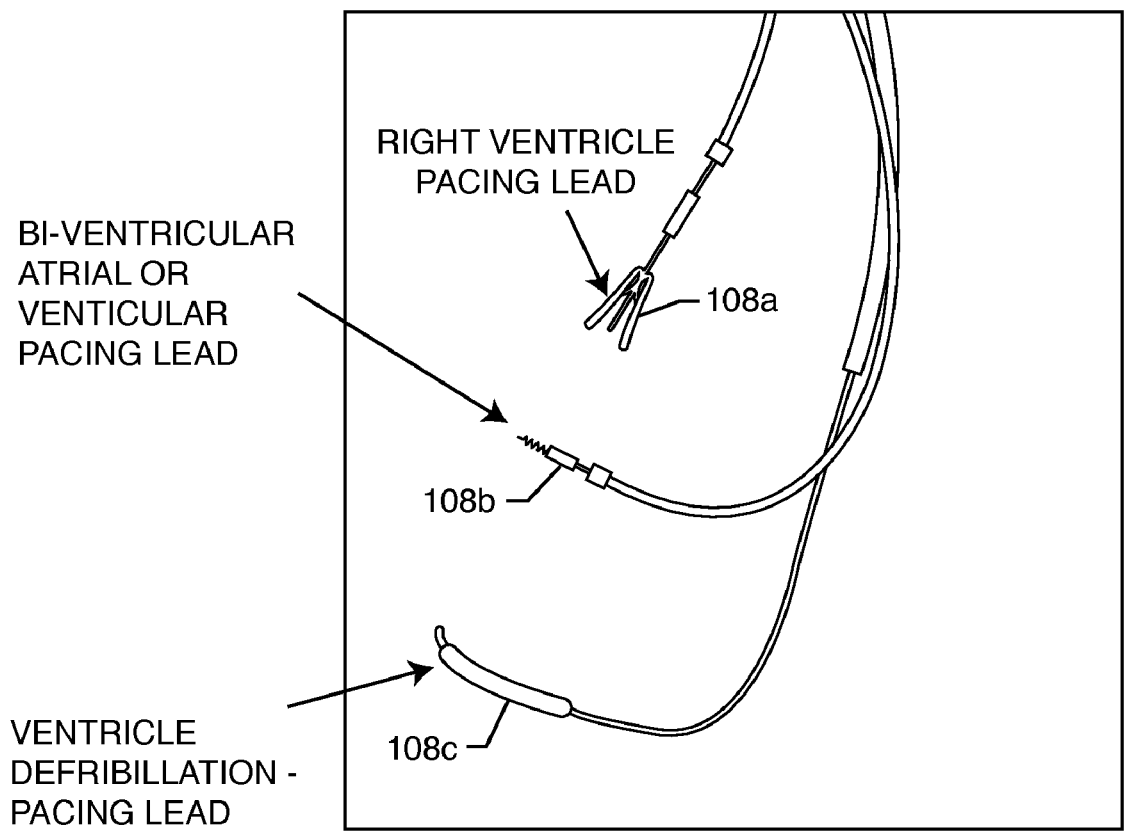
FIG. 21 is a line drawing of a exemplary lead systems with various types of electrode tips.

FIG. 21 is a line drawing showing lead systems with various types of electrode tips 108. For instance, electrode tip 108a is a passive fixation right atrium pacing lead, electrode tip 108b is an active fixation bi-ventricular pacing lead, and electrode tip 108c is a ventricle defibrillation lead.

If the leads and their associated electrodes as described in FIG. 21 were abandoned, it would be important that each of the leads be connected to an abandoned lead cap(s) that are associated with an energy dissipating surface. In a preferred embodiment, a passive component frequency selective diverter element would be used such that high frequency RF energy from the lead would be coupled to the EDS surface. The word passive is very important in this context. Active electronic circuits, which are defined as those that require power, do not operate very well under very high amplitude electromagnetic field conditions. Active electronic filters, which generally are made from microelectronic chips, have very low dynamic range. Extremely high fields inside an MRI chamber would tend to saturate such filters and make them become nonlinear and ineffective. Accordingly, frequency selective networks are preferably realized using non-ferromagnetic passive electronic components. In general, this means that the frequency selective components for both diverters and impeders preferably consist of capacitors, inductors, and resistors in various combinations. Passive electronic components are capable of handling very high power levels without changing their characteristics or saturating. Moreover, the inductor elements are preferably made from materials that are not ferromagnetic. The reason for this is that MRI machines have a very powerful main static magnetic field ($B_0$). This powerful static magnetic field tends to saturate ferrite elements and would thereby change dramatically the value of the inductance component. Accordingly, in the present invention, the inductor elements are preferably fabricated without the use of ferrites, nickel, iron, cobalt or other similar ferromagnetic materials that are commonly used in general electronic circuit applications. In accordance with the present invention, energy diversion circuits were previously shown in FIGS. 4, 5 and 6. Active electronic filters could also be used as diverter circuits, however, as previously mentioned, their dynamic range would be limited and they would tend not to work very well in the presence of very powerful RF fields.

Figure 22:
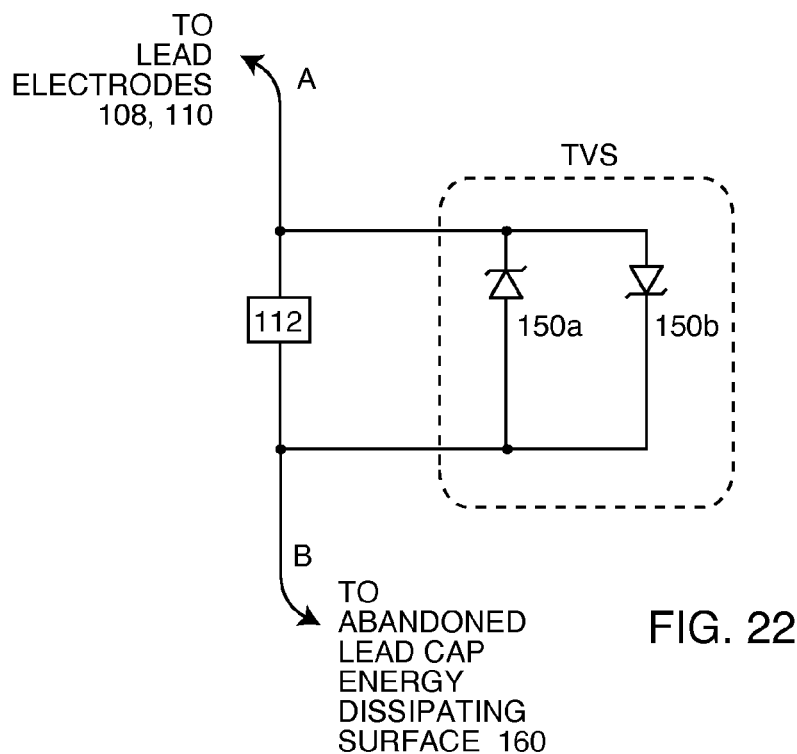
FIG. 22 is a schematic circuit diagram illustrating an exemplary energy diverter with non-linear circuit elements such as a pair of diodes in a parallel therewith.

FIG. 22 illustrates an exemplary energy diverter 112 (as previously shown described in connection with FIGS. 4, 5 and 6) comprising, for example, a capacitor 114 (as previously shown and described herein) with nonlinear circuit elements such as diodes 150a and 150b placed in parallel therewith. These diodes 150a, 150b are oriented in a back-to-back configuration. The diode elements 150a, 150b, as illustrated in FIG. 22, can be placed in parallel with each other, and with any of the frequency selective circuit elements shown in FIGS. 4 through 11. For example, referring to FIG. 5, the diode elements could be placed in parallel with the capacitive element 114. Referring to FIG. 10, two diode elements could also be placed in parallel with each of the inductor elements 116a and 116b. Back-to-back diodes are one form of a transient voltage suppressor 152.

Transient voltage suppressors (TVS) are well known in the prior art for providing over voltage circuit protection. They are sold under various trade names including the name Transorb. The diodes 150a, 150b can also be pin diodes. Since automatic external defibrillators (AEDs) have become very popular in the patient environment, the diverter circuits of abandoned lead caps 154 must be able to withstand very high pulsed currents. These pulse currents can range anywhere from 1 to 8 amps. The passive frequency selective components used in accordance with the present invention are typically very small in size. In order for an inductor element L to be able to handle 1 to 8 amps, it would have to be exceedingly large. However, by using physically small diode elements 150a and 150b, one can have the circuits switched to a different state. That is, when a high voltage, such as that from an AED appears, the diodes would forward bias thereby temporarily shorting out the diverter 112. Thereby the correspondingly high AED induced currents would be diverted away from the relatively sensitive (small) passive elements L (116) and C (114) of the diverter element 112 in such a way that they not be harmed.

Figure 23:
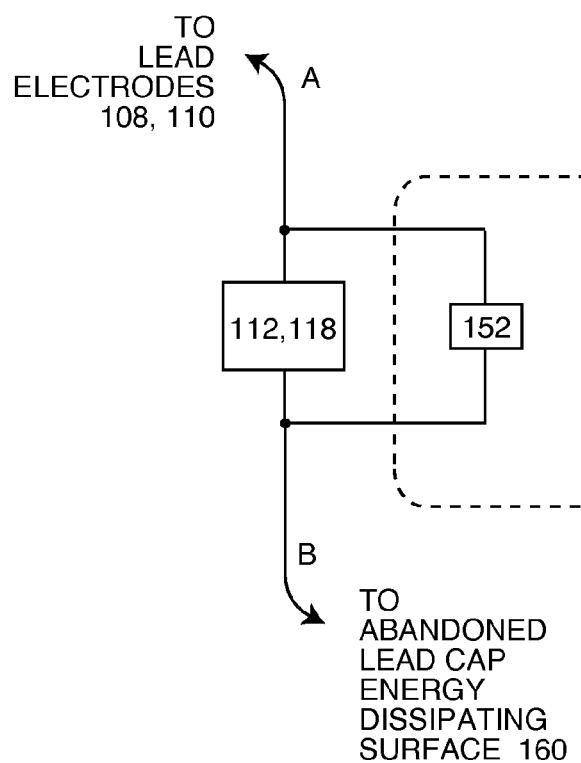
FIG. 23 is a view similar to FIG. 22, except showing that the diverter could also be an impeder element.

FIG. 23 is a schematic diagram that is very similar to FIG. 22 except that it shows that the diverter element 112 could also be an impeder element 118. In either case, a transient voltage suppressor (TVS) 152 is shown in parallel. The TVS is inclusive of the back-to-back diodes 150a and 150b previously illustrated in FIG. 22. The transient voltage suppressor 152 includes all types of transient voltage suppressors, diode arrays, Transorbs, etc.

Figure 24:
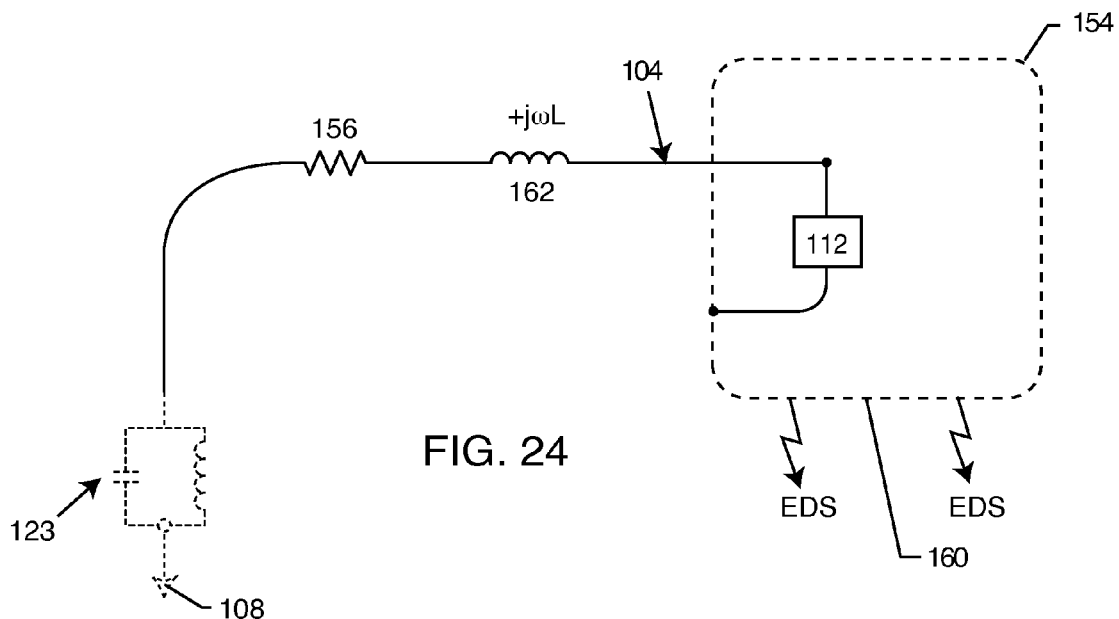
FIG. 24 is a schematic illustration of a unipolar lead system attached to an abandoned lead cap of the present invention.

FIG. 24 shows a unipolar lead system 104 attached to a novel abandoned lead cap 154 of the present invention. Associated with the abandoned lead cap 154 is an energy dissipating surface 160. Also shown is a frequency selective diverter circuit 112 which is connected between the lead 104 and the EDS surface 160. A unipolar lead system is shown for simplicity. It will be obvious to those skilled in the art that any number of lead wires 104 could be used. In FIG. 20, one will see that this system involves an AIMD 100C attached to bipolar leads 104, 106 to a human heart 136. At the distal tip or distal end of lead wire 104, 106 is an optional bandstop filter 123 as illustrated in FIGS. 11 and 19. The optional bandstop filter 123, which is usually located at or near the distal electrode 108, is more thoroughly described in U.S. Pat. No. 7,363,090 the contents of which are incorporated herein. As shown, the implanted lead has inductive 162 and resistive 156 properties along its length (it may also have capacitive properties as well). The total or equivalent inductive reactance of the lead in ohms is given by the formula $+j\omega L$. As mentioned, a distal electrode bandstop filter 123 may or may not be present. The equivalent inductance 162 and resistance 156 of the lead system also includes the impedance of any tissue return path. It should be noted that the present invention applies to any type of abandoned AIMD lead. For example, there are certain neurostimulator applications involving a number of distal electrodes that all have return paths through body tissue from a distal electrode 108 all the way to the abandoned lead cap. One of the best ways to actually determine the characteristic lead impedance, including its inductive 162, capacitive, and resistive 156 properties, is through human body modeling using software such as SAMCAD. Using SAMCAD, one can calculate the electric field vectors all along the lead trajectory. One can then calculate the induced energy into the implanted leads and their characteristic impedances. Referring once again to FIG. 24 one can see that on the interior of the abandoned lead cap 154 there are frequency selective components 112. These frequency selective elements 112 can consist of various arrangements of capacitors 114, inductors 116 and resistors 158 or even short circuits as will be more fully described in FIGS. 25 through 34.

Figure 25:
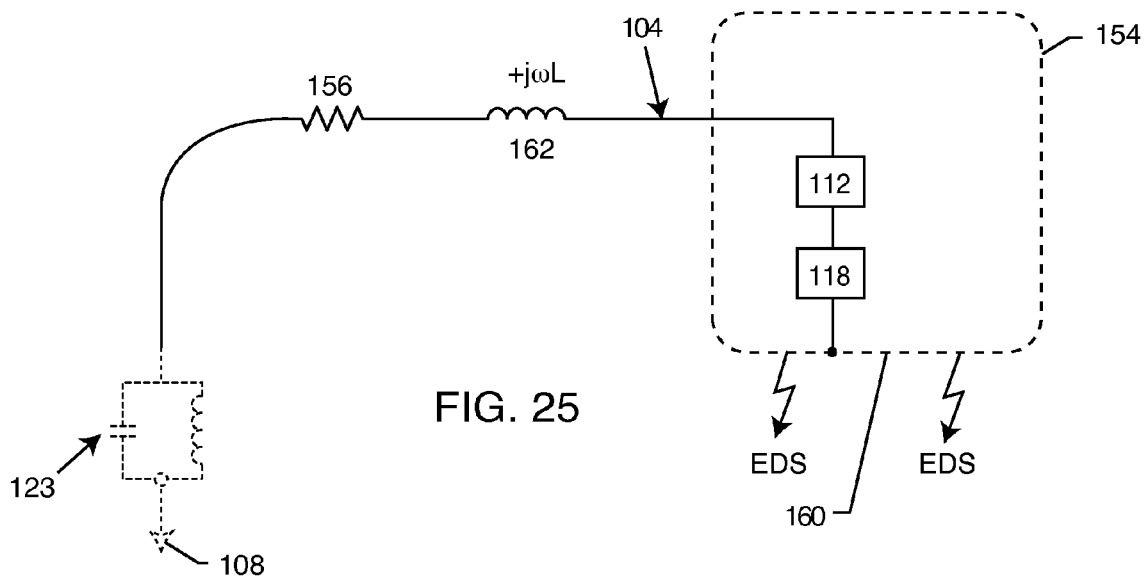
FIG. 25 is an illustration similar to FIG. 24, except that the diverter element has been combined with an impeder element.

FIG. 25 is very similar to FIG. 24 except that the diverter element 112 has been combined with an impeder element 118. Diverter circuits 112 were previously described in FIGS. 4 through 6. Impeder elements 118 were previously described in association with diverter elements in FIGS. 7 through 11. The lead cap 154 of the present invention can therefore be combined with any number of combinations of diverter elements 112 and impeder elements 118.

Figure 26:
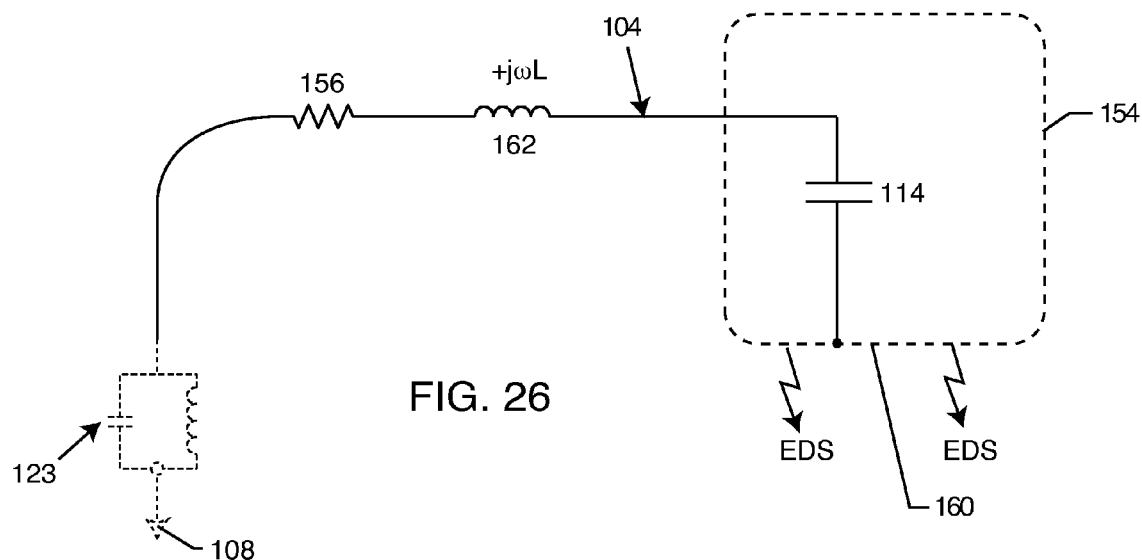
FIG. 26 is an illustration similar to FIG. 24, wherein the diverter element is shown as a capacitor.

FIG. 26 shows an implanted unipolar lead system 104 which is identical to that previously described in FIG. 24. In FIG. 26, the diverter element 112 is shown as a capacitor 114. The capacitor in this case acts as a high pass filter in that it allows high frequency MRI RF energy to be diverted from the lead 104 to the EDS surface 160 of the abandoned lead cap 154. The capacitor 114 creates a $-j$ capacitive reactance which tends to cancel the $+j$ inductive reactance 162 that is associated typically with an implanted lead. This facilitates maximum energy transfer to the EDS surface 160 as has been previously described.

Figure 27:
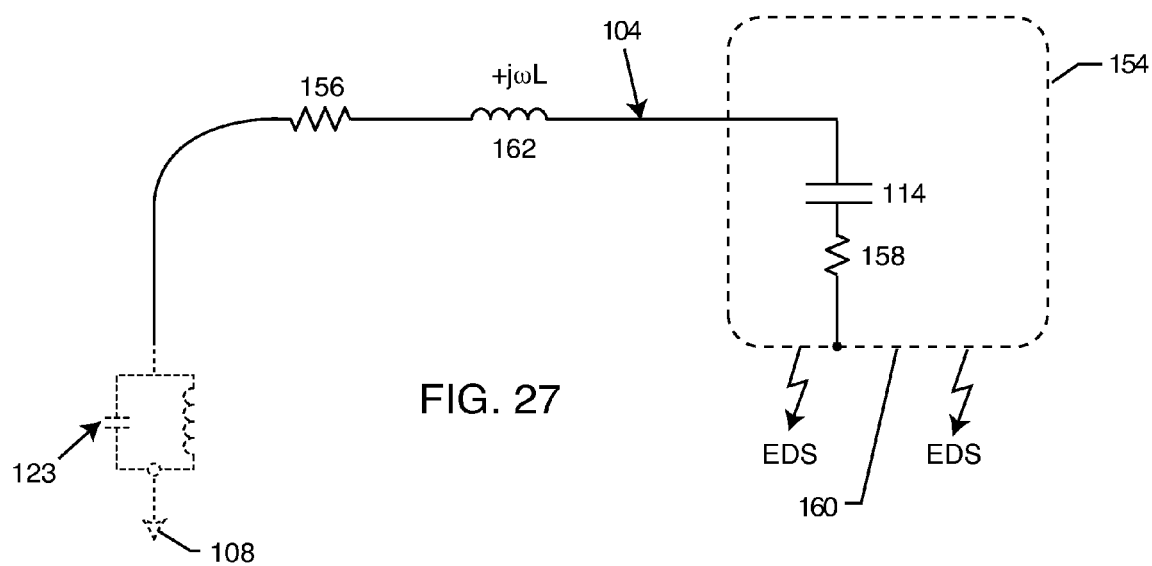
FIG. 27 is an illustration similar to FIG. 26, except that a resistor element has been added in series with the capacitor.

FIG. 27 is identical to FIG. 26 except that a resistor element 158 has been added in series with the capacitor element 114. Resistor element 114 can be part of the capacitor's 114 equivalent series resistance (ESR). Alternatively, the resistor 158 could be a separate discrete resistor, such as a chip resistor. In a particularly preferred embodiment, the value of the resistance 158 would be equal to the characteristic or equivalent resistance of the lead 156. Again, according to Thevenin's Theorem, this would facilitate maximum energy transfer to the EDS surface 160.

Figure 28:
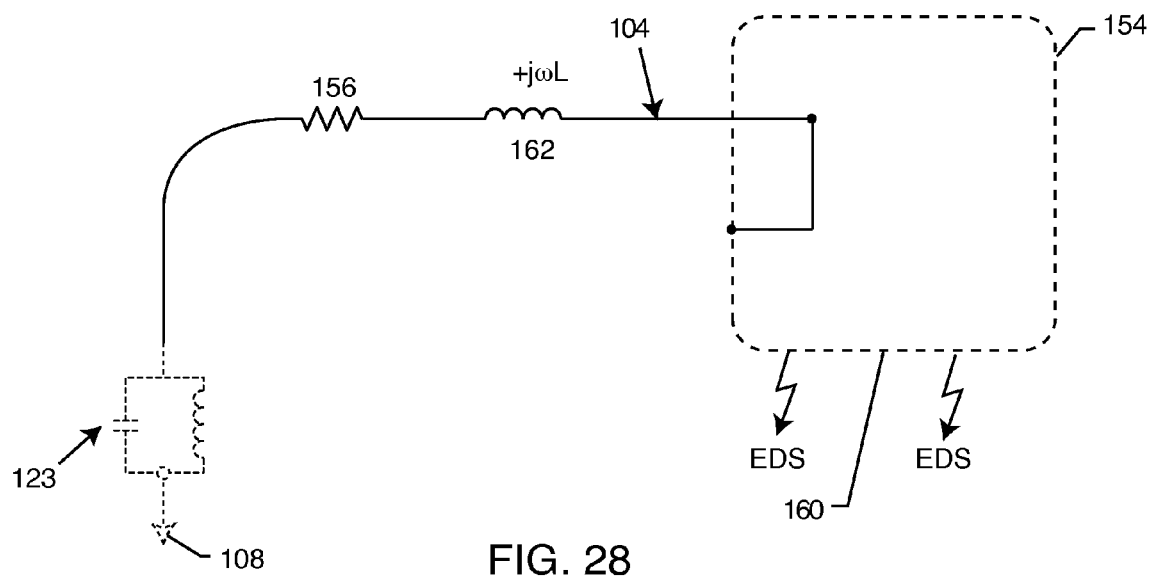
FIG. 28 is an illustration similar to FIG. 24, except that the diverter element is replaced by shorting the lead to the housing of the AIMD.

FIG. 28 is very similar to FIG. 24 except the diverter element 112 has been replaced with a short circuit. The short circuit directly connects the implanted lead 104 to the EDS surface 160 of the abandoned lead cap 154. Although not optimal, for energy efficiency, this simple approach still directs a great deal of MRI RF induced energy from the lead 104 to the EDS surface 160 in accordance with the present invention.

Figure 29:
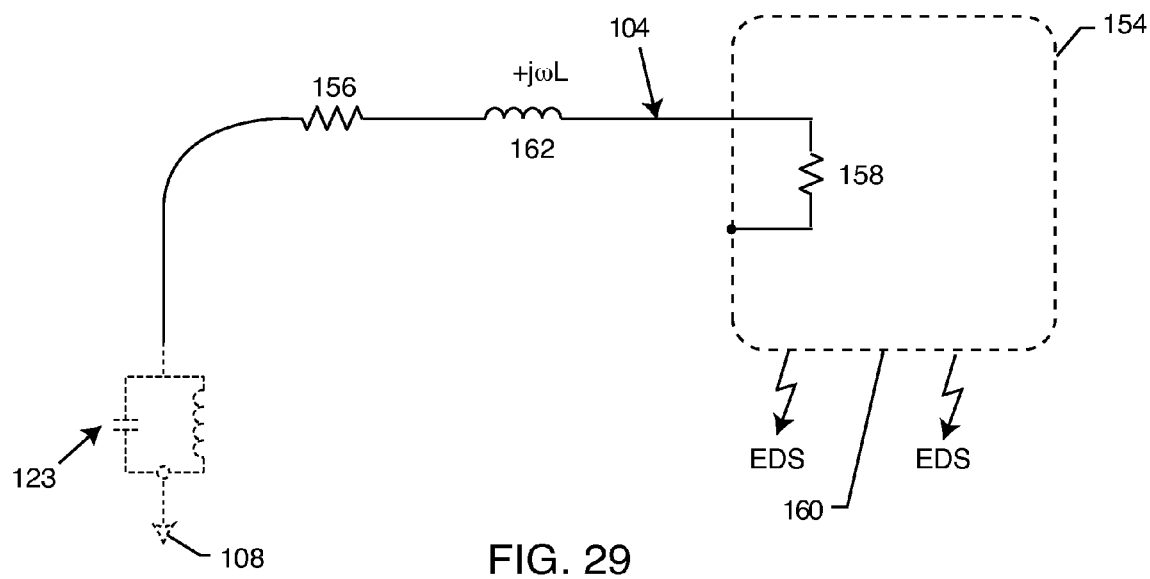
FIG. 29 is an illustration similar to FIG. 24, wherein the diverter element is shown as a resistor element.

FIG. 29 is also very similar to FIG. 24 except that the diverter element 112 has been replaced with a simple resistor element 158. In order to accomplish maximum energy transfer in accordance with Thevenin's Theorem, diverter resistor 158 would be equal to the characteristic resistance 156 of the implanted lead. The short circuit illustrated in FIG. 28 and the resistor 158 illustrated in FIG. 29 are not optimal for maximum energy transfer to the EDS surface 160. However, in certain abandoned lead situations, particularly those that are near the MRI bore or ISO center, these would be adequate.

Figure 30:
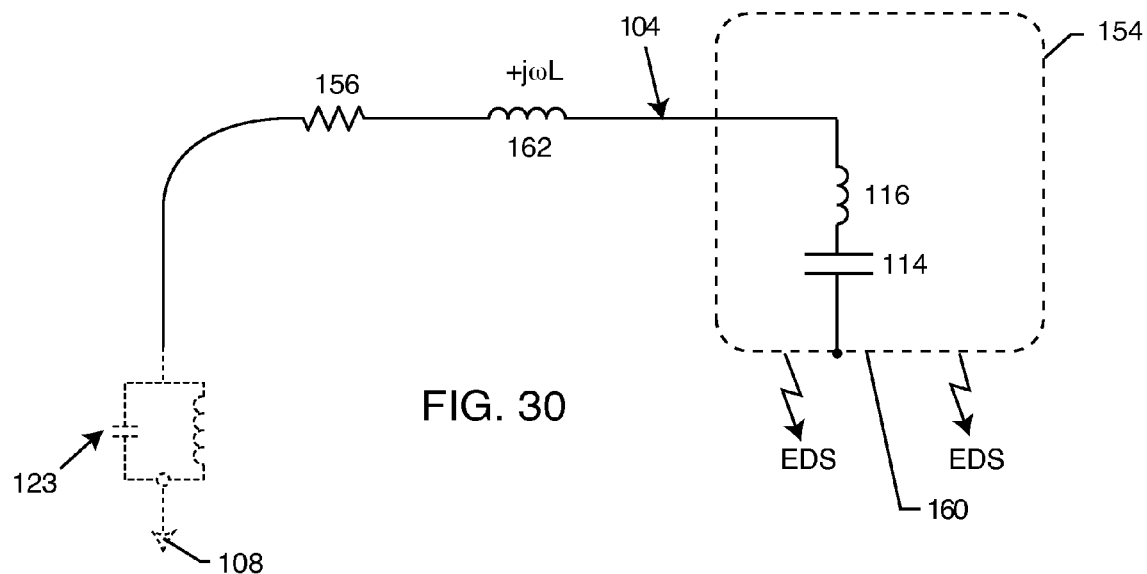
FIG. 30 is an illustration similar to FIG. 24, wherein the diverter element is shown as an inductor in series with a capacitor.

FIG. 30 is very similar to FIG. 24 except that the diverter element 112 consists of an inductor 116 in series with a capacitor 114. This is known as an L-C trap filter as was previously described in FIG. 6. In this case, the inductor element 116 and the capacitor element 114 have been designed to be resonant at the pulsed RF frequency of the MRI equipment. Therefore, at this selected frequency, this forms an RF short to the EDS surface 160 of the abandoned lead cap 154.

Figure 31:
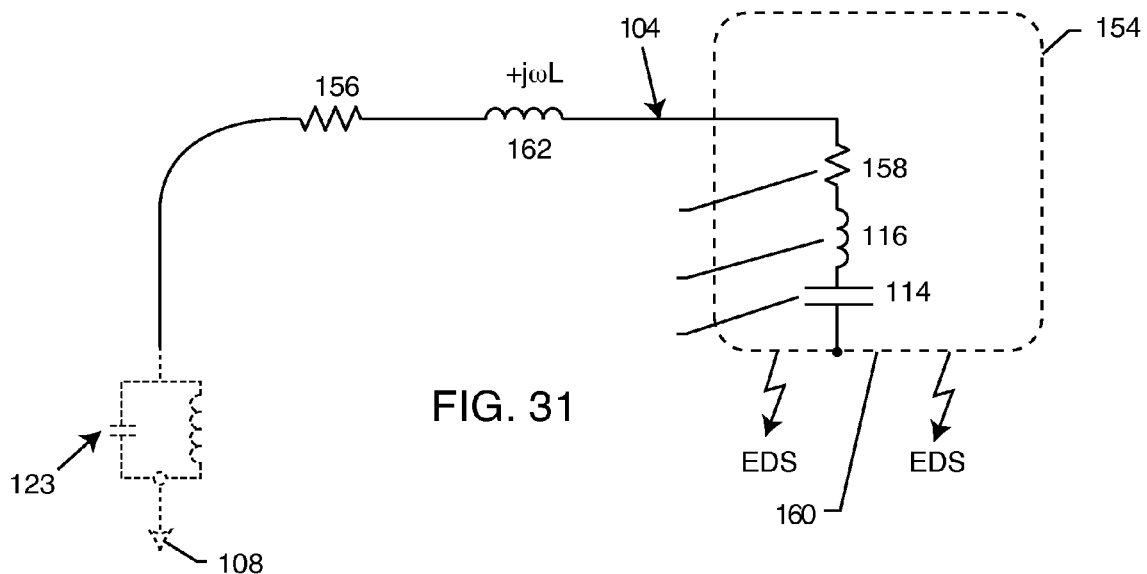
FIG. 31 is an illustration similar to FIG. 30, wherein a series resistance is added to the L-C trap filter.

As shown in FIG. 31, a series resistance 158 could be added in series with the L-C trap filter of FIG. 30 consisting of the inductor 116 and the capacitor 114. The resistor 158 further optimizes energy transfer from lead wire 104. The resistance 158 is also used to control the Q of the resonant L-C trap filter and its associated resonant bandwidth.

Figure 32:
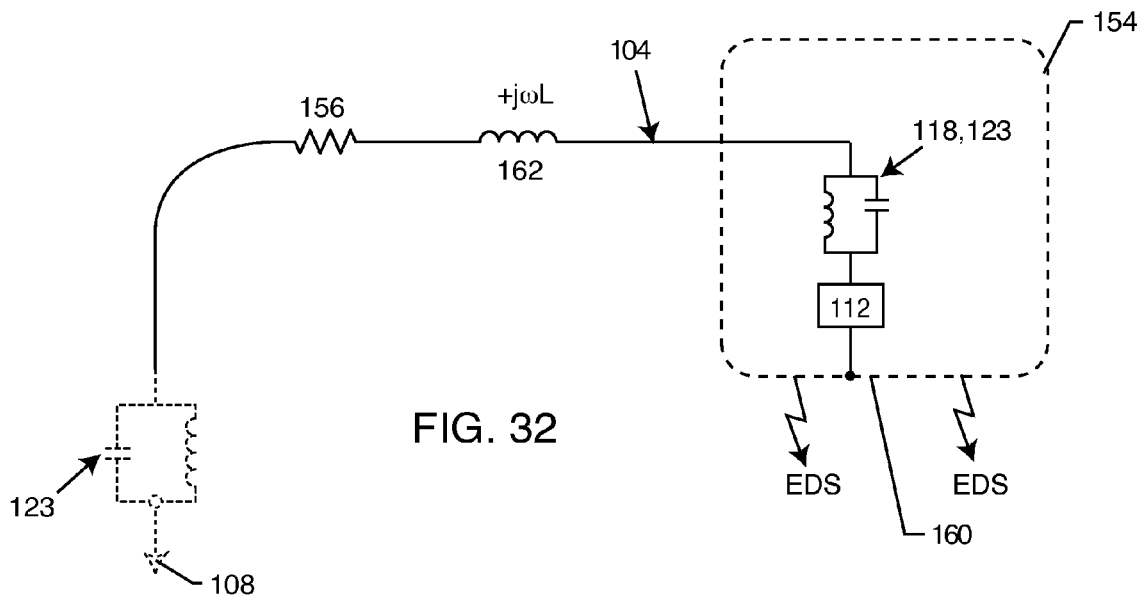
FIG. 32 is an illustration similar to FIG. 25, wherein the impeder element is shown as a bandstop filter.

FIG. 32 is very similar to FIG. 25 showing both a diverter element 112 and impeder element 118. The diverter element 112 as shown in FIG. 32 could be any of the diverters as previously described in FIGS. 26 through 31. In this case, the impeder element is a bandstop filter 123 as previously described in FIG. 11.

Figure 33:
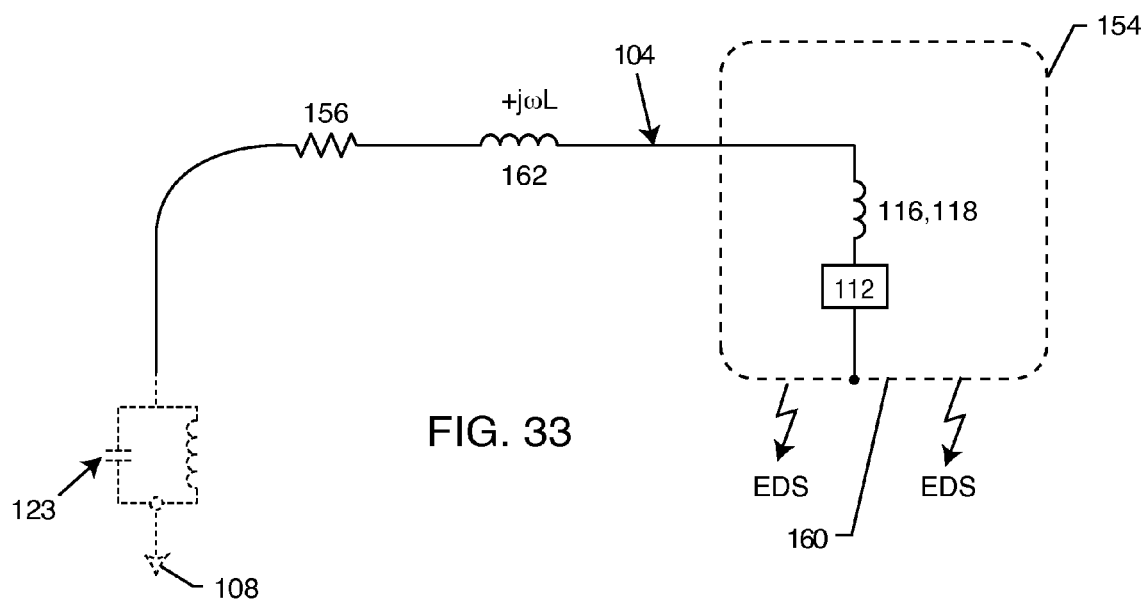
FIG. 33 is an illustration similar to FIG. 32, except that the impeder element is a simple inductor.

FIG. 33 is very similar to FIG. 32 except that the impeder element 118 is a simple inductor 116 which was previously described in FIG. 10.

Figure 34:
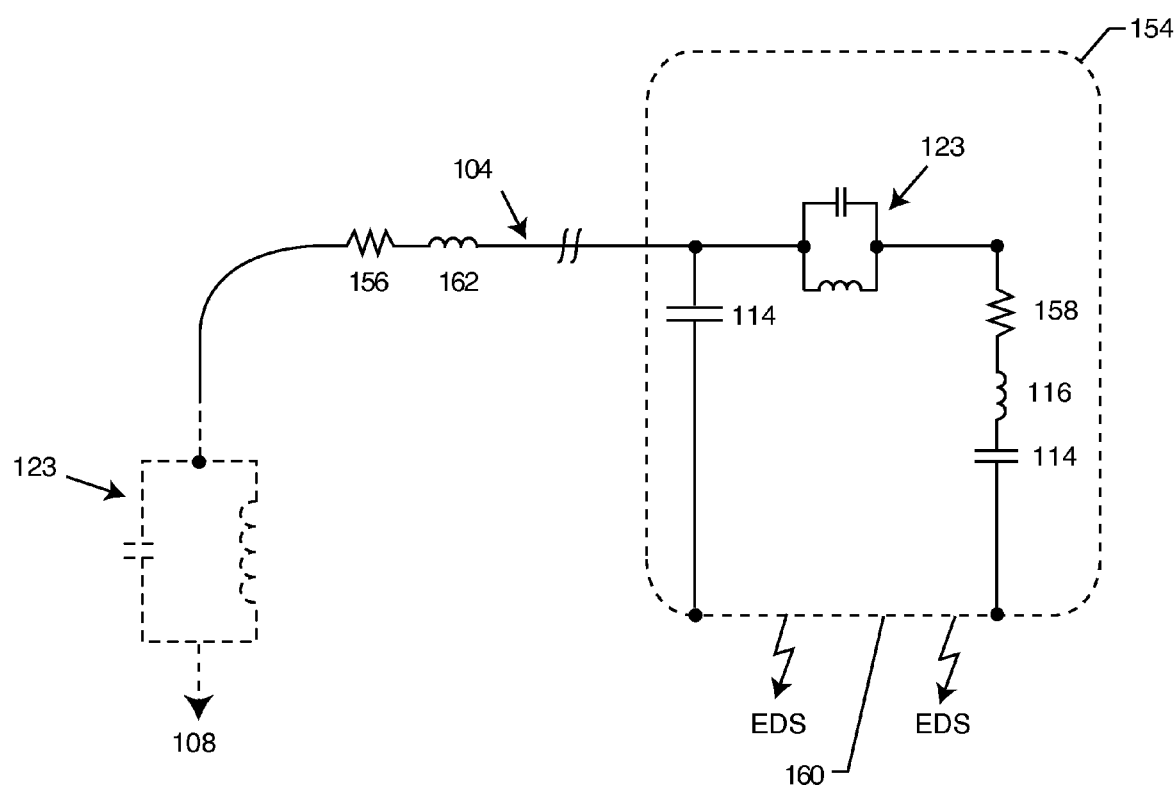
FIG. 34 is an illustration similar to FIGS. 24-33, showing various diverter and impeder elements connected to an energy dissipating surface.

FIG. 34 combines various diverter and impeder elements all into one circuit inside of a novel abandoned lead cap 154. Shown is a diverter capacitor 114 in series with a bandstop filter impeder 123 which is then connected to an RLC trap filter consisting of resistor 158, inductor 116 and capacitor 114 connected to the energy dissipating surface 160. FIG. 34 shows a bandstop filter 123 which is useful when one wishes to impede the flow of currents in implanted lead at certain frequencies such as electrocautery frequencies, while at the same time diverting MRI high frequency induced RF energy to the EDS surface 160. In other words, one could prevent excess electrocautery current from flowing through a distal electrode while at the same time diverting high frequency MRI energy to the EDS surface. The circuit shown in FIG. 34, inside of the AIMD abandoned lead cap 154, is illustrative of just one combination. Any combination of the circuits described in FIGS. 3 through 11 may be embodied and in any combinations.

Figure 35:
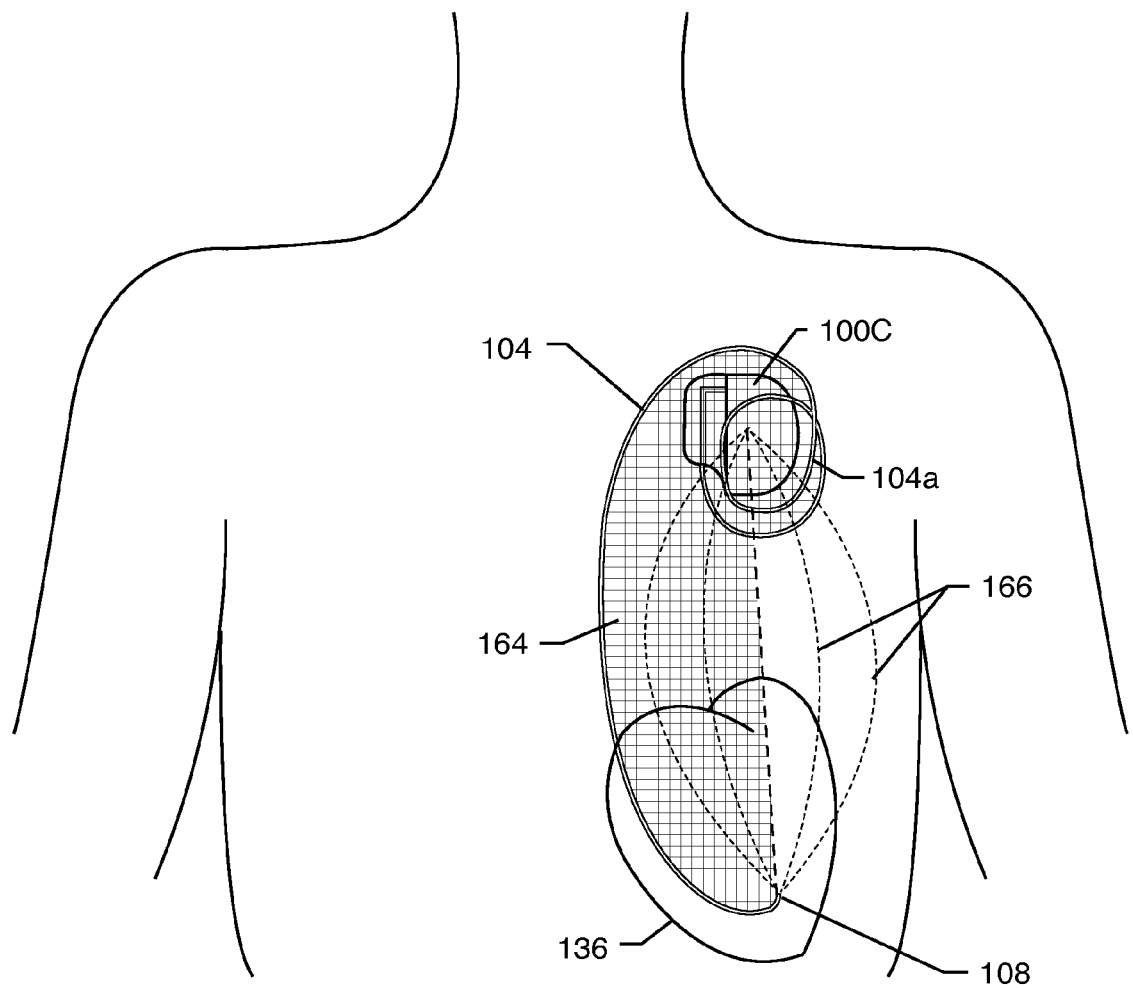
FIG. 35 is an illustration of an X-ray tracing of an implanted cardiac pacemaker in a patient.

FIG. 35 is a patient front view representative of an X-ray tracing of an implanted cardiac pacemaker. The pacemaker 100c is shown installed in a pectoral pocket, which can either be left pectoral (as shown) or right pectoral (not shown). There can be one or more turns of excess lead 104a that's coiled up in the pectoral pocket and then the lead 104 is routed endrocardially down through the superior vena cava into a cardiac chambers 136 as shown. A loop area shown by the checker pattern 164 is formed between the distal tip electrode 108 all along the lead 104 to the AIMD 100c and then through a multi-path tissue return path shown 166 as dashed lines from the AIMD 100c to the distal tip electrode 108 in the heart. MRI low frequency gradient fields couple into this loop 164 by Faraday's Law of Induction. In general, Faraday's Law states that a voltage induced in this loop 164 is directly proportionate to the area of the loop times the rate of change of the magnetic field in Teslas per second. A worse case coupling situation occurs when the field is orthogonal to the loop area 164. Current will flow in the lead 104 unless the lead is opened up (switched open). It is highly undesirable that this low frequency MRI gradient induced current flow into cardiac tissues as this could directly induce cardiac arrhythmias. It is also undesirable if this current should flow into the AIMD electronics as it could either interfere with AIMD electronics (EMI) or it could lead to gradient rectification. In the art, direct cardiac or tissue stimulation is known as Gradient STIM.

Figure 36:
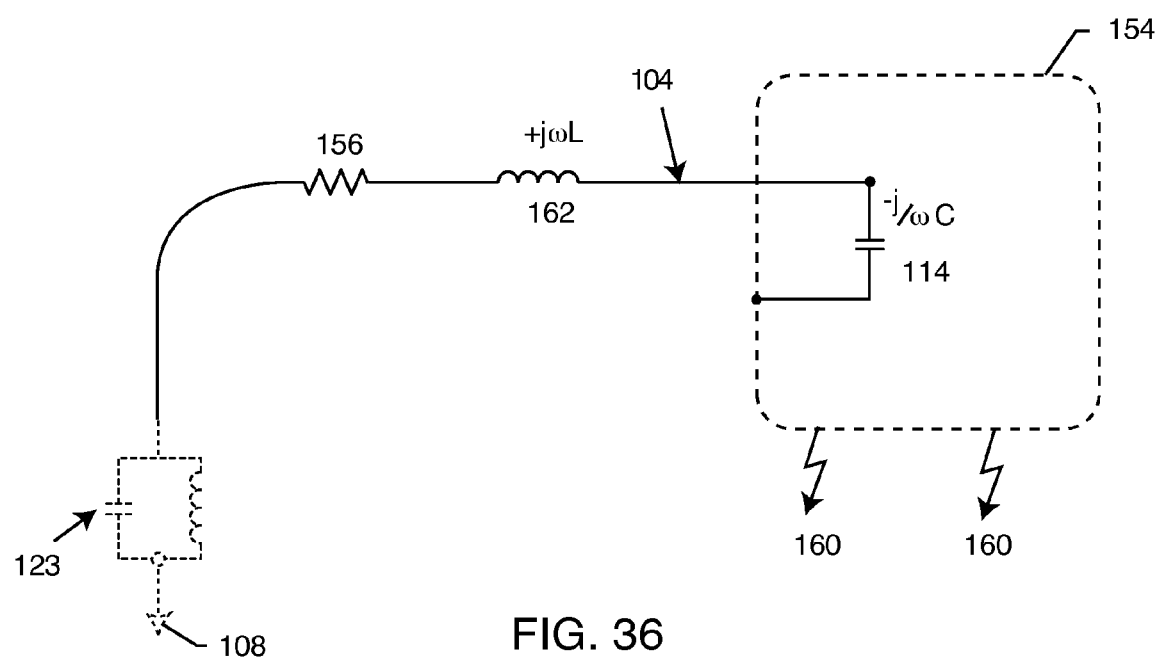
FIG. 36 is an illustration similar to FIG. 26, where the diverter element features a specific capacitive element.

FIG. 36 is another illustration of the unipolar lead system of FIG. 26. In this case, the diverter element 112 features a capacitive element 114 whose capacitive reactance is given by the equation $-j/\omega C$. In a preferred embodiment, the inductance of the implanted lead would first be modeled, calculated or measured. Therefore, the value of capacitance could be tuned or selected such that $-j/\omega C$ is equal and opposite to the lead 104 characteristic inductive reactance $+j\omega L$. In this case, the reactances cancel each other so that one gets maximal energy transfer to the abandoned lead cap 154 energy dissipating surface 160. As previously described, the capacitor's equivalent series resistance (ESR) could be controlled or a discrete resistance approximately equal to the characteristic resistance of the implanted lead could be added in series in order to further maximize energy transfer from the implanted lead system 104 to the EDS surface 160.

Figure 37:
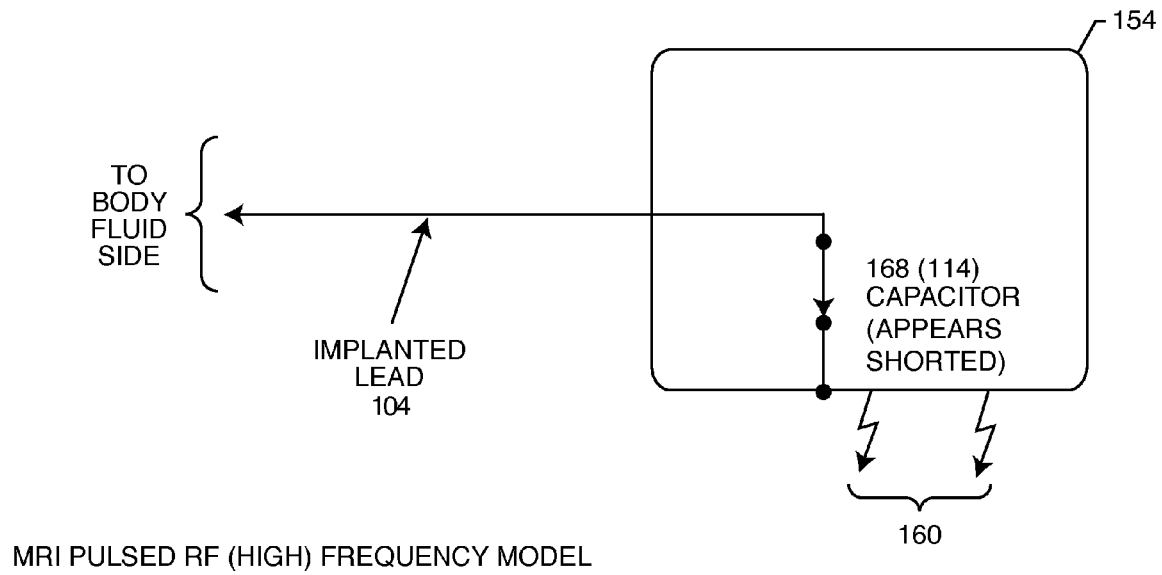
FIG. 37 is a high frequency model of the circuit shown in FIG. 36.

FIG. 37 is the high frequency model of the circuit illustrated in FIG. 36. In this case, at high frequencies, such as MRI RF pulsed frequencies, the capacitor 114 is a very low impedance which effectively appears as a short circuit. This has the desirable effect of pulling or diverting high frequency energy on the lead 104 through the low impedance of the capacitor 114 to the energy dissipating surface 160. The capacitor 114 can be modeled by a switch 168 that is shown closed or shorted to the EDS surface 160. For maximal energy transfer from the lead 104, the capacitive reactance of capacitor 114 has a $-j$ vector which tends to cancel the $+j$ vector that is associated with the characteristic inductive reactance of an implanted lead 104.

Figure 38:
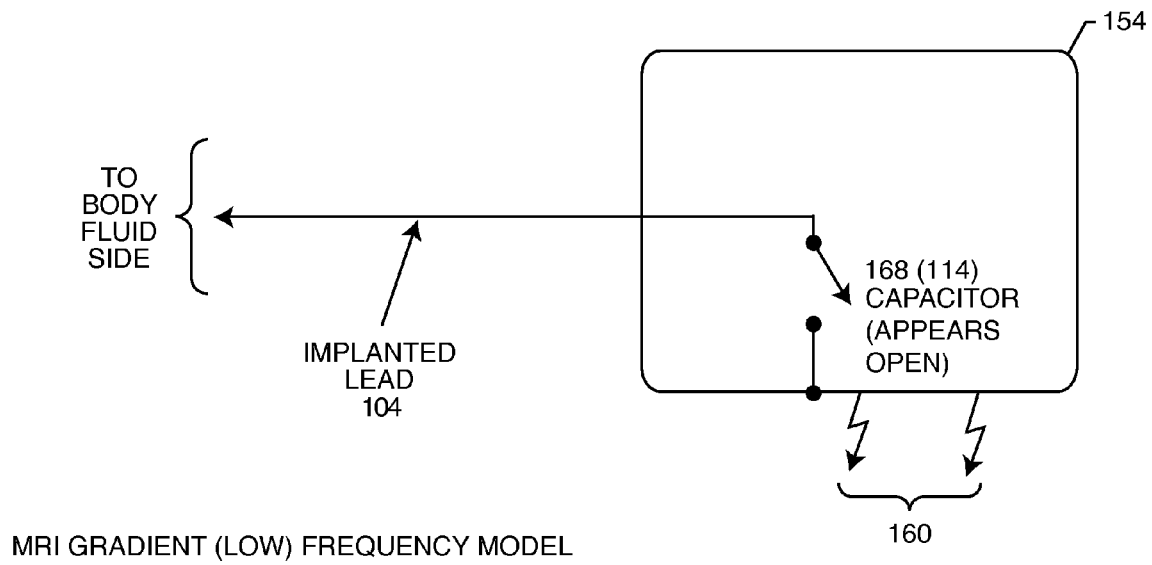
FIG. 38 is a low frequency model of the circuit shown in FIG. 36.

FIG. 38 is the low frequency model of the circuit previously illustrated in FIG. 36. In this case, at low frequencies, the capacitor 114 appears as a very high impedance which effectively appears electrically as an open circuit. As previously mentioned, this has the desirable effect of preventing gradient currents from flowing in the implanted lead and the associated loop through body tissue and AIMD electronics. In other words, the diverter element capacitor 114 that was illustrated in FIG. 36 performs two very important functions. The first function is that it diverts high frequency RF energy that is induced on the lead from exposure to high power RF fields such as occur during magnetic resonance imaging. In addition, the capacitor looks like a very high impedance when energy is coupled to the lead 104 from low frequency MRI gradient fields which are typically below 4 kHz. In this case, the capacitor looks like an open circuit or open switch that prevents these gradient currents from flowing in an implanted lead loop area 164. It has been shown that gradient induced currents can directly stimulate tissue. Such currents have been known to be captured by the heart as dangerously high repetition rates or directly induce pain into the spinal column or have other deleterious effects. In the case of capturing the heart at the high rate, this can induce a ventricular arrhythmia that can even be life threatening. Referring once again to FIG. 36, the capacitor 114 can be combined with a series resistance element or it could even be replaced by a series RLC trap filter or other diverter circuit as previously described herein. All of these would have the desired effect of shutting high frequency RF energy to the abandoned lead cap EDS circuit while at the same time preventing gradient current flow in the implanted lead loop.

Figure 39:
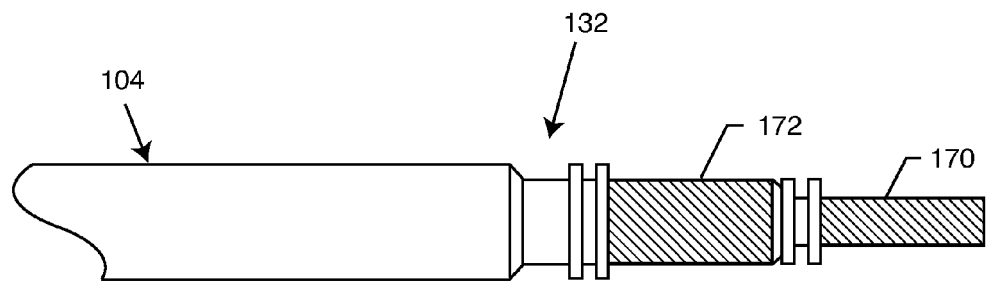
FIG. 39 illustrates a typical cardiac IS-1 proximal end connector.

FIG. 39 illustrates a typical cardiac IS-1 proximal end connector 132. It is attached to the end of an implanted lead 104 as shown. Shown are two contact surfaces 170 and 172. Contact surface 170 typically connects to a distal tip electrode 108. The contact surface 172 typically connects to ring electrode 110.

Figure 40:
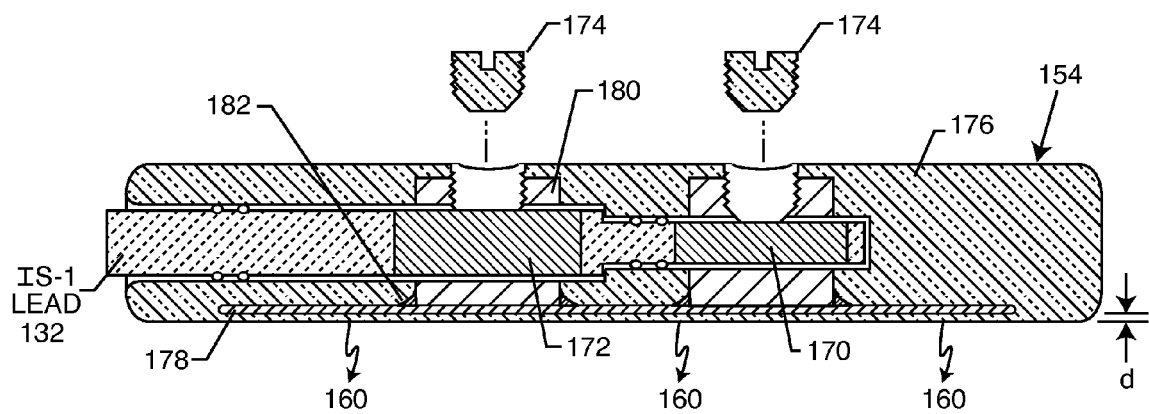
FIG. 40 is a cross-sectional side view of an abandoned lead cap designed to receive the proximal end connector of FIG. 39.

FIG. 40 illustrates a cross-section of a novel abandoned lead cap 154 of the present invention which is suitable for termination of an IS-1 lead male connector 132. Shown are two set screws 174 which are used to affix the lead 104 contact surfaces 170 and 172 firmly in place. In alternative embodiments, using IS-1 or alternative connectors, there may be a single-set screw where the other electrical connection is made by an o-ring spring contact-like mechanism. There is an insulative dielectric material 176 which can be of typical medical grade plastic or the like. The conductive tip 170 and ring 172 of the IS-1 lead connector 132 is shown connected to a metal plate 178. The metal plate 178 can be slightly embedded within the insulator 176 to form a parasitic capacitance between the metal plate 178 and the surrounding body tissue in the abandoned lead cap area. Set screws 174 are threaded into metal blocks 180 so they make both electrical and mechanical contact to the electrical contact areas 170 and 172 with a proximal IS-1 connector 132. The metal blocks 180 are electrically connected via the electrical connection material 182 to the metal plate 178. The amount of capacitance is determined by the dielectric thickness "d" and the surface area of the metal plate 178 and also the dielectric constant of the insulating material and surround human tissues. As previously stated, the capacitive reactance in ohms is given by the equation $$X_C = \frac{1}{2\pi f C}.$$

Therefore, at high frequency, such as 64 MHz, the abandoned lead cap, in the area of metal plate 178, becomes an energy dissipating surface 160.

Figure 41:
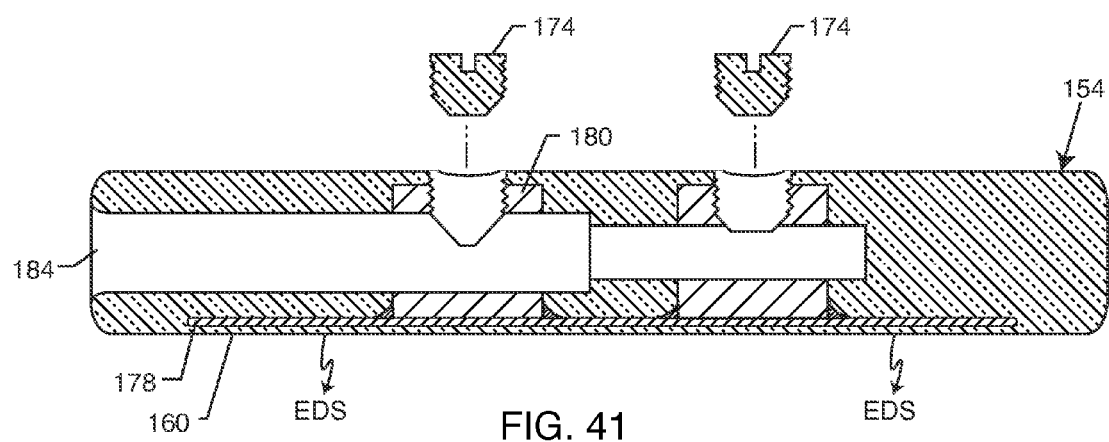
FIG. 41 is a view similar to FIG. 40, except that the IS-1 proximal end connector of FIG. 39 has been removed.

FIG. 41 is the same as FIG. 40 except that the IS-1 connector 132 has been removed. In other words, FIG. 41 is the abandoned lead cap 154 that would be kept in hospital inventory prior to its insertion on the tip of an abandoned IS-1 lead connector 132.

Figure 42:
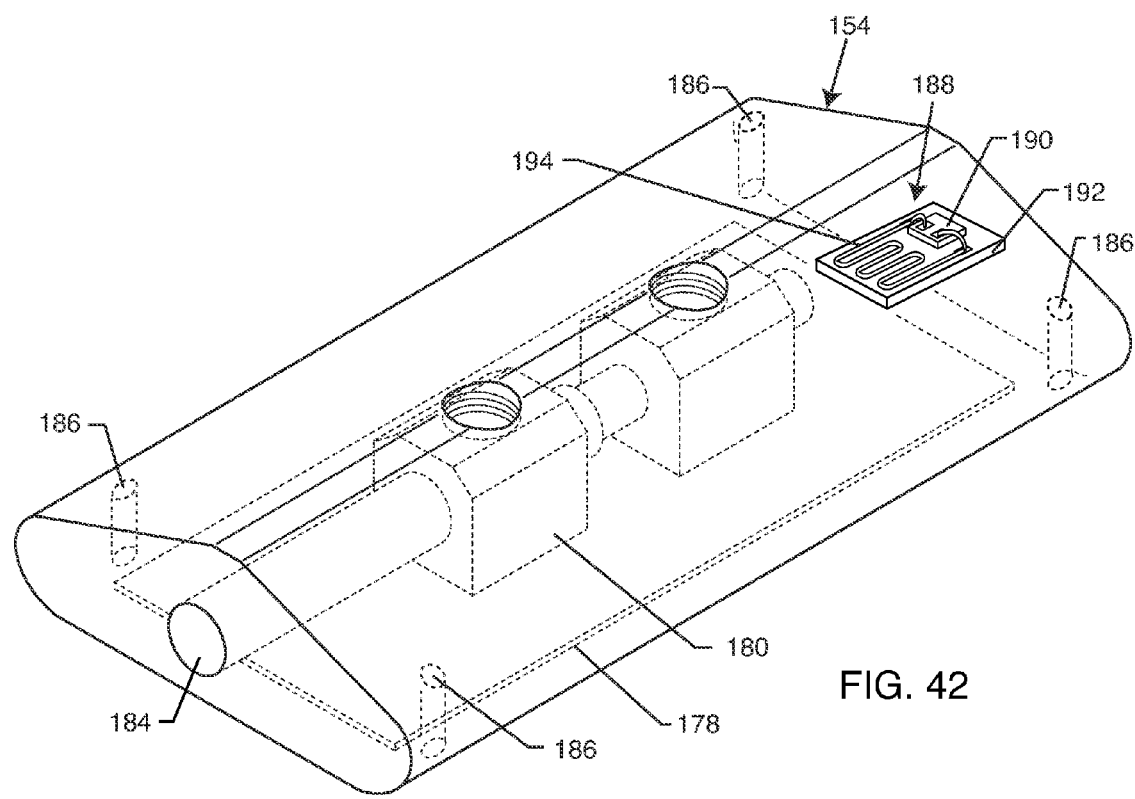
FIG. 42 is an isometric view of the abandoned lead cap of FIGS. 40 and 41.

FIG. 42 is an isometric view of the novel abandoned lead cap of the present invention as previously illustrated in FIGS. 40 and 41. FIG. 42 is for termination of a bipolar lead in that it only has one IS-1 port 184. Also shown are suture holes 186. These are to be used by the implanting physician to run a suture so that the novel abandoned lead cap 154 of FIG. 42 can be affixed to surrounding body tissues, bone or the like. Shown is an RFID tag 188 which consists of an RFID microchip 190 disposed on substrate 192. Associated with the RFID chip is an RFID antenna 194. RFID tags are well known in the prior art and take on a variety of shapes including circular antennas, spiral antennas, solenoid antennas fielded dipoles or a circuit trace antenna as illustrated. The RFID tag 188 enables a means of quick electronic identification by emergency room personnel, a radiologist, or an implanting physician that the patient indeed has an abandoned lead and also that the abandoned lead has a cap with an EDS surface that is MRI compatible, for example, with a 1.5 Tesla system. It should be noted that just because an abandoned lead is compatible with a 1.5 Tesla system does not mean it is safe, for example, in other MRI systems such as 3.0 Tesla systems. US 2006/0212096 and U.S. Ser. Nos. 12/566,490 are incorporated herein by reference. The RFID tag 188 can be incorporated with any novel abandoned lead cap 154 that is associated with an energy dissipating surface 160.

Figure 43:
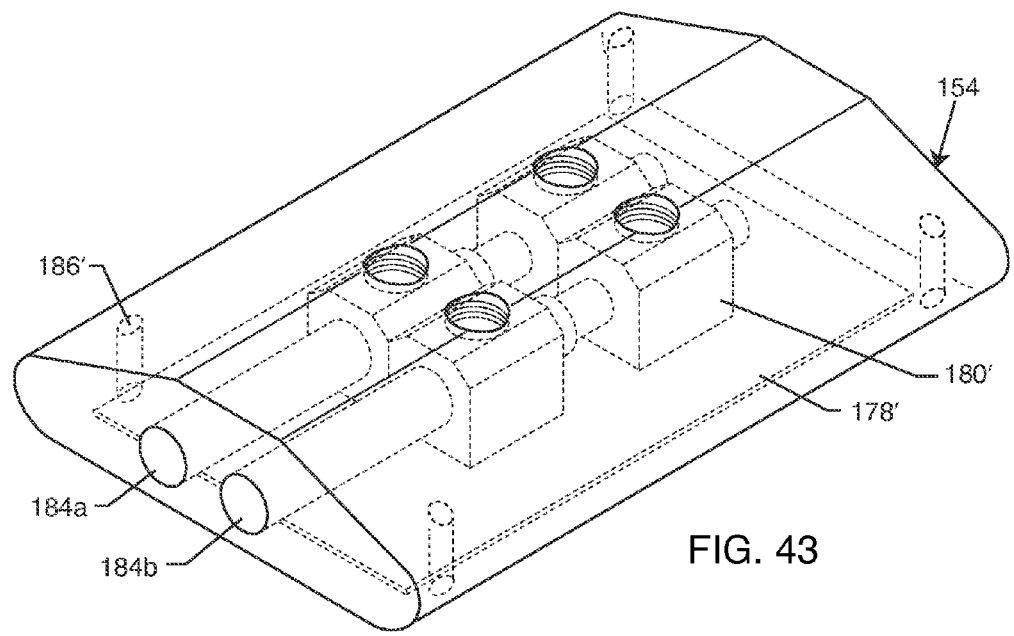
FIG. 43 is an isometric view of a lead cap similar to that of FIG. 42, except that it has two proximal connector-receiving ports.

FIG. 43 is an isometric view which is identical to FIG. 42 except that it has two IS-1 ports 184*a* and 184*b*. It should be noted in FIG. 43 that the tip and ring connectors 170 and 172 are both shorted to the common metal plate 178'. In other words, at the point of lead point termination, all four of the lead wires (two bipolar leads) 104 are all shorted together and connected to metal plate 178'. In some implanted lead configurations, there is a concern that the common metal plate 178' could act as a common reference point. In other words, if there were substantial RF energy be interjected into lead port 184*a*, but not on lead port 184*b*, then via the common metal plate, energy could be reflected from one implanted lead back down to another. As will be seen in subsequent figures, such as FIG. 45 and on, variable impedance diverter 112 and impeder 118 elements can be used to balance this so it does not happen.

Figure 44:
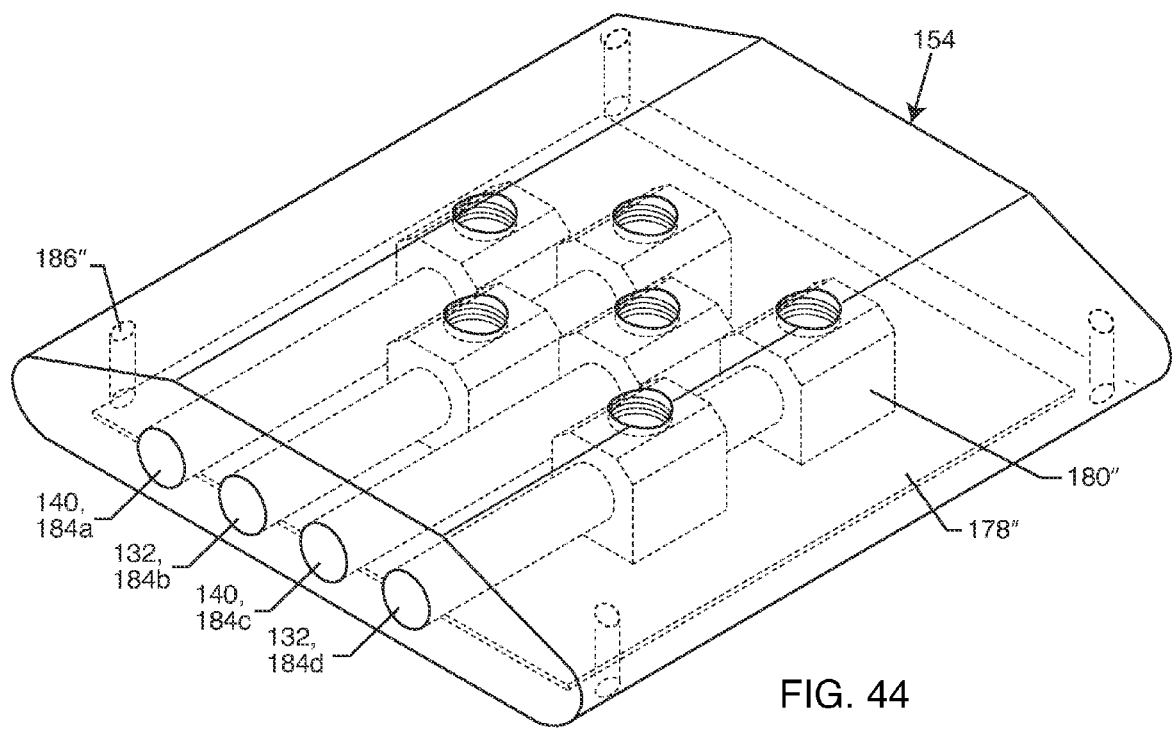
FIG. 44 is an isometric view of a lead cap similar to that of FIG. 42, except that it has four proximal connector-receiving ports.

FIG. 44 illustrates an alternative embodiment showing four IS-1 or DF-1 ports 184*a* through 184*d*. For example, this could be used to terminate the leads of an implantable defibrillator lead system as previously illustrated in FIG. 16. In this particular case, two of the ports would be IS-1 (132) compatible and two of the other ports would be DF-1 (140) compatible.

Figure 45:
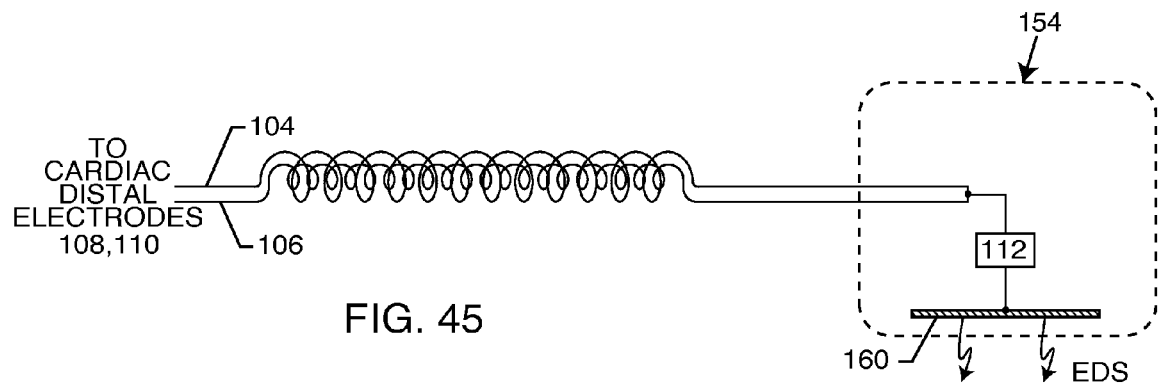
FIG. 45 is a schematic diagram of the unipolar abandoned lead cap of FIGS. 40-42.

FIG. 45 is a schematic diagram showing the unipolar abandoned lead cap 154 of FIGS. 40, 41 and 42. Shown is a general diverter element 112, which in the case of FIGS. 40, 41, 42, 43 and 44, are capacitor elements 114 as previously described in connection with FIG. 5.

Figure 46:
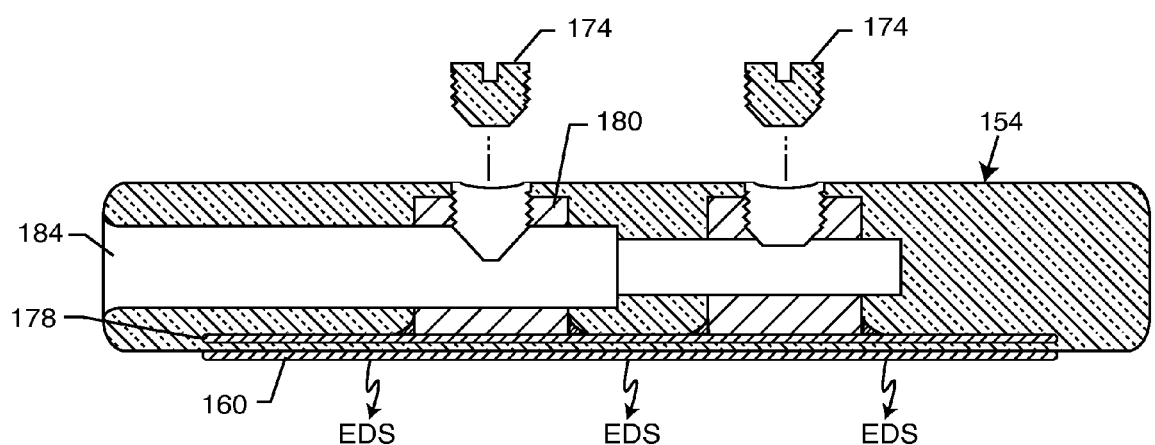
FIG. 46 is a view similar to FIG. 41, showing both an internal metal plate and an external energy dissipating surface plate.

FIG. 46 is a modification of FIG. 41 showing both an internal metal plate 178 and an external metal plate EDS surface 160. This forms a higher value and a more precise capacitance 114 between metal plate 178 and the energy dissipating surface 160 as shown. The capacitance is formed by the overlapping area of plate 178 and the EDS surface plate 160. The capacitance is effected not only be the overlapped area, but also by the separation thickness between the two plates and the dielectric material of the plastic or insulating material that is disposed between the two plates.

Figure 47:
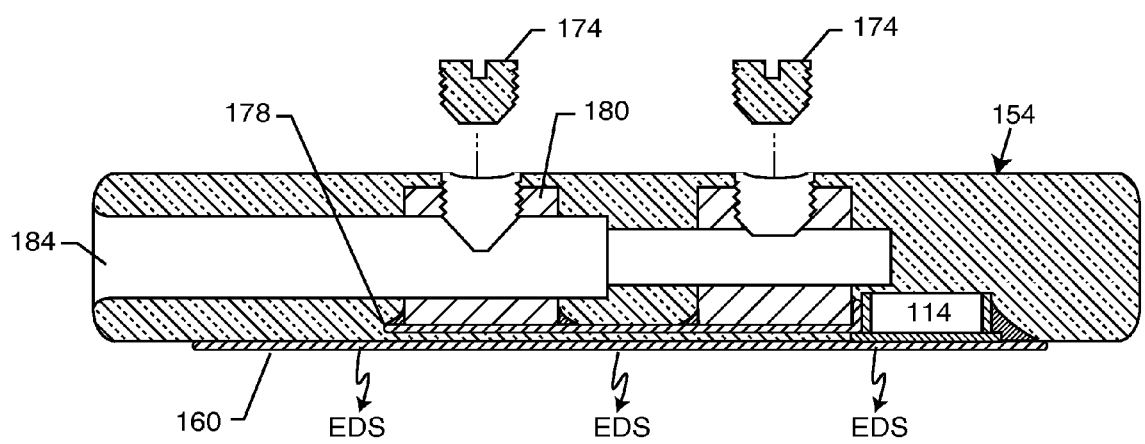
FIG. 47 is a view similar to FIG. 46, showing a capacitor connected between the internal metal plate and the energy dissipating surface.

FIG. 47 is yet another modification of the novel abandoned lead cap 154 as illustrated in FIG. 46 wherein a discrete capacitive element 114 has been electrically connected between the metal plate 178 and the EDS surface 160. Referring back to FIG. 47, the dielectric constant of the capacitor 114 would be relatively high. In this way, a relatively high value of capacitance could be disposed as diverter elements between the distal tip and ring electrodes 170, 172 and the energy dissipating surface 160 as shown. The schematic diagram, as previously illustrated in FIG. 45, would still apply except that the value of capacitance C would be much larger. Accordingly, the amount of RF energy dissipated in FIG. 47 would be desirably much greater. Also, the value of capacitance 144 could be carefully selected so that the capacitive reactance effectively cancels the inductive reactance of the implanted lead system for maximum energy transfer. The capacitor 114 as shown could be a prior art monolithic ceramic chip capacitor (MLCC), a chip film capacitor, an electrolytic capacitor, a tantalum capacitor or any other type of discrete capacitor technology.

Figure 48:
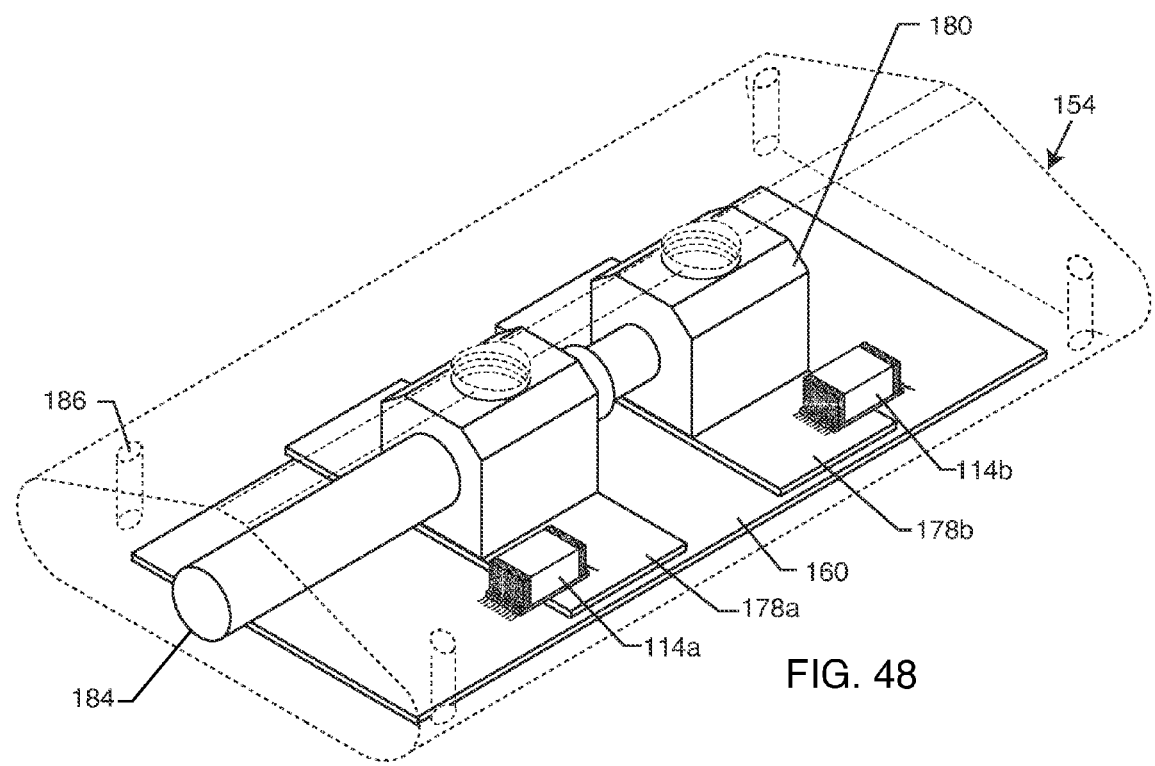
FIG. 48 is an isometric view of the abandoned lead cap of FIG. 47, except that two capacitors are used.

FIG. 48 is an isometric view similar to the unipolar lead cap of FIG. 47. However, in this case, two different capacitors 114*a* and 114*b* are used to make contact to metal plates 178*a* and 178*b* respectively, which are in turn both connected to exterior energy dissipation surface 160. Not that plates 178*a* and 178*b* are electrically insulated from each other. For example, in a pacemaker application, this would be desirable in the case where the implanted lead has a different inductance for the tip circuit as opposed to the ring circuit. Since these are usually coiled and are of different diameters, this would typically be the case.

Figure 49:
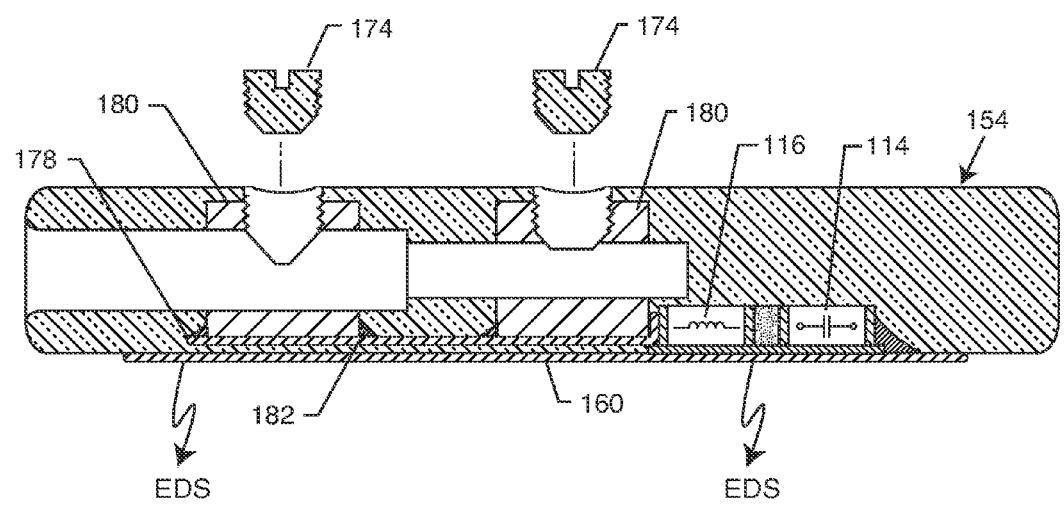
FIG. 49 is a view similar to FIG. 46, except that the tip and ring electrode are both shorted to the metal plate and an L-C resonant circuit is connected between the metal plate and the energy dissipating surface.

FIG. 49 illustrates yet another embodiment wherein the tip 170 and ring 172 are both shorted together to metal plate 178 and that an L-C resonant circuit (FIG. 6) is connected between metal plate 178 and exterior energy dissipation surface 160. As previously mentioned, the values of L and C can be selected such that this trap circuit is resonant, for example, at the resonant frequency of a 1.5 Tesla MRI system (64 MHz). Referring once again to FIG. 49, one notes that the energy dissipating surface 160 is disposed on the outside of the abandoned lead cap 154 where it is in direct contact with surrounding body tissue. This makes for a preferred embodiment where a higher amount of energy transfer will occur.

Figure 50:
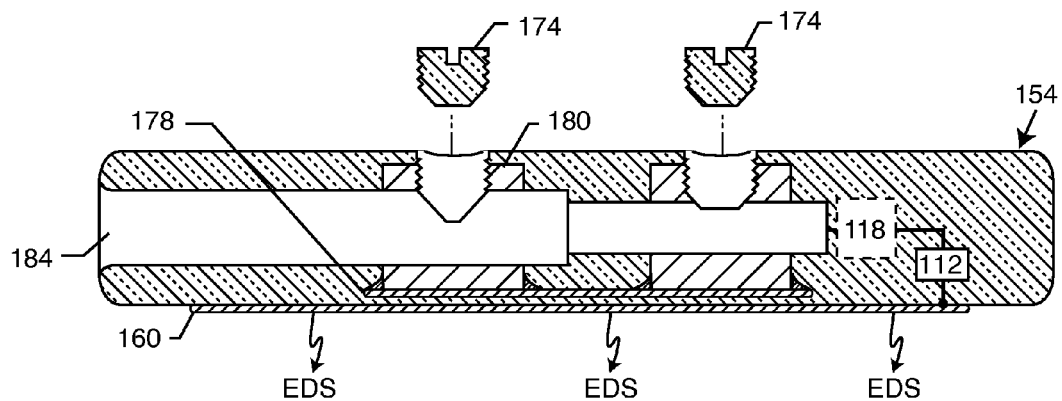
FIG. 50 is a view similar to FIG. 49, illustrating that the circuit elements can be any of those shown in FIGS. 2-11.

FIG. 50 illustrates that circuit elements 118 and 112 can be any of those as previously illustrated in FIGS. 2 through 11. For example, impeder element 118 could be one or more series inductors 116 as illustrated in FIG. 10. In addition, impeder element 118 could be one or more bandstop filters 123 as illustrated in FIG. 11. Frequency selective diverter element 112 could be a simple capacitor 114 as illustrated in FIG. 5 or could be an L-C trap as illustrated in FIG. 6. It could also be a short circuit as illustrated in FIG. 9.

Figure 51:
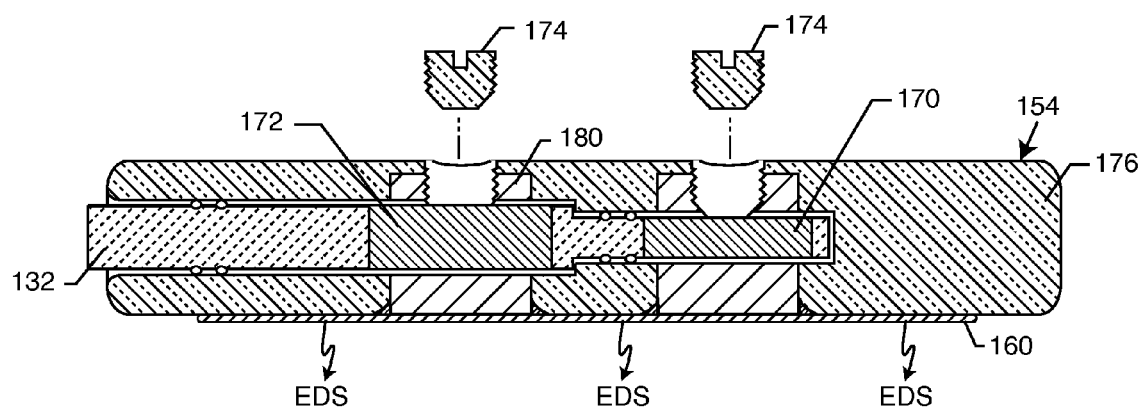
FIG. 51 is a view similar to FIG. 40, except that the metal plate is removed and the energy dissipating surface is on the outside of the insulating housing.

FIG. 51 is very similar to FIG. 40 except that metal plate 178 has been removed and the EDS surface 160 is on the outside of the insulating housing 154. One can see that the EDS surface 160 is now in direct contact with body fluids and tissues. The IS-1 lead connector 132 is shown inserted into the metal holding blocks 180. Once the set screws 174 are torqued properly, the tip 170 and ring 172 circuits will be both electrically shorted together to the metal plate 178, 160. This is electrically equivalent to the short circuit as illustrated in schematic FIGS. 9 and 28.

Figure 52:
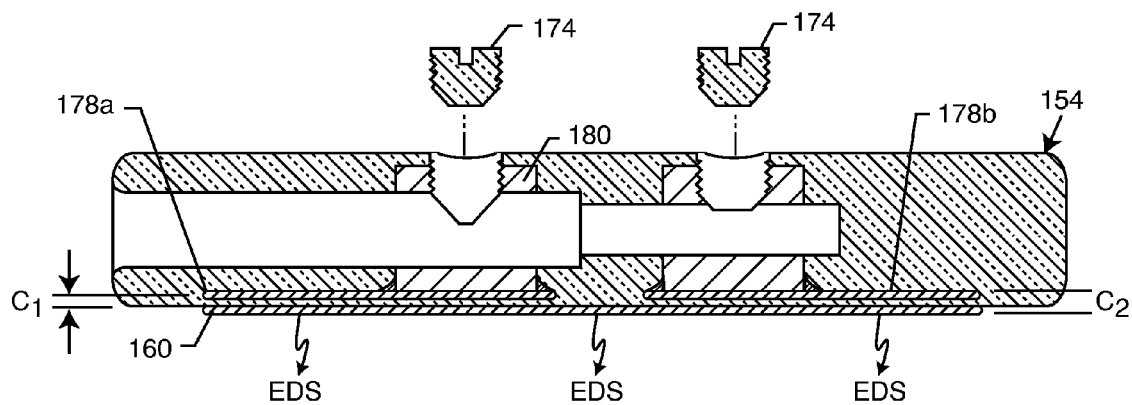
FIG. 52 is a view similar to FIG. 41, except that the metal plate is divided into two electrically isolated plates.

FIG. 52 is very similar to FIG. 41 except that metal plate 178 has been divided into two electrically isolated plates 178a and 178b. This forms two different values of capacitance $C_1$ and $C_2$ to external EDS surface 160. By varying the effective area of metal plates 178a and 178b, one can control the amount of capacitance that is formed to the energy dissipating surface 160.

Figure 53:
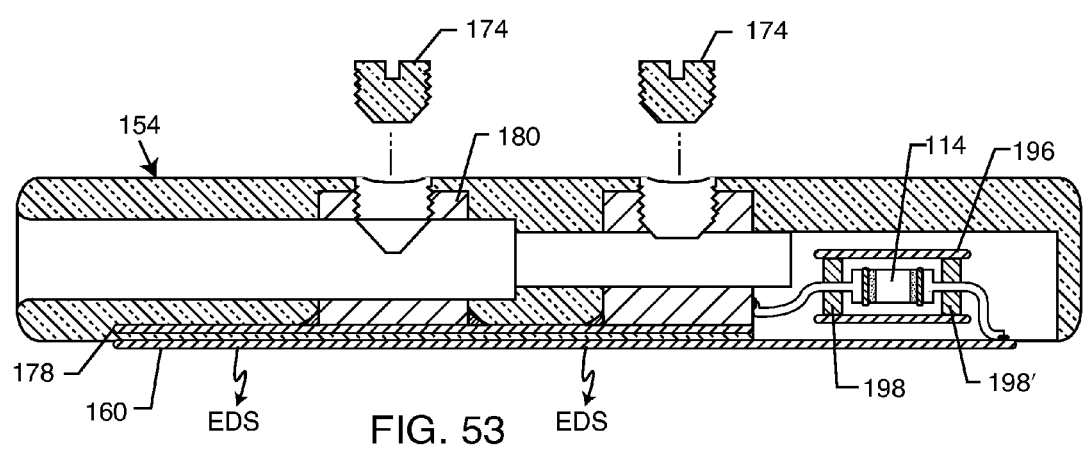
FIG. 53 is a view similar to FIG. 47, except that the capacitor has been placed in a hermetic package.

FIG. 53 is electrically the same as FIG. 47 except that the capacitor 114 has been placed in a novel hermetic package 196. At both ends are hermetic seals 198 and 198' as shown. It will be obvious to those skilled in the art that these could also be glass or gold brazed alumina or equivalent hermetic seals. In this way, the capacitor 114 is protected from intrusion by body fluid. Any of the component systems illustrated in FIGS. 2 through 11 could be similarly enclosed in hermetic housings. U.S. Ser. No. 12/607,234 is incorporated by reference herein.

Figure 54:
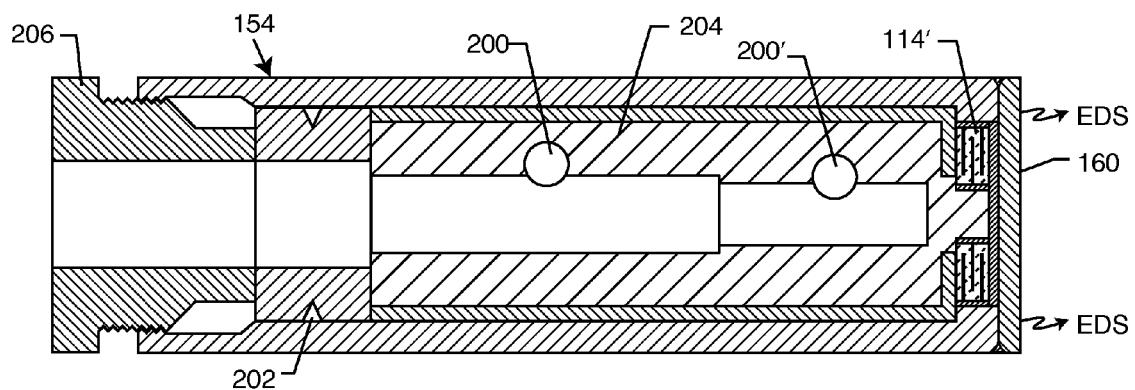
FIG. 54 is a cross-sectional view of another exemplary embodiment of an abandoned lead cap.

FIG. 54 is a modified abandoned lead cap 154 of the present invention including two springs 200 and 200' and a locking mechanism 202. This eliminates the need for the set screws 174 as illustrated in previous drawings. Another alternative is to use one spring 200 and a set screw 174 as an additional locking mechanism 202. A conductive metal energy dissipating surface 160 is disposed adjacent to a ceramic discoidal feedthrough capacitor 114' that makes connection between the metallic housing of the end cap 204 and the energy dissipating surface 160. This forms the equivalent circuit of FIG. 45.

Referring once again to FIG. 54, one can see that there is a threaded locking system 206. Locking mechanism 206 is first guided onto the lead 104. The lead is then inserted so it seats properly against spring surface 200 and 200'. The threaded bushing 206 is slid down and firmly screwed in place. This forms a barrier so that body fluid and/or moisture cannot penetrate into the interior spaces or run down into the lead itself.

Figure 55:
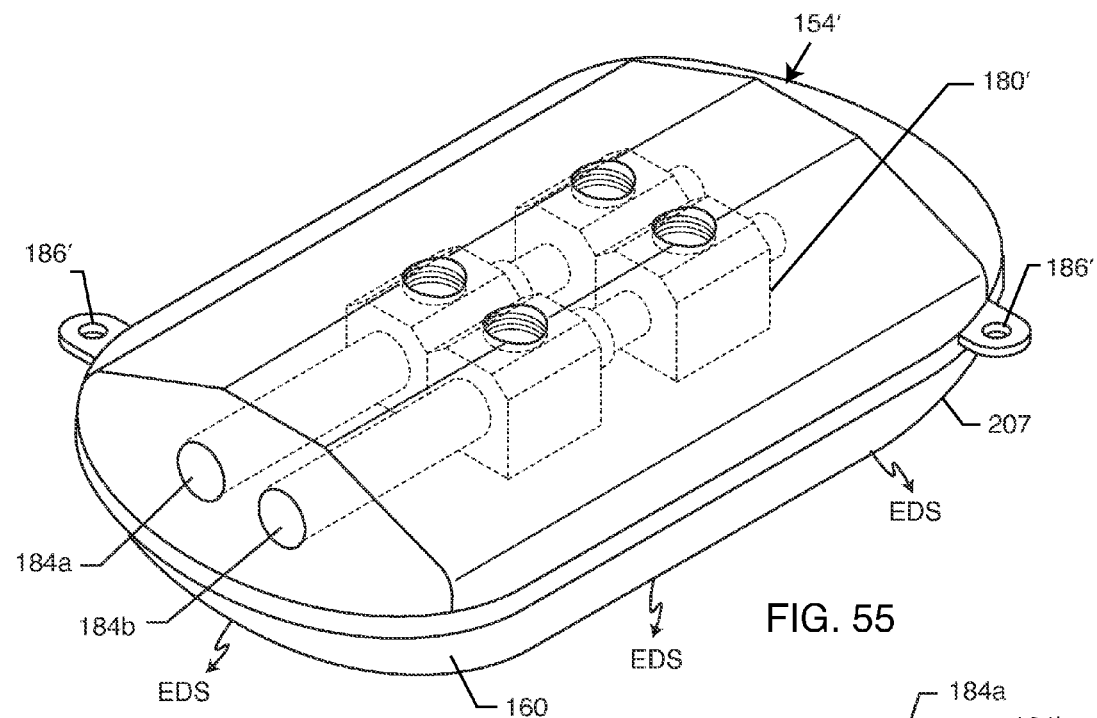
FIG. 55 is an isometric view similar to that of FIG. 43, illustrating a streamlined abandoned lead cap configuration.
Figure 56:
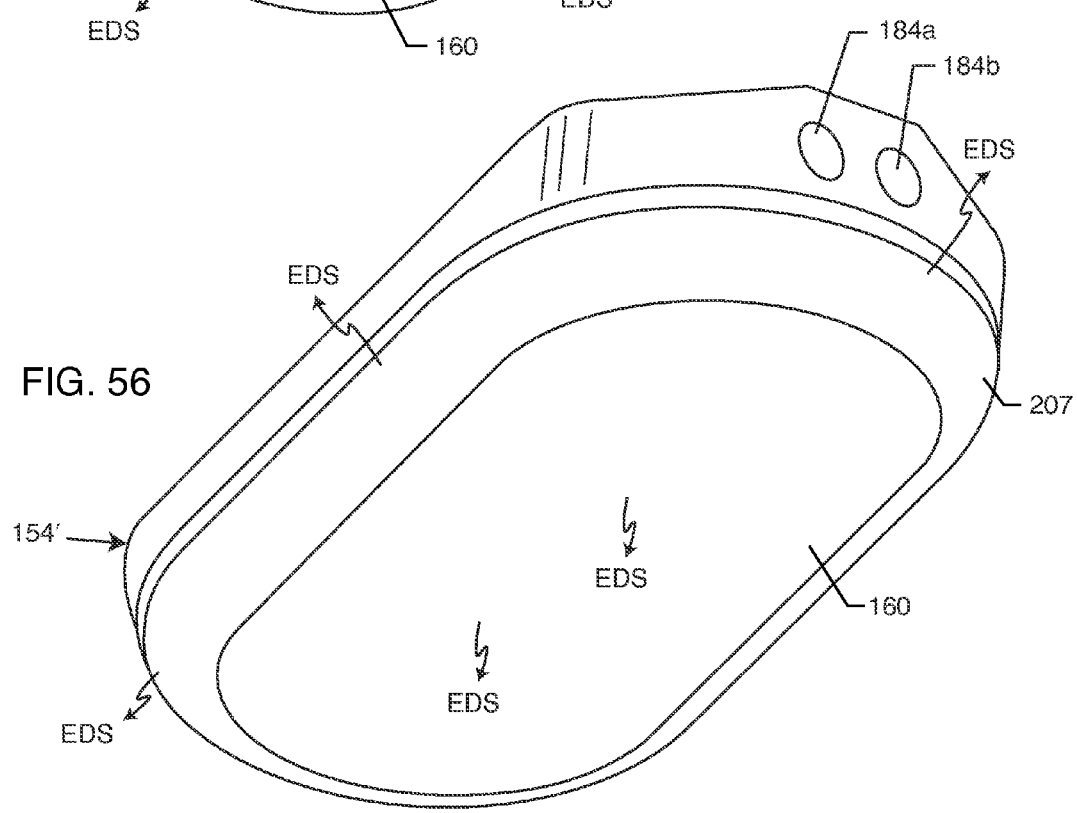
FIG. 56 is an isometric view similar to that of FIG. 55 from the bottom perspective.

FIGS. 55 and 56 illustrate the same abandoned lead cap 154 principle as illustrated in FIG. 43 except that it is much more streamlined and has a thinner shape for better patient comfort. One can see that there is a titanium or stainless steel housing 160 which forms a high surface area energy dissipating surface EDS surface. The titanium EDS surface 160 could have a laser welded interior lid such that it formed a hermetically sealed compartment. This would be convenient for the location of passive electronic components which would form either diverter elements 112 or impeder elements 118 of the present invention. In the case where such a hermetically sealed compartment was formed, there would be a hermetic seal (not shown) to pass leads through in non-conductive relation for attachment to the connector blocks 180'. Referring once again to the novel EDS surface shapes 160 as illustrated in FIG. 55 and 56, one should note that these surfaces in titanium Grades-5 and 23 have been optimized to have a mild forming radius. In general, it is very difficult to form these high resistivity grades of titanium. They do not lend themselves well for stamping, pressing or other forming operations. Radius 207 is illustrated in FIGS. 55 and 56 to show that a gradual curve is formed which is about the maximum that one can shape Grade-5 or 23 titanium. Also shown are optional metallic tabs 186' for placement of sutures during implant operations. In general, the metallic housing 160 would ideally be of a titanium Grade-5 or Grade-23 alloy such that MRI induced eddy current heating would be minimized. Another acceptable alloy would be 6AL4V (this is Grade 5). Grade 23, which is more pure, is preferred. Grade 9 is another type of material that is commonly used in the dental industry. Other grades include Grade 1, Grade 2, Grade 5 and Grade 23. It is a feature of the present invention that an optimal grade of titanium shall be used; such to minimize localized eddy current heating such as may be induced by the magnetic resonant frequency gradient fields. In general, the higher the electrical resistivity of the material that forms the EDS surface 160 the better. For example, pure titanium has an electrical resistivity of 35 microohm-centimeters. Grade-1 titanium, which is very typically used in prior art AIMD housing is 45 microohm-centimeters. Grade-5 titanium is 178 microohm-centimeters and Grade-23 titanium is 168 microohm-centimeters. This is why the use of grades of titanium are relatively high in electrical resistivity are highly preferred. The powerful electromagnetic fields from MRI can directly induce eddy currents into metal plates or housing. Accordingly, it is a feature of the present invention that high resistivity materials are preferred such that eddy current heating is minimized. In addition to titanium, there are grades of stainless steel, which tend to have moderately high electrical resistivities. These are not preferred, but are acceptable to also minimize eddy current losses. This includes alloy 304 stainless steel, which is 72 microohm-centimeters; 316 stainless steel, which is 74 microohm-centimeters; and a type of stainless steel alloy known as Haynes 25 which is 88.6 microohm-centimeters.

Figure 57:
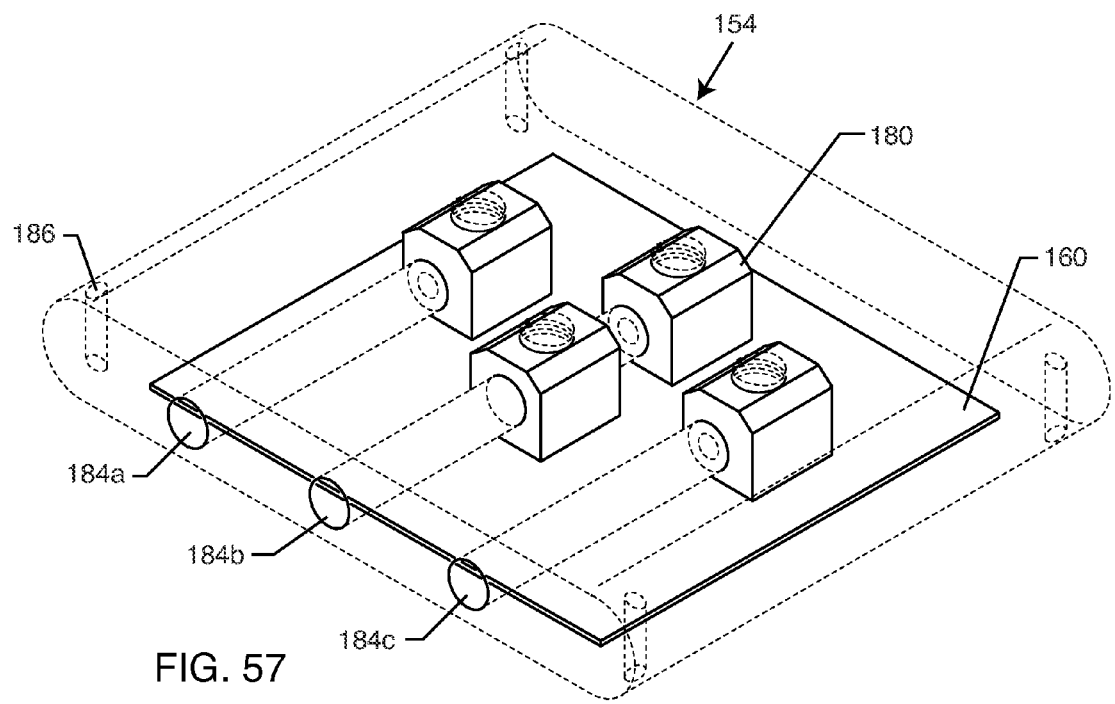
FIG. 57 is an isometric view of an exemplary three port abandoned lead cap.

FIG. 57 is an illustration of a three-port novel abandoned lead cap 154 of the present invention. One can see that there is a single low voltage connector port 184b for a tip and ring type of lead and two DF ports 184a and 184c for high voltage. All of these are electrically connected to EDS surface 160.

Figure 58:
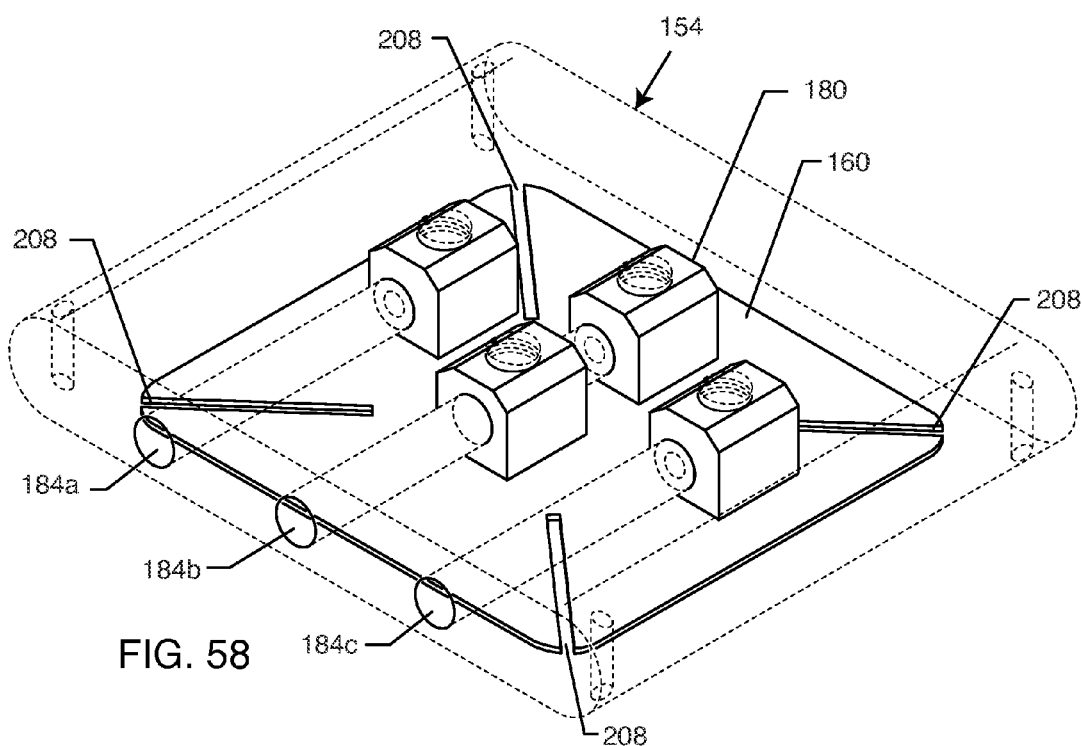
FIG. 58 is a view similar to FIG. 57, showing slots in the energy dissipating surface.

FIG. 58 illustrates the use of novel slots 208 in the EDS plate 160. These slots can be of any number and of any length. Their purpose is to break up eddy currents that could be induced in metal plates 160 or 178 from the gradient or RF fields of the MR scanner. By providing these slots, heating due to such eddy currents is therefore minimized. It will be obvious to those skilled in the art that these slots can be of any number, or of any shape. The use of said slots to minimize eddy currents is applicable to any of the embodiments herein that embody metal plates.

Figure 59:
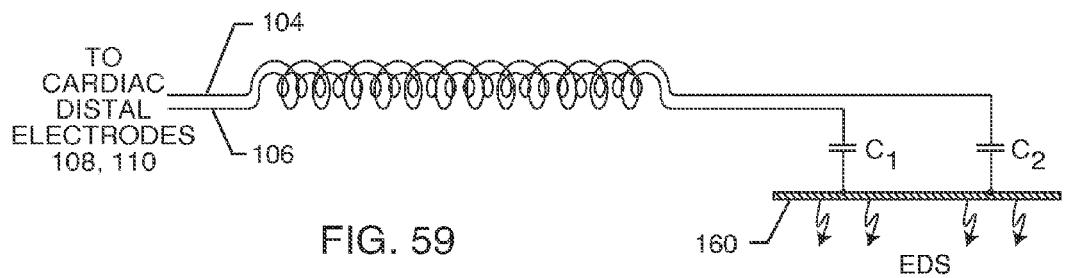
FIG. 59 is an schematic diagram of the structure shown in FIG. 52.

FIG. 59 is a schematic diagram illustrating that the same or two different values of capacitance can be formed by the structure as illustrated in FIG. 52.

Figure 60:
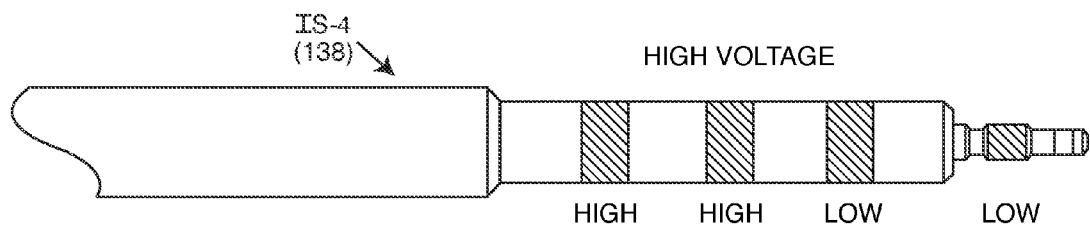
FIG. 60 is a side view of an in-line quadpolar IS-4 connector incorporating both high and low voltage connections.

FIG. 60 shows a view of an in-line quadpolar IS-4 connector 138 which incorporates both high voltage and low voltage connections.

Figure 61:
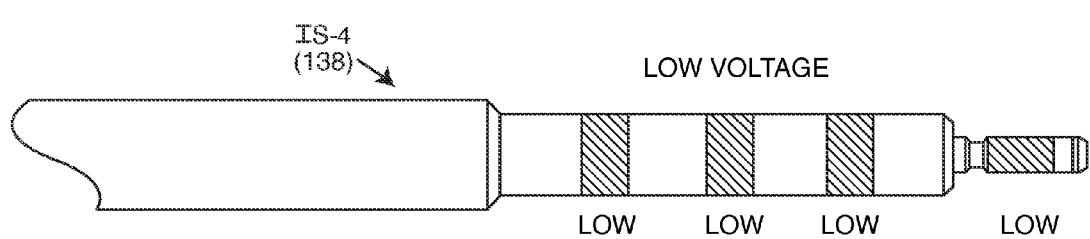
FIG. 61 is a side view of an in-line quadpolar IS-4 connector incorporating only low voltage connections.

FIG. 61 illustrates that the IS-4 connector of FIG. 60 (138) can also embody different configurations. In this case, four low voltage connections. The IS-4 lead has significant advantages in that it offers a significant size reduction in an AIMD or abandoned lead cap 154 header block.

Figure 62:
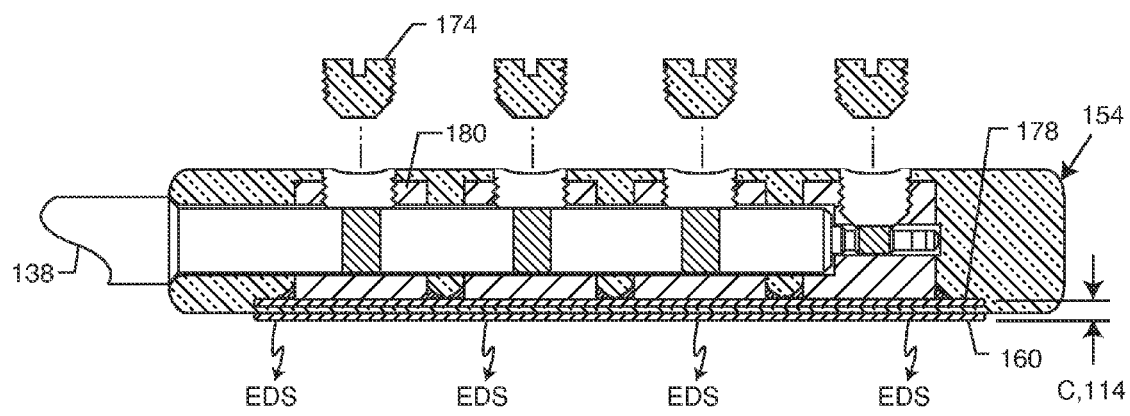
FIG. 62 is a cross-sectional side view of a lead cap designed to terminate the abandoned IS-4 lead connectors of FIGS. 60 and 61.

FIG. 62 is a cross-section drawing of the novel lead cap 154 of the present invention which is designed to terminate an abandoned IS-4 lead connector 138. In this regard, it is very similar to the previous description for FIG. 46.

Figure 63:
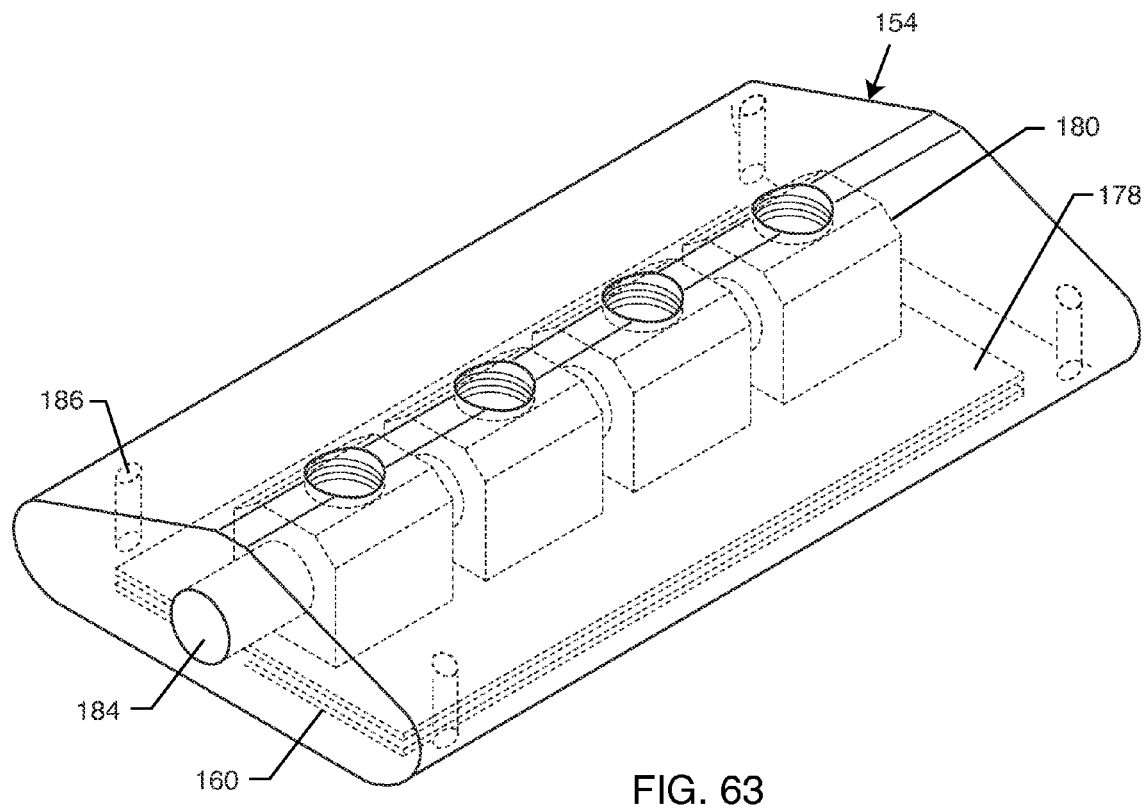
FIG. 63 is an isometric view of the abandoned lead cap of FIG. 62.

FIG. 63 is an isometric view of the IS-4 abandoned lead cap 154 of FIG. 62.

Figure 64:
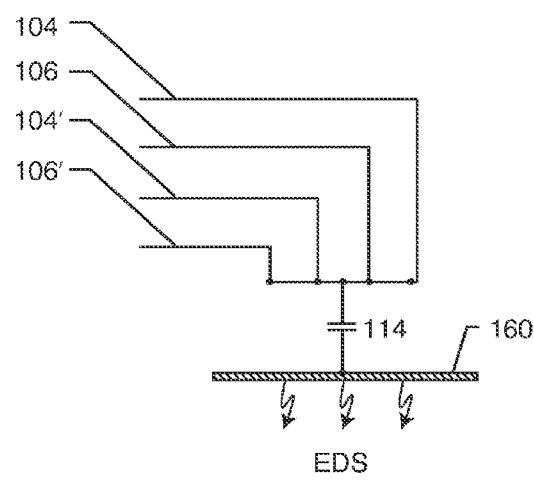
FIG. 64 is an electrical schematic of the abandoned lead cap of FIGS. 62 and 63.

FIG. 64 is a schematic diagram of the IS-4 abandoned lead cap 154 of FIGS. 62 and 63.

Figure 65:
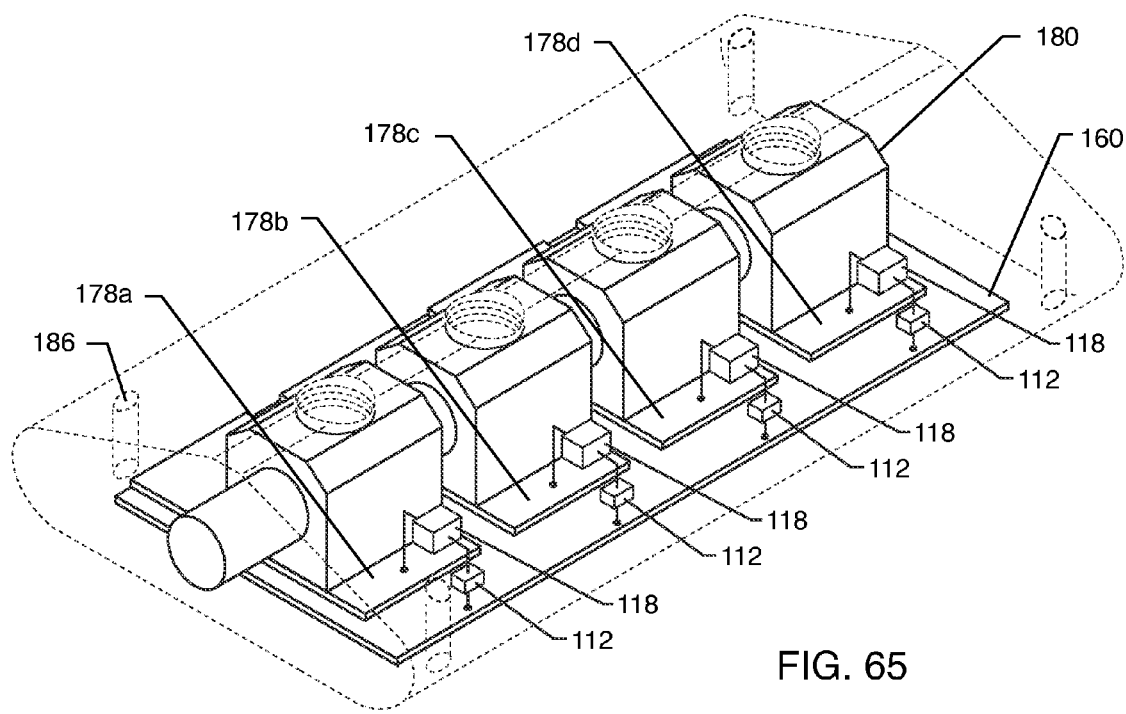
FIG. 65 is an isometric view of the abandoned lead cap of FIG. 63, showing diverter and impeder elements incorporated therein.

FIG. 65 is an illustration of the abandoned lead cap of FIG. 63, showing that any of the features of the present invention, including diverter and/or impeder elements 112 and 118, can be incorporated.

Figure 66:
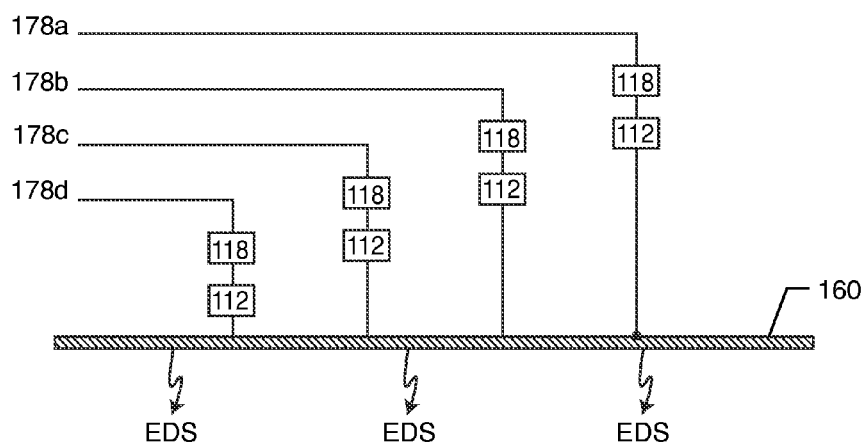
FIG. 66 is an electrical schematic of the abandoned lead cap of FIG. 65.

FIG. 66 is a schematic diagram of the IS-4 abandoned lead cap 154 of FIG. 65.

Figure 67:
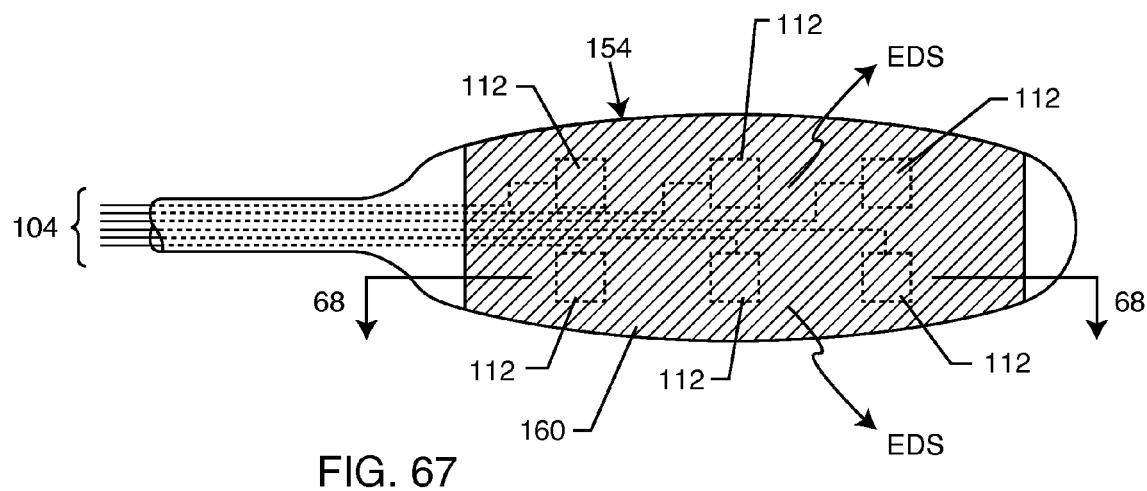
FIG. 67 illustrates a paddle-shaped abandoned lead cap of the present invention.

FIG. 67 illustrates a paddle-shaped abandoned lead cap 154 embodying the present invention. It has a conductive energy dissipating surface 160 shown on one side. A plurality of abandoned leads 104 is shown. The method of connection to the lead cap 154 can be by any other methods described herein. The leads can be directly connected (shorted) to the EDS surface 160. In the preferred embodiment, the leads 104 would be connected through diverter elements 112 to the EDS surface.

Figure 68:
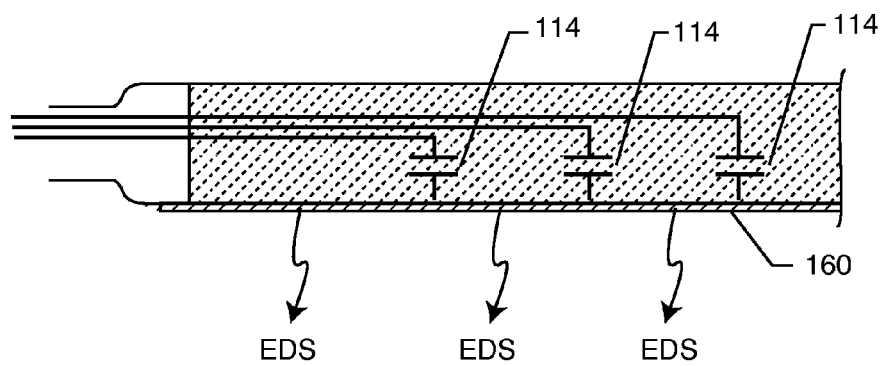
FIG. 68 is a sectional view taken along line 68-68 of FIG. 67.

FIG. 68 is a sectional view taken generally from section 68-68 from FIG. 67. In this case, the diverter elements 112 are shown as capacitor elements 114. As described in previous drawings, all the lead wires could be joined together and connected to a single capacitor element or they could be individually routed to different capacitors as illustrated. By routing to different capacitors, the capacitance values can vary so that the capacitive reactance is carefully balanced to be opposite to the inductive reactance of the various implanted leads. This is in accordance with the maximum energy transfer principles of the present invention.

FIG. 69 is a drawing of a typical IS-1 lead 104, 132 that has been unplugged from an AIMD, such as a cardiac pacemaker. Imagine that the pectoral pocket has been opened up by the surgeon, the pacemaker has been removed and then the surgeon has taken a scissors or other surgical cutting tool and cut off the end of the lead wire at location 70-70. Unfortunately, this snipping off of the lead connectors has been done in the past. Hopefully, with the novel abandoned lead caps of the present invention, this practice can be discontinued in the future. However, for these legacy abandoned leads, there is a need to be able to cap them in a way that improves their MRI safety.

FIG. 70 is the end view of the cut-off lead taken from section 70-70 from FIG. 69. One can see that there are two coaxial or spiral wound lead wires 210 and 212 that run through the lead 104. The inside spiral lead 212 is routed to the tip electrode 108. The outer spiral is connected to the ring or anode electrode 110. The ring and tip electrode wires are electrically insulated from each other within the insulative body of the lead 104. It would be very difficult for the surgeon to remove the insulation and separate out the ring and tip lead wires once the end has been cut off in this manner. Accordingly, a novel method is needed to make contact with these embedded spiral wound or bifilar wound lead conductors.

FIG. 71 is a novel insert 214, shown inverted, with metal spikes 216 as shown. In a preferred embodiment, this would be made of injected molded Grade-23 titanium. The material could also be of platinum, platinum iridium or any other suitable biocompatible material. In addition to injection molding, the spike arrangement could be machined or formed.

The use of the structure, as shown in FIG. 71, is better understood by referring to FIG. 72. The metal spike structure 214 (no longer inverted) is shown in cross-section taken generally from section 72-72 from FIG. 71. The proximal end of the cut-off lead wire from FIG. 70 is first inserted into the bore area 184 until it is fully seated at the end. Then the spike structure 214, which is slightly smaller in diameter than the threads, is inserted into the hole and pushed in through the insulation of the lead 104. The various metal spikes 216 make electrical contact in various places with both the spiral wound ring 210 and tip 212 wiring inside of the lead 104. The set screw 174 is then put in place, and using a torque tool, is firmly screwed in place which also presses against and seats the spikes 214. This has the affect of shorting both the tip 212 and the ring 210 circuits together to metal plate 178. As previously described, a parasitic energy diverting capacitance is formed between the metal plate 178 and the energy dissipating surface 160. In an alternative embodiment, passive component frequency selective reactance components 118 and 112 can also be employed in accordance with the present invention.

Figure 73:
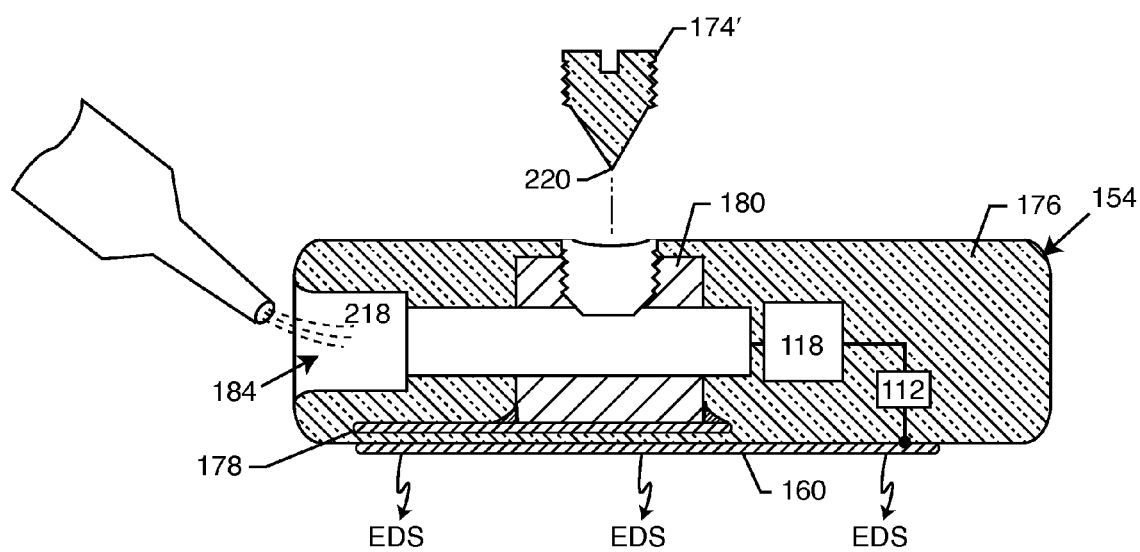
FIG. 73 is a view similar to FIG. 72, showing another method for terminating abandoned leads using a sharp point set screw.

FIG. 73 illustrates another methodology of terminating abandoned leads that do not have a connector or who have had their connector removed. This is also applicable to various Neuromodulation lead systems that are hard wired (in other words, do not have a connector in the first place). One can see that there is a recess or counterbore 184 formed into the plastic non-conductive insulating surface 176 of the abandoned lead cap 154. Once the lead 104 is inserted and the set screw 174' is torqued, then a medical grade adhesive such as silicone 218 is used to fill in the space around the cut-off lead illustrated in FIG. 70 around its circumference into the angular space 184. This prevents moisture intrusion into the lead. A similar medical adhesive would be placed over the set screw 174' so that the lead end and the areas of electrical connection to the tip 212 and ring 210 lead spirals are sealed off from body fluid intrusion.

In a preferred embodiment, the pointed set screw structure 220 in FIG. 73 would be sputtered or plated with a noble biocompatible surface to make better electrical contact. Gold or platinum would be good choices. This is particularly important in the case where structure 174',220 was of titanium or similar metal that could form oxides on the surface.

Figure 74:
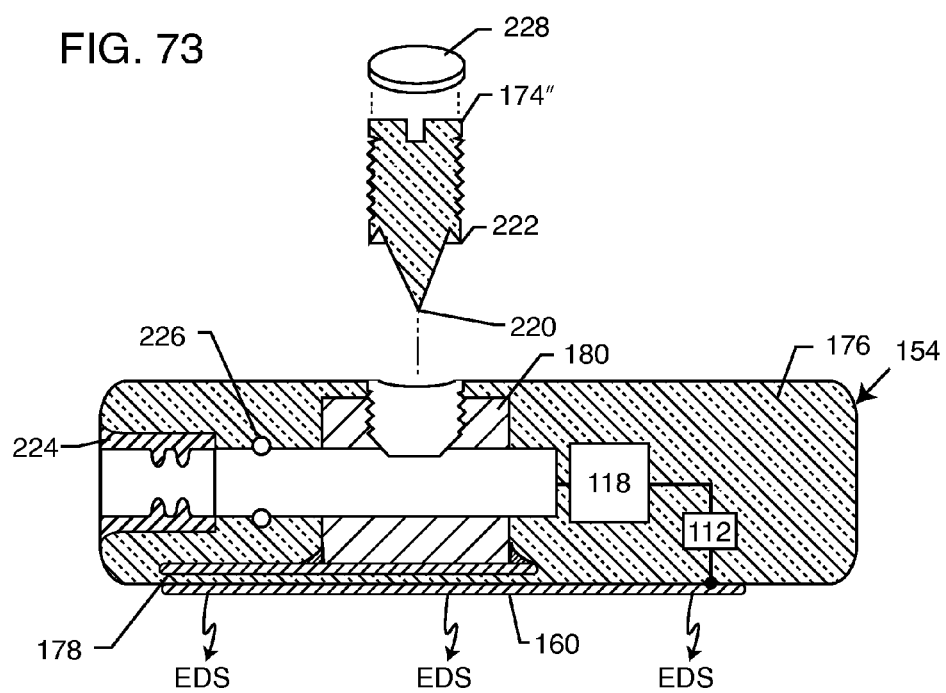
FIG. 74 is a view similar to FIGS. 72 and 73, showing another method for terminating abandoned leads using a sharp point set screw with a secondary piercing ring.

FIG. 74 is very similar to FIG. 73 except that the set screw 174" has been specially modified to have a sharp pointed piercing tip 220 along with a secondary piercing ring 222. When inserted through an abandoned lead 104, the piercing tip 220 is designed to pierce through and bottom out as the set screw 174" is being torqued. The distance between the primary piercing tip 220 and the secondary piercing ring 222 is important such that the secondary piercing ring 222 pierces the ring electrode 210. In this way, one can be assured that the set screw 174" is not screwed in too far and also that all of the imbedded leads 210 and 212 are properly pierced so that a solid electrical connection is made.

An additional feature illustrated in FIG. 74 is the use of silicon or equivalent O-rings 224. When the cutoff lead from FIG. 70 is inserted into place, it is pressed firmly into these O-rings 224 such that moisture will not intrude. Illustrated in FIG. 74 is that any of the energy diverter elements 112 or impeder elements 118 of the present invention can be incorporated. Also shown is an optional secondary O-ring 226 to aid in mechanical capture and in moisture sealing of the inserted lead 104. Referring once again to FIG. 74, shown is a silicon cap 228 which is designed to be squeezed into place after the set screw 174" is seated. This prevents moisture intrusion from body fluid around the thread surfaces of set screw 174'. This plug 228 would be set in place with a small dab of medical grade adhesive.

Figure 75:
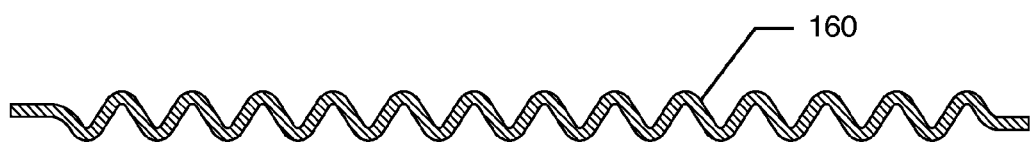
FIG. 75 is an enlarged cross-sectional side view of an energy dissipating surface with a convoluted surface.

FIG. 75 is an enlarged view of any of the energy dissipating surfaces 160 of the novel abandoned lead caps 154 of the present invention. Shown is a convoluted surface such that the surface area of the energy dissipating surfaces increases. This aids in both dissipation of RF energy and in dissipation of thermal energy. Major advantages of the convoluted surface as illustrated in FIG. 75 is that it will also increase the MRI induced RF energy that is transferred and dissipated from an implanted lead 104.

Figure 76:
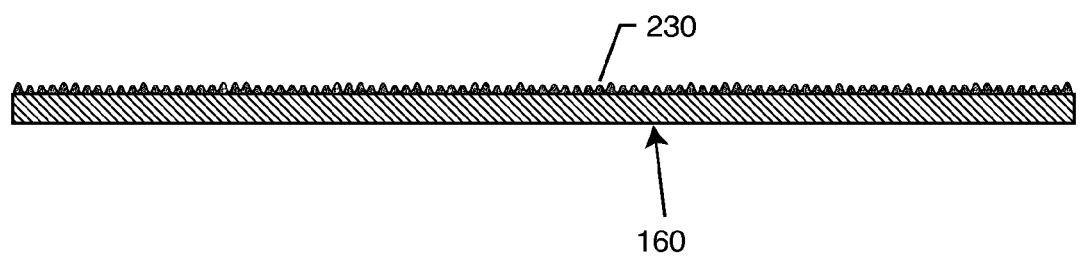
FIG. 76 is an enlarged cross-sectional side view of an energy dissipating surface with a roughened surface.

FIG. 76 is similar to FIG. 75 except that instead of convolutions, a roughened surface provides additional energy dissipation area. The energy dissipating surface 160 area has been roughened 230 to create a high surface area, through, for example, plasma etching, sputtering, chemical etching, or the like. A high surface area can also be accomplished by porous coating deposits utilizing physical vapor deposition, chemical vapor deposition or electron beam deposition processes. Such porous coating deposits can include fractal coatings, metal nitrides, titanium nitrides, metal oxides, metal carbides, or virtually anything that would provide a high surface or porous substrate. In addition, electrochemical deposition of porous coating, such as iridium-oxide, can also be utilized, as well as nucleate high surface area morphologically structured coatings, such as whiskers, sub-micron filaments, tubes, nanotubes, or other morphological structures such as columnar, titanium-nitride or iridium-oxide. Any of these types of surface conditionings can greatly increase the energy dissipating surface area.

Figure 77:
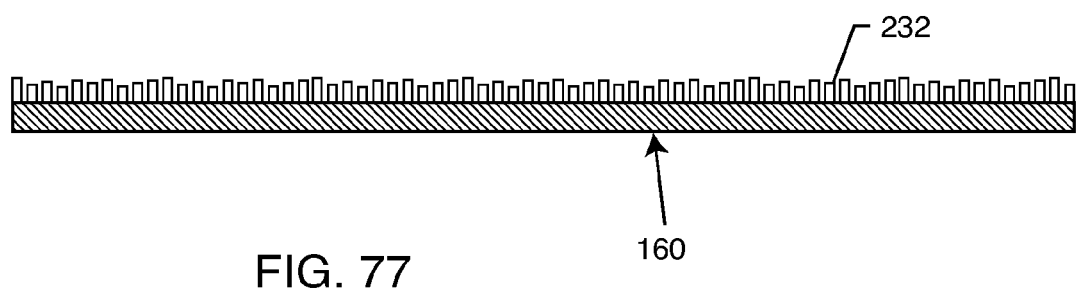
FIG. 77 is view similar to FIG. 76, except that instead of a roughened surface, carbon nanotubes or fractal coatings have been added to the energy dissipating surface.

FIG. 77, which is similar to FIG. 76, illustrates the use of carbon nanotubes or fractal coatings 232 to increase the surface area and therefore the energy dissipation.

In summary, the present invention involves terminating abandoned AIMD leads utilizing novel abandoned lead caps associated with an energy dissipating surface. In general, the abandoned lead cap includes an electrically conductive housing/electrode which works in combination with frequency selective circuits so that the housing of the abandoned lead cap works as an energy dissipating surface. The energy dissipating surface may be disposed within the blood flow of a patient or comprise a plurality of spaced-apart energy dissipating surfaces. The energy dissipating surface may also include one or more slots for reducing eddy current heating therein. Many types of energy dissipating surfaces may be utilized such as convolutions, roughened surfaces and carbon nanotubes. The abandoned lead cap of the present invention may also include an RFID tag associated therewith.

The system for terminating an abandoned implanted lead to minimize heating in a high power electromagnetic field environment in accordance with the present invention, comprises: (1) an implanted abandoned lead having a proximal end and a distal end, and impedance characteristics at a selected RF frequency or RF frequency band; (2) an abandoned lead cap having an energy dissipating surface (EDS surface) which is associated with the proximal end of the implanted abandoned lead; and (3) an energy diversion circuit conductively coupling the implanted abandoned lead to the energy dissipating surface to facilitate transfer to the energy dissipating surface of high frequency energy induced on the implanted abandoned lead at the selected RF frequency or frequency band.

The impedance of the abandoned lead cap may be balanced to the implanted lead impedance such that maximum energy is dissipated within the abandoned lead cap itself. In this case, thermal energy can be dissipated inside the abandoned lead cap, which has a controlled thermal mass and a controlled rate of temperature rise.

The present invention also includes methods of attachment to an abandoned lead that has been cut off as well as to an abandoned lead proximal connector.

Although several embodiments of the invention have been described in detail for purposes of illustration, various modifications may be made without departing from the scope and spirit of the invention. Accordingly, the invention is not to be limited, except as by the appended claims.

What is claimed is:

1. A system for terminating an abandoned implanted lead to minimize heating in a high power electromagnetic field environment, comprising:
   an implanted abandoned lead having a proximal end and a distal end, and
   impedance characteristics at a selected RF frequency or frequency band;
   an abandoned lead cap having an energy dissipating surface and associated with the proximal end of the implanted abandoned lead; and
   an energy diversion circuit conductively coupling the implanted abandoned lead to the energy dissipating surface to facilitate transfer to the energy dissipating surface of high frequency energy induced on the implanted abandoned lead at the selected RF frequency or frequency band.

2. The system of claim 1, wherein the energy diversion circuit comprises one or more passive electronic network components whose impedance characteristics are at least partially tuned to the implanted abandoned lead's impedance characteristics.

3. The system of claim 2, wherein selected RF frequency or frequency band comprises an MRI frequency.

4. The system of claim 3, wherein said MRI frequency comprises a range of MRI frequencies.

5. The system of claim 2, wherein the energy diversion circuit has a reactance and is vectorially opposite to the characteristic reactance of the implanted lead.

6. The system of claim 2, wherein the energy diversion circuit has a capacitive reactance generally equal and opposite to the characteristic inductive reactance of the implanted lead.

7. The system of claim 6, wherein the capacitive reactance and the inductive reactance each have a resistor component.

8. The system of claim 2 or 6, wherein the energy diversion circuit comprises a low pass filter.

9. The system of claim 8, wherein the low pass filter comprises a capacitor, an inductor, a Pi filter, a T filter, an LL filter, or an "n" element filter.

10. The system of claim 2 or 6, wherein the energy diversion circuit comprises at least one series resonant LC trap filter.

11. The system of claim 2, wherein the energy dissipating surface is disposed within the blood flow of a patient.

12. The system of claim 2, including an impeding circuit associated with the energy diversion circuit, for raising the high-frequency impedance of the implanted abandoned lead.

13. The system of claim 12, wherein the impeding circuit comprises an inductor.

14. The system of claim 12, wherein the impeding circuit comprises a bandstop filter.

15. The system of claim 13 or 14, wherein the energy diversion circuit comprises a resistor.

16. The system of claim 13 or 14, wherein the wherein the energy diversion circuit comprises a low pass filter.

17. The system of claim 16, wherein the low pass filter comprises a capacitor, an inductor, a Pi filter, a T filter, an LL filter, or an "n" element filter.

18. The system of claim 13 or 14, wherein the energy diversion circuit comprises at least one series resonant LC trap filter.

19. The system of claim 18, wherein the energy diversion circuit comprises a plurality of LC trap filters resonant respectively at different MRI frequencies.

20. The system of claim 16, wherein the energy diversion circuit comprises a resistor.

21. The system of claim 18, wherein the energy diversion circuit comprises a resistor.

22. The system of claim 9, wherein said energy diversion circuit comprises a unipolar or multipolar feedthrough capacitor.

23. The system of claim 1 or 2, wherein the energy dissipating surface comprises convolutions or fins, for increasing the surface area thereof.

24. The system of claim 1 or 2, wherein the energy dissipating surface includes a roughened surface.

25. The system of claim 24, wherein the roughened surface is formed through plasma or chemical etching, porous or fractal coatings or surfaces, whiskers, morphologically designed columbar structures, vapor, electron beam or sputter deposition of a high surface area energy conductive material, or carbon nanotubes.

26. The system of claim 1 or 2, wherein the implanted lead comprises at least a portion of a probe or a catheter.

27. The system of claim 1 or 2, wherein the energy dissipating surface comprises a plurality of spaced-apart energy dissipating surfaces.

28. The system of claim 1 or 2, wherein the energy dissipating surface comprises a material capable of being visualized during a magnetic resonance scan.

29. The system of claim 1 or 2, wherein the energy dissipating surface includes a biomimetic coating.

30. The system of claim 2, wherein the energy diversion circuit includes at least one non-linear circuit element.

31. The system of claim 30, wherein the at least one non-linear circuit element comprises a transient voltage suppressor.

32. The system of claim 30, wherein the at least one non-linear circuit element comprises a diode or a pin diode.

33. The system of claim 2 or 6, wherein the energy diversion circuit comprises a high pass filter.

34. The system of claim 33, wherein the high pass filter prevents low frequency gradient field-induced energy in the implanted lead or the leadwire from passing through the diversion circuit to the energy dissipating surface.

35. The system of claim 33, wherein the high pass filter comprises a capacitor.

36. The system of claim 35, wherein the high pass filter comprises a resistor in series with a capacitor.

37. The system of claim 33, wherein the high pass filter comprises an LC trap filter.

38. The system of claim 1, wherein the energy diversion circuit comprises a short to the energy dissipating surface.

39. The systems of claim 1 or 2, including an RFID tag associated with the abandoned lead cap.

40. The system of claim 1, wherein the energy dissipating surface comprises a large surface area conductor relative to the proximal end of the implanted abandoned lead.

41. The system of claim 40, wherein the energy dissipating surface has a resistivity greater than 150 microohm centimeters.

42. The system of claim 41, wherein the energy dissipating surface comprises grade 5 or grade 23 titanium.

43. The system of claim 40, wherein the energy dissipating surface includes one or more slots for reducing eddy current heating therein.

44. The system of claim 40, wherein the abandoned lead cap comprises a housing in which the proximal end of the implanted abandoned lead is disposed.

45. The system of claim 44, wherein the abandoned lead cap housing includes at least one conductive block conductively coupled to the proximal end of the implanted abandoned lead.

46. The system of claim 45, wherein the abandoned lead cap housing includes a set screw for locking the proximal end of the implanted abandoned lead within the conductive block.

47. The system of claim 46, wherein the set screw includes a spike, tip or piercing rug to facilitate conductive coupling of the proximal end of the implanted abandoned lead with the conductive block.

48. The system of claim 45, wherein the abandoned lead cap housing includes a threaded locking system for locking the proximal end of the implanted abandoned lead within the conductive block.

49. The system of claim 45, wherein the proximal end of the implanted abandoned lead comprises n IS-1, IS-4 or DF-1 connector.

50. The system of claim 45, wherein the energy diversion circuit is disposed within the abandoned lead cap housing between the conductive block and the energy dissipating surface.

51. The system of claim 50, wherein the energy diversion circuit comprises parasitic capacitance between the conductive block and the energy dissipating surface.

52. The system of claim 50, wherein the energy diversion circuit comprises at least one discrete electronic network component taken from the group of an inductor, a capacitor, a resistor, a diode, or a pin diode.

53. The system of claim 52, wherein the at least one diode electronic network component is disposed within a hermetically sealed biocompatible package.

54. The system of claim 44, wherein the abandoned lead cap housing includes a seal which engages the lead to isolate the proximal end of the implanted abandoned lead from body fluid.

55. The system of claim 1, wherein the abandoned lead cap comprises the energy dissipating surface and a housing in which the proximal end of the implanted lead is disposed.

56. A system for terminating an abandoned implanted lead to minimize heating in a high power electromagnetic field environment, comprising:
an implanted abandoned lead having a proximal end and a distal end, and impedance characteristics at a selected RF frequency or frequency band;
an abandoned lead cap associated with the proximal end of the implanted abandoned lead, comprising an energy dissipating surface and a housing in which the proximal end of the implanted lead is disposed; and
an energy diversion circuit conductively coupling the implanted abandoned lead to the energy dissipating surface to facilitate transfer to the energy dissipating surface of high frequency energy induced on the implanted abandoned lead at the selected RF frequency or frequency band.

* * * * *